US010450327B2

(12) United States Patent
Kang et al.

(10) Patent No.: US 10,450,327 B2
(45) Date of Patent: Oct. 22, 2019

(54) EPIDITHIODIOXOPIPERAZINE COMPOUND OR ITS DERIVATIVES, AND THE USE THEREOF

(71) Applicant: VASTHERA Co. Ltd., Seoul (KR)

(72) Inventors: Sang Won Kang, Seoul (KR); Dong Hoon Kang, Gyeonggi-do (KR); Doo Jae Lee, Seoul (KR)

(73) Assignee: Vasthera Co. Ltd., Seoul (KR)

( * ) Notice: Subject to any disclaimer, the term of this patent is extended or adjusted under 35 U.S.C. 154(b) by 0 days.

(21) Appl. No.: 16/024,454

(22) Filed: Jun. 29, 2018

(65) Prior Publication Data

US 2018/0305377 A1 Oct. 25, 2018

Related U.S. Application Data

(60) Continuation of application No. 15/440,655, filed on Feb. 23, 2017, now Pat. No. 10,045,995, which is a division of application No. 14/286,929, filed on May 23, 2014, now Pat. No. 9,765,090, which is a continuation-in-part of application No. PCT/KR2012/010073, filed on Nov. 26, 2012.

(30) Foreign Application Priority Data

Nov. 25, 2011 (KR) .................. 10-2011-0124603
May 24, 2013 (KR) .................. 10-2013-0059351

(51) Int. Cl.
*C07D 513/08* (2006.01)
*C12Q 1/26* (2006.01)
*A61K 31/00* (2006.01)
*A61K 31/548* (2006.01)

(52) U.S. Cl.
CPC ............ *C07D 513/08* (2013.01); *A61K 31/00* (2013.01); *A61K 31/548* (2013.01); *C12Q 1/26* (2013.01); *G01N 2333/90212* (2013.01); *G01N 2500/02* (2013.01)

(58) Field of Classification Search
CPC .................................................. C07D 513/08
See application file for complete search history.

(56) References Cited

U.S. PATENT DOCUMENTS 3,562,253 A 2/1971 Trown et al.
7,981,878 B2 7/2011 Hubmann et al.

FOREIGN PATENT DOCUMENTS

WO WO2006/066775 A1 6/2006
WO WO2006/135949 A2 12/2006
WO WO2013/077709 A1 5/2013

OTHER PUBLICATIONS

Chen et al., "Ecology-based screen identifi.es new metabolites from a *Cordyceps*-colonizing fungus as cancer cell proliferation inhibitors and apoptosis inducers," Cell Prolif., 2009, 00:1-10.
Lobkovsky et al. CAS: 142: 407774, 2004, 2 pages.
Yano et al., "Chetomin induces degradation of XIAP and enhances TRAIL sensitivity in urogenital cancer cells." Int J. Oncol, 2011, 38(2): 365-74 (abstract only).
European Search Report from corresponding European Patent Application No. 14801426.9, dated Dec. 15, 2016, 6 pages.
PCT International Search Report from corresponding PCT Application No. PCT/KR2014/004678, dated Sep. 22, 2014.
Choi et al., "Discovery of Gliotoxin as a new Small Molecule Targeting Thioredoxin Redox System", Biochemical and Biophysical Research Communications 359 (2007) 523-528.
Chinese Office Action with Translation from corresponding Chinese Patent Application No. 201480019817.1, dated Jun. 24, 2016, 24 pages.
Cook et al., "Epidithiodiketopiperazines Block the Interaction between Hypoxia-inducible Factor-1α(HIF-1α) and p300 by a Zinc Ejection Mechanism", The Journal of Biological Chemistry vol. 284, No. 39, pp. 26831-26838, Sep. 25, 2009.
DeLorbe et al., "General Approach for Preparing Epidithiodioxopiperazines from Trioxopiperazine Precursors: Enantioselective Total Syntheses of (+)- and (−)-Gliocladine C, (+)-Leptosin D, (−)-T988C, (+)-Bionectin A, and (+)-Gliocladin A," J. Am. Chem. Soc. 2013, 135, 4117-4128.
Dubey et al., "Suppression of Tumor Growth by Designed Dimeric Epidithiodiketopiperazine Targeting Hypoxia-Inducible Transcription Factor Complex" J. Am. Chem. Soc. 2013, 135, 4537-4549.
Pozo et al., "Gliotoxin Inhibits Neointimal Hyperplasia after Vascular Injury in Rats", J Vasc Res 2009;46:278-289.

(Continued)

*Primary Examiner* — Rei Tsang Shiao
(74) *Attorney, Agent, or Firm* — Cooley LLP

(57) ABSTRACT

The present invention relates to an epidithiodioxopiperazine derivative represented by the following Chemical Formula 1 or its reduced derivative; a method for preparing a compound represented by Chemical Formula 1 having improved intracellular permeability and mimicking the activity of 2-Cys-Prx in its reduced form in the cells; a pharmaceutical composition for preventing or treating vascular diseases comprising an epidithiodioxopiperazine compound or its derivatives or pharmaceutically acceptable salts thereof as an active ingredient; a drug delivery device for local administration including the pharmaceutical composition; and a pharmaceutical composition for inhibiting melanoma metastasis comprising the epidithiodioxopiperazine compound or its derivatives or pharmaceutically acceptable salts thereof as an active ingredient.

[Chemical Formula 1]

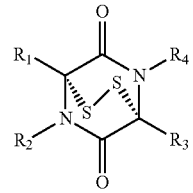

8 Claims, 55 Drawing Sheets

Specification includes a Sequence Listing.

(56) References Cited

OTHER PUBLICATIONS

Trown's CAS: 75: 20444, 1971, 1 page.
Kishi et al., CAS: 79: 137089, 1973, 2 pages.
Yoshimura et al. CAS: 83: 43268, 1975, 1 page.
Gregory et al. CAS: 89:24765, 1978, 2 pages.
Chai et al. CAS:130:324843, 1999, 1 page.
Fukuyama et al. CAS: 86: 72577, 1977, 1 page.
Fukuyama et al., "A New Synthesis of Epidithiapiperazinediones," Tetrahehedron Letters, 1976, 38:3393-3396.
Jiang et al., "Synthesis and Activity of NewEpipolythiopiperazine-2,5-dione Compounds. I," Aust. J. Chem., 46:1743-1754 (1993).
Hurne et al., "Resolution and biologicalactivities of optical isomers of 1,4-diethyl-3,6-epidithiopiperazine-2,5-dione," Bioorganic & Medicinal Chemistry Letters 7(20):2645-2650 (1997).

EPIDITHIODIOXOPIPERAZINE COMPOUND OR ITS DERIVATIVES, AND THE USE THEREOF

CROSS-REFERENCES TO RELATED APPLICATIONS

This application is a continuation application of U.S. patent application Ser. No. 15/440,655, filed Feb. 23, 2017, which is a divisional application of U.S. patent application Ser. No. 14/286,929, filed May 23, 2014, which is a continuation-in-part of International Application No. PCT/KR2012/010073, filed Nov. 26, 2012, which application claims priority to Korean Patent Application No. 10-2013-0059351, filed May 24, 2013 and Korean Patent Application No. 10-2011-0124603, filed Nov. 25, 2011. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_028_02US_ST25.txt. The text file is 3 KB, was created on Jun. 29, 2018, and is being submitted electronically via EFS-Web.

BACKGROUND OF THE INVENTION

1. Field of the Invention

The present invention relates to an epidithiodioxopiperazine derivative represented by the following Chemical Formula 1 or its reduced derivative; a method for preparing a compound represented by Chemical Formula 1 having improved intracellular permeability and mimicking the activity of 2-Cys-Prx in its reduced form in the cells; a pharmaceutical composition for preventing or treating vascular diseases comprising an epidithiodioxopiperazine compound or its derivatives or pharmaceutically acceptable salts thereof as an active ingredient; a drug delivery device for local administration including the pharmaceutical composition; and a pharmaceutical composition for inhibiting melanoma metastasis comprising the epidithiodioxopiperazine compound or its derivatives or pharmaceutically acceptable salts thereof as an active ingredient.

[Chemical Formula 1]

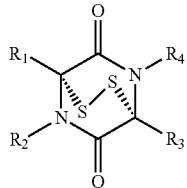

2. Description of the Related Art

Artherosclerosis refers to a state in which inflammations are developed by the buildup of fatty plaques containing cholesterol, phospholipid, calcium and the like in the vascular intima, and blood supply is inhibited by the arteries losing resilience and becoming narrowed, or the rupture or the dissection of blood vessels due to increased pressure. Particularly, arteriostenosis developed therefrom reduces blood supply causing a lack of nutrients and oxygen, and this becomes the main cause of vascular diseases. The vascular diseases generally include artherosclerosis, heart diseases such as cardiac insufficiency, hypertensive heart disease, arrhythmia, myocardial infarction and angina pectoris, and vascular diseases such as stroke and peripheral vascular disease.

As methods for overcoming this angiostenosis, there is artery graft surgery that is a surgical method, and percutaneous angioplasty that is a vasodilating method that does not accompany surgery. Percutaneous angioplasty includes percutaneous vascular balloon dilatation, percutaneous vascular stent grafting, and the like. The percutaneous vascular balloon dilatation is a method of inserting a guiding conduit via femoral or brachial arteries and locating the conduit at the vascular entry point with a lesion, locating a conduit to which a balloon is attached at the end at the area of vascular stenosis via the inside of this guiding conduit, then widening the narrowed blood vessel by inflating the balloon and pressing the plaque and the like, thereby improving the blood flow of the blood vessel. In addition, the stent grafting is a method of locating the balloon covered with wire mesh at the area of stenosis, and then covering the inner wall of the blood vessel by inflating the balloon, and the stent such as this is used for treating complications caused by the inflation of the balloon, since the incidence of restenosis is low compared to an independent balloon dilatation procedure, and the stent acts as a support with respect to the vascular inner wall. This interventional procedure using angioplasty is simpler than a method involving a surgical operation, lowers the risk due to general anesthesia, and has high success rates, thereby causing it to be widely used globally.

Vascular restenosis is a diagnosis made by angiography, and refers to a case in which the stenosis of vessel diameter is 50% or more in a follow-up angiography after angioplasty. As the amount of procedures using stents has increased by approximately 70%, the incidence of restenosis has decreased, however, vascular restenosis is still developed at a rate of approximately 30% for patients who have undergone angioplasty (balloon dilatation and stent grafting). Although the mechanism of the restenosis has not yet been established exactly, it has been known that a growth factor and cytokine are locally secreted due to the injury of endothelial cells during a procedure, and the growth factor and the cytokine induce the proliferation and the migration of vascular smooth muscle, thereby narrowing the aortic lumen resulting in restenosis. Accordingly, the proliferation of smooth muscle cells has recently been acknowledged up as a major clinical problem that limits the efficiency of angioplasty. As a result, improved stents that release drugs or materials inhibiting the proliferation of vascular smooth muscle cells have been developed and used in clinical trials. However, the drugs currently used for this purpose have a limitation in their use in clinical trials since the drugs are highly toxic and thereby prevent the hyperplasia of intima through the mechanism of killing vascular smooth muscle cells, and the toxicity kills endothelial cells as well as the smooth muscle cells. Therefore, there is an urgent need to develop drugs capable of facilitating the recovery of injured endothelial cell layers while selectively suppressing the growth of vascular smooth muscle cells.

Meanwhile, gliotoxin (GT), a representative material having an epidithiodioxopiperazine (ETP) structure, has been shown to exert various pharmacological activities such as immune suppression, anti-cancer, and antivirus activities. In addition, chaetocin and chetomin, which are epidithiodioxopiperazine derivatives, have also been shown to have anti-cancer activities.

As described above, numerous efforts have been made to seek molecular targets to utilize epidithiodioxopiperazine compounds as therapeutic agents. As a result, gliotoxin has been shown to inhibit several enzymes such as NF-κB, farnesyltransferase and phagocytic NOX2, while chaetocin inhibits thioredoxin reductase or histone methyltransferase. In addition, chetomin has been shown to inhibit the interaction between hypoxia-inducible factor-1 (HIF-1) and p300. Despite the fact that partial cellular activities of the ETP compounds have been identified, it has been hard to deduce a logical correlation between their chemical structures and cellular activities due to a diversity of their structures. More specifically, the physiological activity and celluar function of the dithioketopiperazine ring structure, which is known as a common structure of the ETP compound and its derivatives has not been uncovered.

In view of the above, the inventors of the present invention have made various efforts to seek materials capable of preventing or treating vascular diseases by mimicking the activity of 2-Cys-Prx, that is known to suppress intimal hyperplasia, and, based on the idea that ETP compounds exhibit the activity of peroxiredoxin II (PrxII), one type of 2-Cys-Prx, in the cells, synthesized a series of novel ETP derivatives having an intramolecular disulfide bridged bond, and demonstrated that the derivatives inhibit PDGF-inducible proliferation and migration in vascular smooth muscle cells and promote VEGF-inducible proliferation and migration in endothelial cells by mimicking the intracellular activity of PrxII, and thereby impede intimal hyperplasia due to the excess proliferation of vascular smooth muscle cells, and enhance the recovery of vascular endothelial layers, that is, reendothelization, and ultimately, are useful in preventing or treating vascular diseases. Furthermore, based on the idea that the ETP compounds can mimic the intracellular activity of 2-Cys-Prx, in particular, PrxII, the inventors have demonstrated that the ETP compounds can inhibit the metastasis of malignant melanoma induced by PrxII deficiency or inactivation, and thereby completing the present invention.

SUMMARY OF THE INVENTION

It is an object of the present invention to provide an epidithiodioxopiperazine derivative represented by the following Chemical Formula 1 or its reduced derivative, or its pharmaceutically acceptable salt thereof:

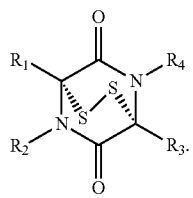

[Chemical Formula 1]

Another object of the present invention is to provide a composition comprising the derivative.

Still another object of the present invention is to provide a method for preparing the compound represented by Chemical Formula 1 having improved intracellular permeability and mimicking the activity of 2-Cys-Prx in its reduced form in the cells, the method including the step of forming an intramolecular disulfide bridged bond from a dimercaptopiperazinedione derivative represented by the following Chemical Formula 2 using an oxidation reaction:

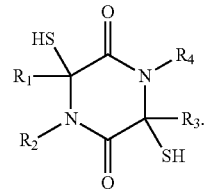

[Chemical Formula 2]

Still another object of the present invention is to provide a pharmaceutical composition for preventing or treating vascular diseases comprising the epidithiodioxopiperazine compound represented by Chemical Formula 1, its derivatives, or pharmaceutically acceptable salts thereof as an active ingredient, and a method for treating vascular diseases including administering the pharmaceutical composition into a subject suspected of having vascular diseases.

Still another object of the present invention is to provide a drug delivery device for local administration comprising the pharmaceutical composition.

Still another object of the present invention is to provide a pharmaceutical composition for inhibiting melanoma metastasis including the epidithiodioxopiperazine compound represented by Chemical Formula 1 or its derivatives, or pharmaceutically acceptable salts thereof as an active ingredient, and a method for inhibiting melanoma including administering the pharmaceutical composition into a subject suspected of melanoma metastasis.

Still another object of the present invention is to provide a method for screening a preventive or therapeutic agent for vascular restenosis including identifying whether a compound including one or more epidithiodioxopiperazine rings represented by Chemical Formula 47 exhibits a 2-Cys-peroxiredoxin (2-Cys-Prx) activity; and determining the compound as an preventive or therapeutic agent for vascular restenosis when a NADPH oxidation reaction or $H_2O_2$ reduction reaction occurs.

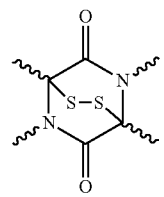

[Chemical Formula 47]

DETAILED DESCRIPTION OF THE PREFERRED EMBODIMENTS

As one aspect to achieve the objects of the present invention, the present invention provides an epidithiodioxopiperazine derivative represented by the following Chemical Formula 1 or its reduced derivative, or a pharmaceutically acceptable salt thereof.

[Chemical Formula 1]

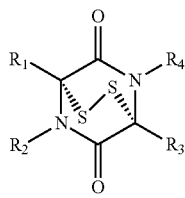

In Chemical Formula 1, $R_1$ to $R_4$ are each independently hydrogen, a halogen atom, a hydroxyl group, linear or branched C1 to C6 alkyl, alkenyl or alkynyl, linear or branched C1 to C6 alkoxy, linear or branched C1 to C6 hydroxyalkyl, substituted or unsubstituted benzyl, linear or branched C1 to C6 alkylaryl, a linear or branched C1 to C6 perfluoroalkyl group, a substituted or unsubstituted aryl group, a substituted or unsubstituted perfluoroaryl group, a substituted or unsubstituted heteroaryl group including an oxygen, nitrogen or sulfur atom in a ring as a heteroatom, or a substituted or unsubstituted epidithiodioxopiperazine group, and the alkyl and the aryl group may optionally include a heteroatom of oxygen, nitrogen or sulfur in the middle of the chain, and each of the substituted epidithiodioxopiperazine groups may independently optionally include substituents defined above and may have a structure identical to or different from mother nucleus epidithiodioxopiperazine;

or $R_1$ and $R_2$, and $R_3$ and $R_4$ each independently form a substituted or unsubstituted C3 to C6 cycloalkyl group with a carbon atom to which these are attached; or form a substituted or unsubstituted heterocyclic ring having 5 to 8 ring atoms with a carbon atom to which these are attached, and additional carbon or heteroatoms, and herein, 1 or 2 ring atoms of the heterocyclic ring are selected from nitrogen (N), oxygen (O) or sulfur (S), however, compounds represented by the following Chemical Formulae 15 to 46 are not included.

Chemical Formula 15

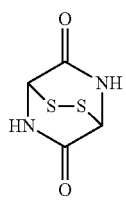

Chemical Formula 16

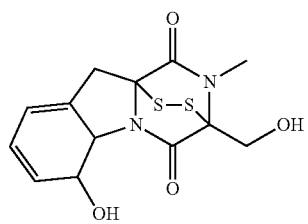

Chemical Formula 17

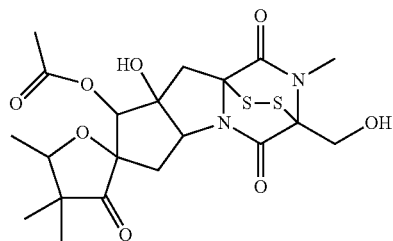

Chemical Formula 18

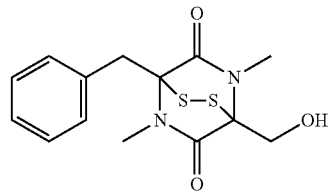

Chemical Formula 19

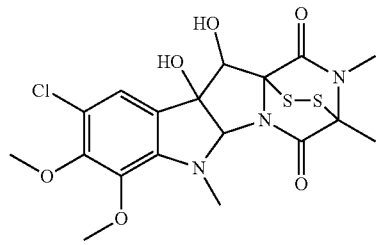

Chemical Formula 20

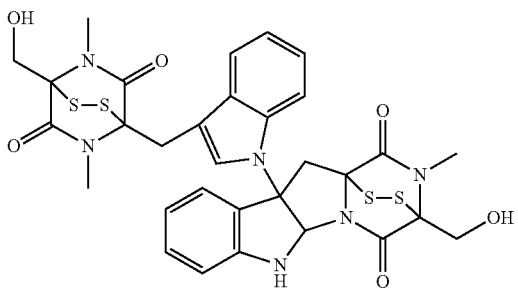

Chemical Formula 21

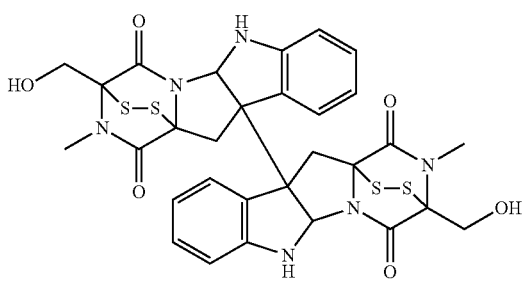

Chemical Formula 22
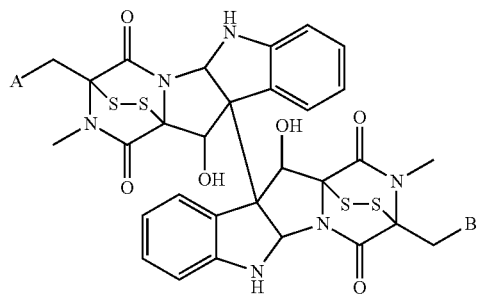
A and B are each independently hydrogen; methoxy; or a hydroxyl group.
Chemical Formula 23
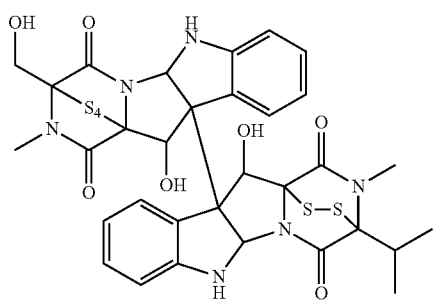
Chemical Formula 24
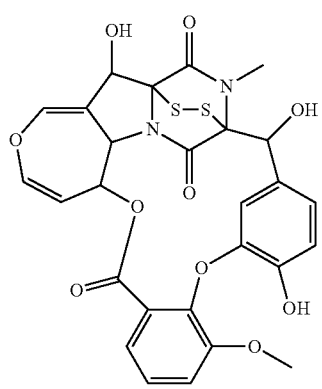
Chemical Formula 25
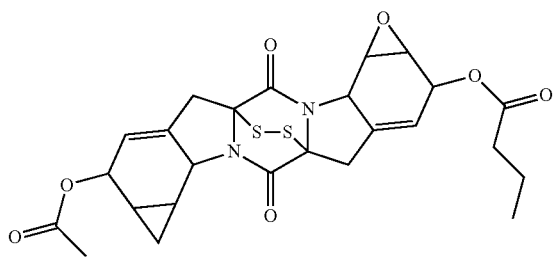
Chemical Formula 26
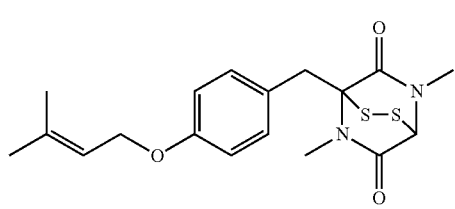
Chemical Formula 27
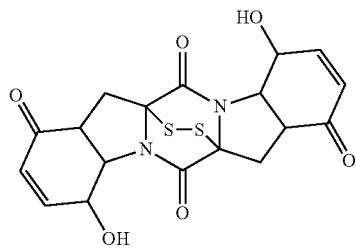
Chemical Formula 28
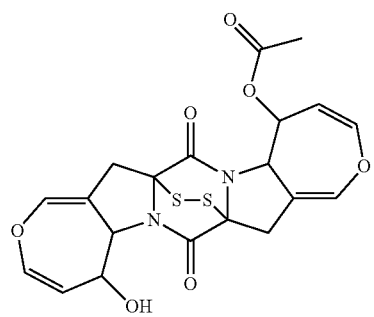
Chemical Formula 29
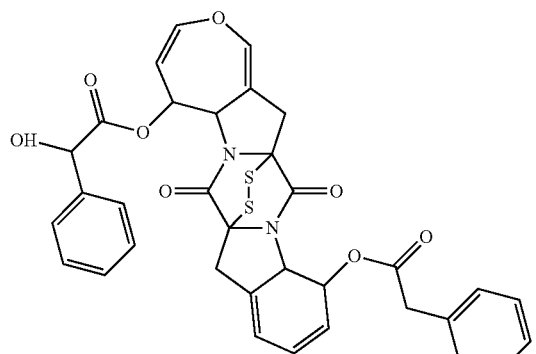
Chemical Formula 30
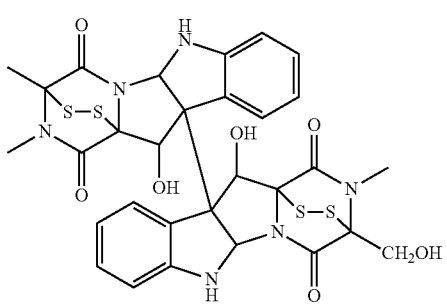
Chemical Formula 31
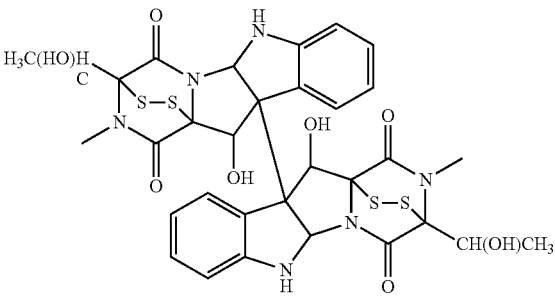

Chemical Formula 32
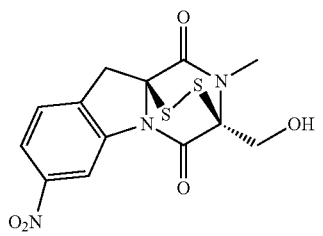
Chemical Formula 33
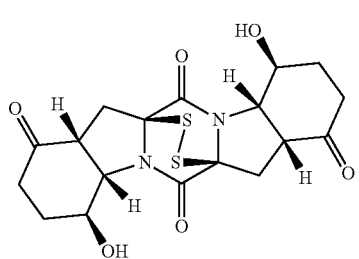
Chemical Formula 34
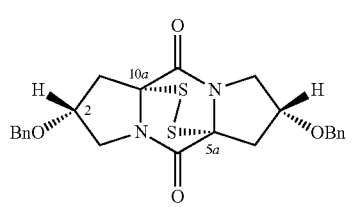
Chemical Formula 35
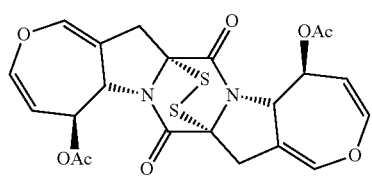
Chemical Formula 36
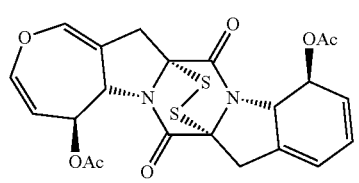
Chemical Formula 37
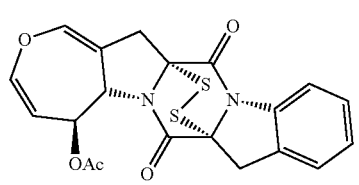
Chemical Formula 38
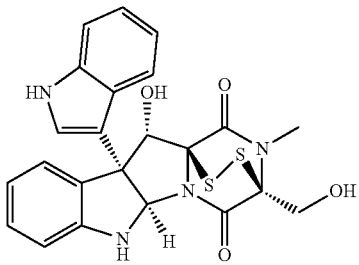
Chemical Formula 39
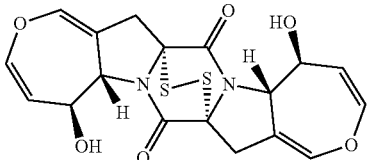
Chemical Formula 40
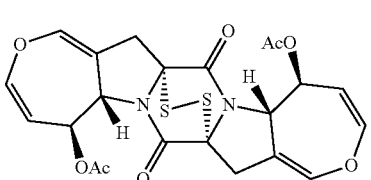
Chemical Formula 41
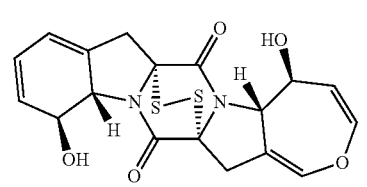
Chemical Formula 42
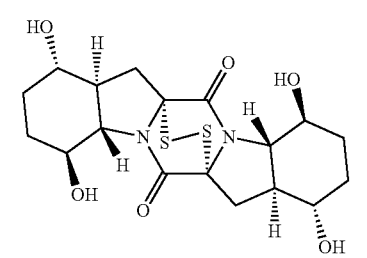
Chemical Formula 43
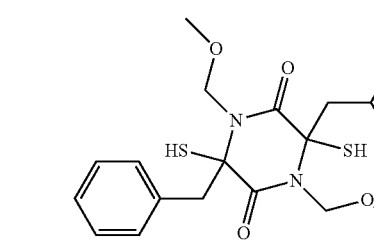
Chemical Formula 44
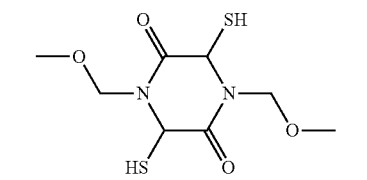
Chemical Formula 45
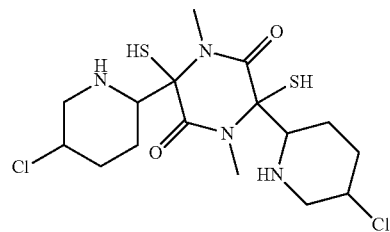

Chemical Formula 46

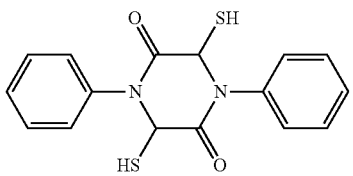

The epidithiodioxopiperazine derivative represented by Chemical Formula 1 or its reduced derivative may be separated from natural sources, acquired from natural sources and then prepared by chemical reforming, or prepared from chemical synthesis by those skilled in the art referencing known preparation methods. Preferably, the epidithiodioxopiperazine derivative may be used by being separated from bacteria, a culture medium thereof, or metabolites according to known methods in the art, or prepared from syntheses using methods described in the examples of the present invention. The reduced derivative of the epidithiodioxopiperazine derivative according to the present invention may be used as a precursor for the synthesis of the epidithiodioxopiperazine derivative having the same substituents. Specific methods of synthesizing the epidithiodioxopiperazine derivative from the reduced derivative will be described later.

Preferably, $R_1$ to $R_4$ of the derivative may be each independently hydrogen, linear or branched C1 to C6 alkyl or alkenyl, alkoxybenzyl, alkoxyalkyl or benzhydryl, and specifically, $R_1$ to $R_4$ may be each independently hydrogen, methyl, n-butyl, allyl, 4-methoxybenzyl, 3-methoxypropyl or benzhydryl.

More preferably, $R_1$ and $R_3$ are hydrogen, $R_2$ and $R_4$ are the same as each other, and may be linear or branched C1 to C6 alkyl or alkenyl; alkoxybenzyl; alkoxyalkyl or benzhydryl, and specifically, may be methyl, n-butyl, allyl, 4-methoxybenzyl, 3-methoxypropyl or benzhydryl;

$R_2$ and $R_4$ may be linear or branched C1 to C6 alkyl such as methyl, propyl or n-butyl, $R_1$ and $R_3$ may be each independently hydrogen; or linear or branched C1 to C6 alkyl such as methyl, propyl or n-butyl;

$R_1$ and $R_3$ are hydrogen, and $R_2$ and $R_4$ may be each independently hydrogen; or alkoxybenzyl such as 4-methoxybenzyl, but are not limited thereto.

Most preferably, the derivative may be a derivative that is any one of compounds represented by the following Chemical Formulae 7 to 14, or its reduced derivative.

[Chemical Formula 7]

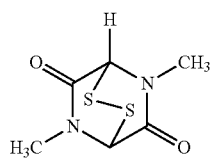

[Chemical Formula 8]

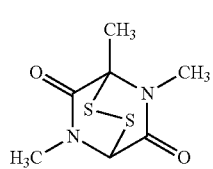

[Chemical Formula 9]

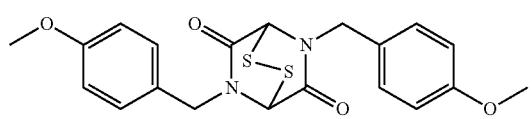

[Chemical Formula 10]

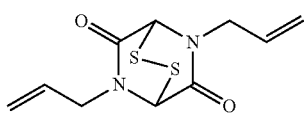

[Chemical Formula 11]

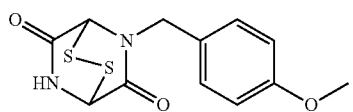

[Chemical Formula 12]

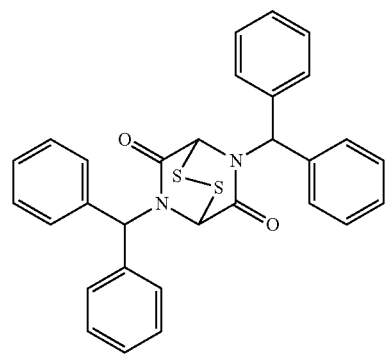

[Chemical Formula 13]

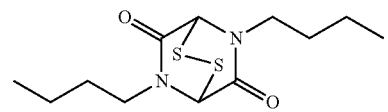

[Chemical Formula 14]

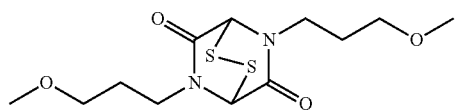

In addition, when the compound represented by Chemical Formula 1 has stereoisomers, the present invention includes all the stereoisomers.

In another aspect, the present invention provides a method for preparing a compound represented by Chemical Formula 1, said derivative having improved intracellular permeability and mimicking the activity of 2-Cys-Prx in its reduced form in the cells, the method including forming an intramolecular disulfide bridged bond from a dimercaptopiperazinedione derivative represented by the following Chemical Formula 2 using an oxidation reaction.

[Chemical Formula 2]

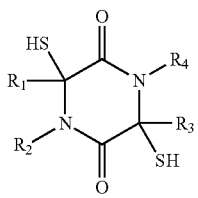

In Chemical Formula 2, $R_1$ to $R_4$ are the same as those defined above.

One feature of the epidithiodioxopiperazine derivative of the present invention is in mimicking the activity of 2-Cys-Prx in the cells. The "2-Cys-Prx" is a thiol-specific antioxidant protein playing the role of protecting cells through a peroxidase activity that reduces hydrogen peroxide, peroxynitrite and other hydroperoxides in the cells. The functional unit of 2-Cys-Prx is a homodimer, and the unit has an intrinsic intramolecular oxidation-reduction active disulfide center that plays an important role in the activity of the enzyme. Each cysteine of the dimer is present as a thiol group in the reduced state. Meanwhile, when being reacted with peroxide, the peroxidatic cysteine of 2-Cys-Prx is oxidized to a sulfenic acid intermediate, and is differentiated from other small unit cysteines of the dimer maintaining a thiol group, and the sulfenic acid group and the thiol group of the intermediate form an intramolecular disulfide bridged bond by dehydration condensation. For example, in the cells, the 2-Cys-Trx is oxidized from a reduced type that includes two thiol groups to an oxidized type in which the two thiol groups form an intramolecular disulfide bridged bond with each other, and reduces intracellular peroxide. Herein, the oxidized 2-Cys-Prx including an intramolecular disulfide bridged bond may be converted to a reduced type having two thiol groups, which is an active type, by an oxidation-reduction system including thioredoxin (Trx) and thioredoxin reductase (TR); alkyl hydroperoxide reductase (AhpF); trypanothione reductase, trypanothione and trypparedoxin or lipoamide dehydrogenase, dihydrolipoyltranssuccinylase (SucB), AhpD and the like.

Another feature of the epidithiodioxopiperazine derivative of the present invention is in the presence of an intramolecular disulfide bridge. This characteristic chemical structure involves in intracellular intake, therefore, once the compounds are introduced into the cells, the compounds are bound in the cells by being accumulated at a much higher intracellular concentration than expected (P. H. Bernardo et al., 2003, *J. Biol. Chem.*, 278: 46549). For this reason, the epidithiodioxopiperazine derivative according to the present invention may effectively prevent or treat vascular diseases even when administered in very low concentrations capable of avoiding intrinsic cytotoxicity.

As described above, the epidithiodioxopiperazine derivative of the present invention is designed to include an intramolecular disulfide bridged bond and thereby is readily introduced into the cells, and may reduce peroxide by being quickly converted to a molecule having two thiol groups by an intracellular oxidation-reduction system, and as a result, may effectively mimic the activity of 2-Cys-Prx in the cells. Although not limited thereto, the intracellular oxidation-reduction system is preferably an oxidation-reduction system including thioredoxin and thioredoxin reductase.

The dimercaptopiperazinedione derivative represented by Chemical Formula 2 may be prepared by the steps of preparing an intermediate that includes a ring structure including 4 sulfur atoms represented by the following Chemical Formula 4 by reacting a piperazinedione derivative represented by the following Chemical Formula 3 with sulfur (S) and lithium bis(trimethylsilyl)amide (LiHMDS) or NaHMDS, and reducing the intermediate to form 2 thiol groups from the ring structure including 4 sulfur atoms.

[Chemical Formula 3]

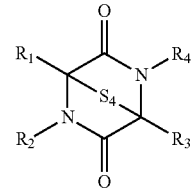

[Chemical Formula 4]

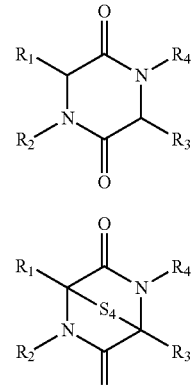

In Chemical Formulae 3 and 4, $R_1$ to $R_4$ are the same as those defined above.

Herein, the reduction reaction may be carried out using reactions known in the art without limit, and may be preferably carried out using a hydride-series reducing agent such as sodium borohydride or lithium aluminum hydride. More preferably, the reaction may be carried out using sodium borohydride; however, the reaction is not limited thereto.

In addition, the dimercaptopiperazinedione derivative represented by Chemical Formula 2 may be prepared to include two thiol groups by preparing an intermediate represented by the following Chemical Formula 6 including a thioacetate group by reacting a halogen atom-substituted piperazinedione derivative represented by the following Chemical Formula 5 with an alkali metal salt of thioacetic acid (MSAc), and then reacting the intermediate with an acid solution to substitute the acetyl group bonded to the sulfur atom with a hydrogen atom.

[Chemical Formula 5]

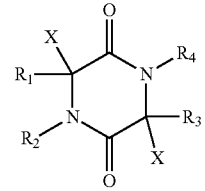

[Chemical Formula 6]

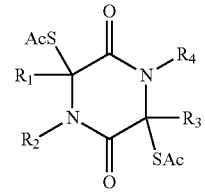

The alkali metal salt is a sodium or potassium salt, X is a halogen atom such as F, Cl, Br or I, and $R_1$ to $R_4$ are the same as those defined above.

In another aspect, the present invention provides a pharmaceutical composition for preventing or treating vascular diseases comprising an epidithiodioxopiperazine derivative represented by the following Chemical Formula 1 or a pharmaceutically acceptable salt thereof as an active ingredient; and a method for treating vascular diseases comprising administering the composition into a subject suspected of vascular diseases.

[Chemical Formula 1]

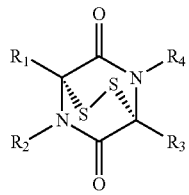

In Chemical Formula I, $R_1$ to $R_4$ are the same as those defined above.

Specifically, in Chemical Formula 1, $R_1$ to $R_4$ are each independently hydrogen, a halogen atom such as F, Cl, Br or I, a hydroxyl group, linear or branched C1 to C6 alkyl, linear or branched C1 to C6 alkoxy, linear or branched C1 to C6 hydroxyalkyl, a linear or branched C1 to C6 perfluoroalkyl group, a substituted or unsubstituted aryl group, a substituted or unsubstituted perfluoroaryl group, a substituted or unsubstituted heteroaryl group including an oxygen, nitrogen or sulfur atom in a ring as a heteroatom; or $R_1$ and $R_2$, and $R_3$ and $R_4$ each independently form a substituted or unsubstituted C3 to C6 cycloalkyl group with a carbon atom to which these are attached; or form a substituted or unsubstituted heterocyclic ring having 5 to 8 ring atoms with a carbon atom to which these are attached, and additional carbon or heteroatoms, and herein, 1 or 2 ring atoms of the heterocyclic ring may be selected from N, O and S.

The derivatives of the present invention have an intramolecular disulfide bridged bond in common. The disulfide bridged bond facilitates the introduction of the derivative into the cells, and the compound introduced into the cells exhibits an intracellular activity by being quickly reduced to two thiol groups. Therefore, the molecule needs to be designed to exclude the masking by substituents so as to facilitate the approach of a substrate to the active site. As a result, the substituents bonded to the piperazine ring of the derivative are preferably small-sized substituents so that the substituent does not stereoscopically block a disulfide bridged bond by the volume of the substituent itself or by taking up the space due to rotation, or are preferably linked to each other to form a ring so as not to rotate.

Accordingly, in the derivative represented by Chemical Formula 1, $R_1$ and $R_3$ may be hydrogen atoms, $R_2$ and $R_4$ may be each independently hydrogen, C1 to C6 alkyl, alkenyl, an alkyl group including a heteroatom of oxygen, nitrogen or sulfur in the middle of the chain, alkoxybenzyl or benzhydryl, and more preferably, $R_1$ and $R_3$ are hydrogen atoms, $R_2$ and $R_4$ may be each independently hydrogen, or C1 to C6 alkyl or alkenyl; or $R_1$ to $R_3$ are hydrogen atoms, $R_4$ may be C1 to C6 alkyl, alkenyl, an alkyl group including an oxygen, nitrogen or sulfur atom in the middle of the chain, or a substituted benzyl group such as 4-methoxybenzyl or an unsubstituted benzyl group; and $R_1$, $R_2$ and $R_4$ may be a C1 to C6 alkyl group and $R_3$ may be hydrogen, however, $R_1$ to $R_4$ are not limited thereto.

Alternatively, one or more pairs of $R_1$ and $R_2$, or $R_3$ and $R_4$ may form a substituted or unsubstituted cycloalkyl group or a heterocyclic ring.

The compound represented by Chemical Formula 1 included in the composition may be any one of compounds represented by the following Chemical Formulae 7 to 31.

[Chemical Formula 7]

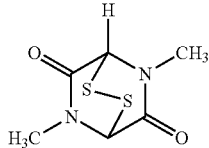

[Chemical Formula 8]

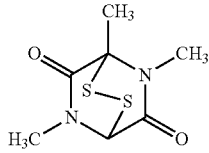

[Chemical Formula 9]

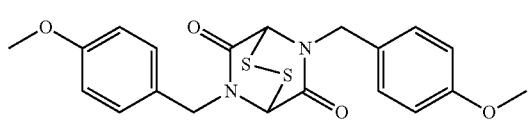

[Chemical Formula 10]

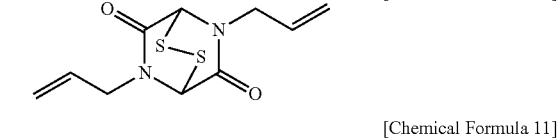

[Chemical Formula 11]

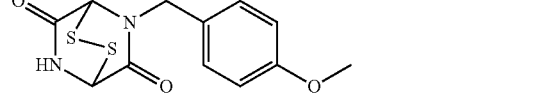

[Chemical Formula 12]

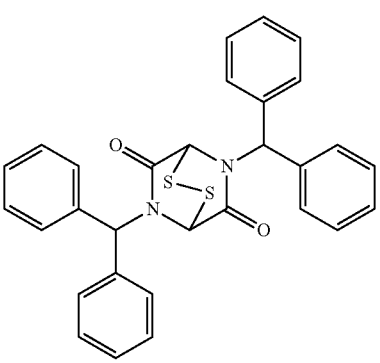

[Chemical Formula 13]

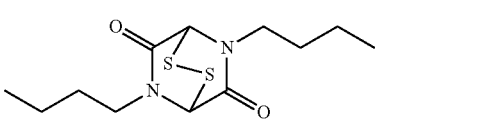

[Chemical Formula 14]

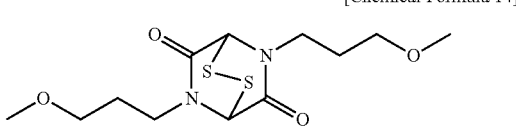

[Chemical Formula 15]
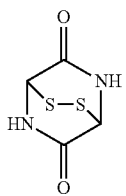
[Chemical Formula 16]
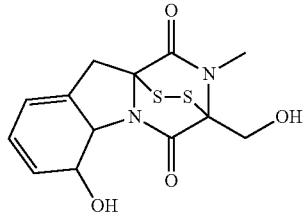
[Chemical Formula 17]
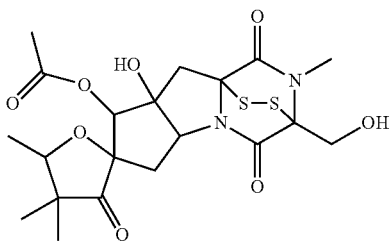
[Chemical Formula 18]
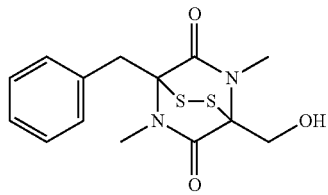
[Chemical Formula 19]
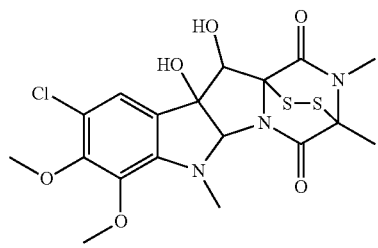
[Chemical Formula 20]
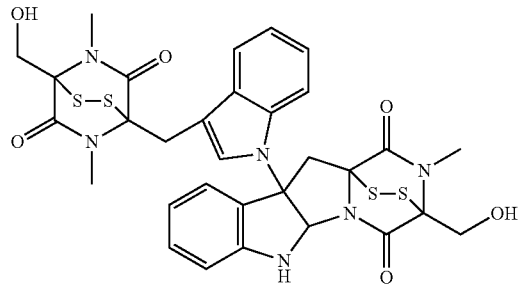
[Chemical Formula 21]
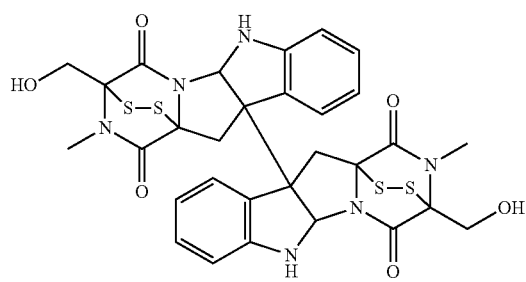
[Chemical Formula 22]
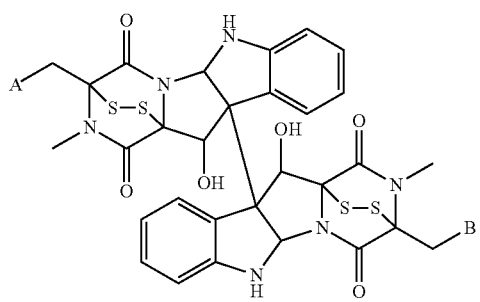
Herein, A and B are each independently hydrogen; methoxy; or a hydroxyl group.
[Chemical Formula 23]
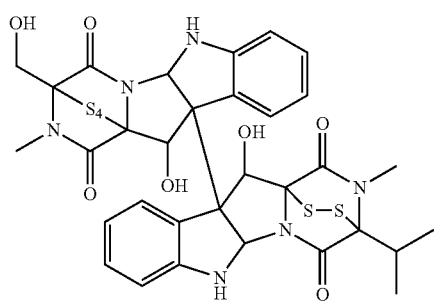
[Chemical Formula 24]
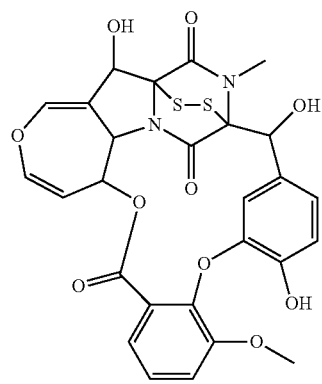

-continued

[Chemical Formula 25]

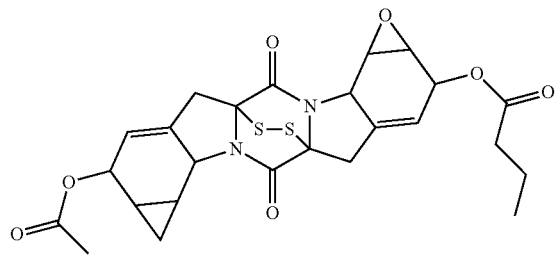

[Chemical Formula 26]

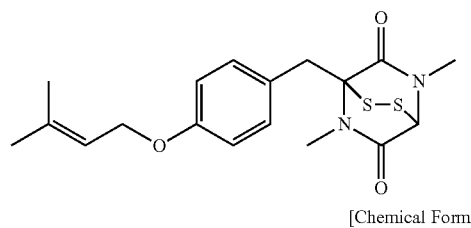

[Chemical Formula 27]

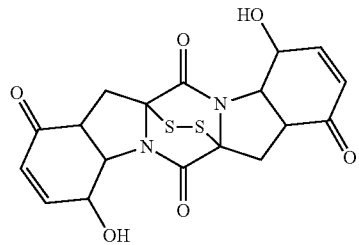

[Chemical Formula 28]

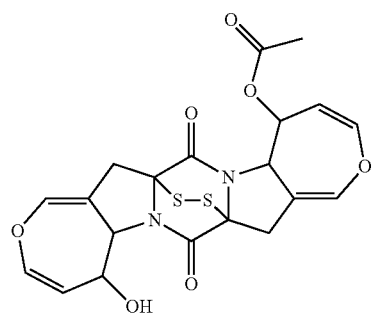

[Chemical Formula 29]

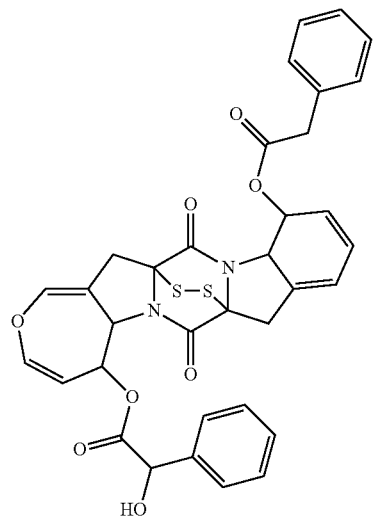

-continued

[Chemical Formula 30]

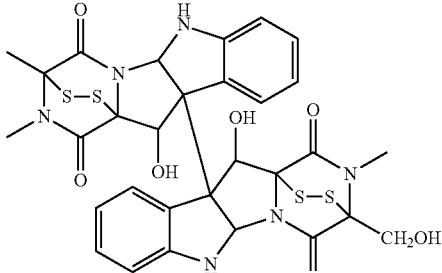

[Chemical Formula 31]

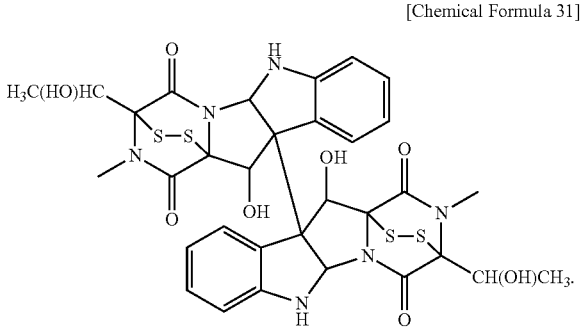

The compound of Chemical Formula 16 is a representative ETP compound called gliotoxin (GT), and may be separated from bacteria such as *Aspergillus fumigatus*, *Trichoderma virens*, *Penicillium* spp. or *Candida albicans*, a culture medium thereof, a metabolites or a secondary metabolites [Kirby and Robins, 1980, *The Biosynthesis of Mycotoxins*, New York: Academic Press; Shah and Larsen, 1991, *Mycopathologia*, 116: 203-208].

The compound of Chemical Formula 17 is an ETP compound called sirodesmin, and may be separated from bacteria such as *Leptosphaeria maculans* or *Sirodesmium diversum*, a culture medium thereof, a metabolites or a secondary metabolites [Curtis et al., 1977, *J. Chem. Soc. Perkin Trans.* 1, 180-189; Ferezou et al., 1977, *Nouv. J. Chim.*, 1: 327-334].

The compound of Chemical Formula 18 is an ETP compound called hyalodendrin, and may be separated from bacteria such as *Hyalodendron* sp., a culture medium thereof, a metabolites or a secondary metabolites [Stillwell et al., 1974, *Can. J. Microbiol.*, 20: 759-764].

The compound of Chemical Formula 19 is an ETP compound called sporidesmin A, and may be separated from bacteria such as *Pithomyces chartarum*, a culture medium thereof, a metabolites or a secondary metabolites [Kirby and Robins, 1980, *The Biosynthesis of Mycotoxins*, New York: Academic Press].

The compound of Chemical Formula 20 is an ETP compound called chetomin, and may be separated from *Chaetomium globosum* [Sekita et al., 1981, *Can. J. Microbiol.*, 27: 766-772].

The compound of Chemical Formula 21 is an ETP compound called chaetocin, and may be separated from *Chaetomium* spp. [Sekita et al., 1981, *Can. J. Microbiol.*, 27: 766-772].

The compound of Chemical Formula 22 is an ETP compound called verticillins, and may be separated from *Verticillium* spp. or *Penicillium* sp. [Byeng et al., 1999, *Nat. Prod. Lett.*, 13: 213-222; Joshi et al., 1999, *J. Nat. Prod.*, 62: 730-733; Kirby and Robins, 1980, *The Biosynthesis of*

*Mycotoxins*, New York: Sekita et al., 1981, *Can. J. Microbiol.*, 27: 766-772]. The verticillins includes all of verticillins A, verticillins 13, verticillins D, verticillins E and verticillins F.

The compound of Chemical Formula 23 is an ETP compound called leptosin, and may be separated from *Leptosphaetia* sp. [Takahashi et al., 1994, *J. Antibiot.*, 47: 1242-1249].

The compound of Chemical Formula 24 is an ETP compound called emestrin, and may be separated from *Aspergillus* spp. [Seya et al., 1986, *Chem. Pharm. Bull.*, 34: 2411-2416].

The compound of Chemical Formula 25 is an ETP compound called scabrosin, and may be separated from *Xanthoparmelia scabrosa* [Ernst-Russell et al., 1999, *Aust. J. Chem.*, 52: 279-283; Moerman et al., 2003, *Toxicol. Appl. Pharmacol.*, 190: 232-240].

The compound of Chemical Formula 26 is an ETP compound called dithiosilvatin, and may be separated from *Aspergillus silvaticus* [Kawahara et al., 1987, *J. Chem. Soc. Perkin Trans.* 1, 2099-2101].

The compound of Chemical Formula 27 is an ETP compound called epicorazine, and may be separated from *Stereum hirsutum*, *Epicoccum purpurascens* or *Epicoccum nigrum* [Deffieux et al., 1977, *Acta Christallogr.*, B33: 1474-1478; Kleinwachter et al., 2001, *J. Antibiot.*, 54: 521-525].

The compound of Chemical Formula 28 is an ETP compound called Aranotin, and may be separated from *Arachniotus aureus* or *Aspergillus terreus* [Neuss et al., 1968, *Antimicrob. Agents Chemother.*, 8: 213-219].

The compound of Chemical Formula 29 is an ETP compound called emethallicin, and may be separated from *Aspergillus heterothallicus* [Kawahara et al., 1989, *Chem. Pharm. Bull.*, 37: 2592-2595].

The compound of Chemical Formula 30 is an ETP compound called verticillins, and may be separated from *Verticillium* spp. [Byeng et al., 1999, *Nat. Prod. Lett.*, 13: 213-222; Joshi et al., 1999, *J. Nat. Prod.*, 62: 730-733; Kirby and Robins, 1980, *The Biosynthesis of Mycotoxins*, New York: Sekita et al., 1981, *Can. J. Microbiol.*, 27: 766-772].

The compound of Chemical Formula 31 may be separated from *Gliocladium catenulatum* [Byeng et al., 1999, *Nat. Prod. Lett.*, 13: 213-222; Joshi et al., 1999, *J. Nat. Prod.*, 62: 730-733; Kirby and Robins, 1980, *The Biosynthesis of Mycotoxins*, New York: Sekita et al., 1981, *Can. J. Microbiol.*, 27: 766-772].

The epidithiodioxopiperazine compound or the derivatives thereof may be separated from natural sources, acquired from natural sources and then prepared by chemical reforming, prepared from chemical systhesis by those skilled in the art referencing known preparation methods, or commercially purchased. Preferably, the epidithiodioxopiperazine compound or the derivatives thereof may be used by being separated from bacteria, a culture medium thereof, or metabolites according to methods known in the art, or prepared from syntheses using methods described in the examples of the present invention.

In the specific examples of the present invention, A1 in which all the substituents are hydrogen atoms; A2 and A3 in which 2 and 3 methyl groups are substituted, respectively; A5 in which 2 nitrogen atoms of the piperazine ring are substituted with a 2-propenyl group, and A8 in which a butyl group is bonded each show excellent activities of improving the proliferation and the migration of endothelial cells induced by VEGF while inhibiting the proliferation and the migration of vascular smooth muscle cells induced by PDGF. Meanwhile, A6 in which one methoxybenzyl group is substituted, and A9 in which two methoxypropyl groups formed with 5 elements including heteroatoms are substituted show moderate activities, and A4 in which two methoxybenzyl groups are substituted, and A7 in which two benzhydryl groups are substituted show low activities. Based on the results above, it can be inferred that the derivative substituted with relatively small substituents such as a C1 to C4 alkyl or alkenyl group shows excellent activities regardless of the number of substituents, and, the derivative having relatively large substituents has somewhat decreased activities, however, the effectiveness of the activities may be adjusted by adjusting the type and/or the number of substituents.

The epidithiodioxopiperazine derivative of the present invention may be used in the form of a pharmaceutically acceptable salt. In addition, the compounds of the present invention may be used either alone or with bonding to other pharmaceutically active compounds, or as an aggregation.

The term "pharmaceutically acceptable salt" used in the present invention means all salts having target biological and/or physiological activities of the compounds, and minimally exhibiting undesirable toxicological effects. In the present invention, the type of the salt is not limited as long as the salt maintains a diketopiperazine ring including an intramolecular disulfide bridge. As the salt, an acid addition salt formed by a pharmaceutically acceptable free acid is useful. The acid addition salt may be prepared using common methods such as dissolving a compound in an excess aqueous solution, and precipitating this salt using a water-miscible organic solvent such as methanol, ethanol, acetone or acetonitrile. An equimolar compound, and an acid or alcohol in water (for example, glycol monomethyl ether) are heated, and then the mixture may be dried by evaporation, or the precipitated salt may be sunction filtered. Herein, an inorganic acid or an organic acid may used as the free acid, and hydrochloric acid, hydrobromic acid, phosphoric acid, nitric acid, sulfuric acid, stannic acid and the like may be used as the inorganic acid, and methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid and the like may be used as the organic acid, however, the inorganic acid and the organic acid are not limited thereto.

In addition, a pharmaceutically acceptable metal salt may be prepared using a base. An alkali metal or alkaline-earth metal salt is obtained by, for example, dissolving a compound in an excess alkali metal hydroxide or alkaline-earth metal hydroxide solution, filtering the non-soluble compound salt, drying the filtrate and drying the result. Herein, preparing a sodium, potassium or calcium salt as the metal salt is pharmaceutically suitable, but the metal salt is not limited thereto. Furthermore, a silver salt corresponding to this may be obtained by reacting the alkali metal or alkaline-earth metal salt with a suitable silver salt (for example, silver nitrate).

The pharmaceutically acceptable salt of the epidithiodioxopiperazine derivatives according to the present invention includes, unless otherwise specified, all salts of acidic or basic groups that can exist. For example, the pharmaceutically acceptable salt may include a sodium, a calcium and a potassium salts of a hydroxyl group, and as other pharmaceutically acceptable salts of an amino group, hydrobromide, sulfate, hydrogen sulfate, phosphate, hydrogen phosphate, dihydrogen phosphate, acetate, succinate, citrate, tartarate, lactate, mandelate, methanesulfonate (mesylate), p-toluenesulfonate (tosylate) salt, and the like may be included, and these may be prepared using preparation methods of salts known in the art.

The pharmaceutical composition according to the present invention may be used for preventing or treating vascular diseasese arising from hypertension, an ischemic coronary artery disease such as unstable angina pectoris, angina pectoris and myocardial infarction, cerebral artery occlusion such as stroke, artherosclerosis, a pheripheral arterial occlusive disease such as a bergers disease, thromboembolism, diabetic foot lesion, venous ulcer, deep vein thrombosis, carotidal artherosclerosis, vasospasm, the hyperplasia of vascular smooth muscle and/or the loss of endothelium such as arteritis and vascular restenosis without limit. The pharmaceutical composition may be used for preventing or treating vascular restenosis arising from vascular graft, vascular cutting, artherosclerosis, intravascular lipid accumulation, hypertension, arteritis, angioplasty and the like. The reason of vascular restenosis development is not clear, however, it is known that intimal hyperplasia is caused by the abnormal migration and proliferation of vascular smooth muscle cells due to a growth factor and/or cytokine secreted from the surrounding cells as a mechanism to recover from vascular injuries due to various reasons or endothelial injuries due to devices inserted when performing angioplasty. The blood vessel includes carotid arteries, coronary arteries, pheripheral arteries, renal arteries and the like, but is not limited thereto.

The pharmaceutical composition including the epidithiodioxopiperazine derivative represented by Chemical Formula 1 or pharmaceutically acceptable salts thereof promotes the proliferation or the migration of endothelial cells while inhibiting the proliferation or the migration of vascular smooth muscle cells.

The epidithiodioxopiperazine derivative preferably has a feature mimicking the activity of 2-Cys-Prx. "PrxII (written as both peroxiredoxin II or Prx2)" is one of peroxidase 2-Cys-Prx reducing intracellular hydrogen peroxide, and plays a role to suppress cellular signaling amplification through suppressing phosphorylation that occurs site-specifically in PDGFRβ-PCLγ1 by reducing the hydrogen peroxide produced by PDGF in vascular smooth muscle cells. Through a mechanism such as this, the PrxII has an activity to inhibit the migration and the proliferation of smooth muscle cells in injured blood vessels and suppress intimal hyperplasia (M. H. Choi et al., 2005, *Nature*, 435: 347). Meanwhile, it has been reported that PrxII activates VEGF-induced signaling by protecting VEGFR2 from oxidative deactivation in endothelial cells (D. H. Kang et al., 2011, *Mol. Cell.*, 44: 656). The inventors of the present invention have domonstrated that the epidithiodioxopiperazine compound or its derivatives according to the present invention may replace PrxII in the cellular fuction using a cellular and vascular injured animal model in which PrxII is knocked out by injecting PrxII siRNA.

According to one aspect of the present invention, it is demonstrated that gliotoxin, chaetocin, chetomin and compounds represented by Chemical Formulae 7 to 15, which are representative compounds belonging to the compound represented by Chemical Formula 1, that is, compounds having an epidithiodioxopiperazine structure may mimic the intracellular 2-Cys-Prx activity and have improved ability to introduce into the cells, and additionally, it is demonstrated that these compounds can promote the migration and the proliferation of VEGF-induced endothelial cells while inhibiting the migration and the proliferation of PDGF-induced vascular smooth muscle cells. Accordingly, other compounds represented by Chemical Formula 1 are also effective in treating vascular diseases, particularly, vascular restenosis by promoting the migration and the proliferation of endothelial cells, and inhibiting the migration and the proliferation of vascular smooth muscle cells, since the compounds share the epidithiodioxopiperazine structure.

The composition according to the present invention may further include proper carriers, diluting agents and diluents commonly used for the preparation of pharmaceutical compositions. The composition is sterilized or aseptic, may be water, a buffer, an isotonic agent and the like, and the solution is sterilized or aseptic, or may include other ingredients known to those skilled in the art, which do not cause allergies or other harmful reactions when applied to animals or humans.

The term "pharmaceutically acceptable carrier" used in the present invention includes all random solvents, dispersive media, coating materials, antimicrobial agents, antifungal agents and isotonic agents and the like. Using the media and the formulations as pharmaceutically active materials is well known in the related art. In addition to common media or formulations non-miscible with active ingredients, the use of the media and the formulations described above is considered in therapeutic compositions. In addition, supplementary active ingredients may be mixed with the composition described above.

The composition may be prepared as formulations such as liquids, emulsions, suspensions or creams, or may be used for non-oral administration. The amount of the composition used may be amounts commonly used for preventing or treating vascular diseases, and is preferably different depending on the age, the gender and the condition of patients, in vivo absorbance of active substances, inactivation rate and drugs used in combination.

In the present invention, the term "prevention" means all actions that suppress vascular diseases or delay the outbreak of the diseases by the administration of the pharmaceutical composition, and the term "treatment" means all actions that enable the symptoms of vascular diseases to improve or change for the better by the administration of the pharmaceutical composition.

In the present invention, the term "subject" means all animals including human beings developed with or having a possibility of developing vascular diseases, and the vascular disease may be effectively prevented or treated by administering the pharmaceutical composition of the present invention into an entity. In addition, the pharmaceutical composition of the present invention may be administered in combination with known therapeutic agents for vascular diseases.

The pharmaceutical composition of the present invention is administered with a therapeutically effective dose. The term "therapeutically effective dose" means an amount sufficient to treat diseases in a reasonable benefit/risk ratio applicable to medical treatments and not to cause side effects, and the level of the effective dose may be readily determined by those skilled in the art depending on the factors including the gender, age, weight and health condition of patients, severity of the disease, the activity of drugs, the sensitivity to drugs, administration methods, administration time, administration paths and excretion rates, treatment period and drugs mixed or simultaneously used, and other factors well-known in the field of medicine.

Examples of known therapeutic agents that can be used in combination with the pharmaceutical composition of the present invention include paclitaxel, silorimus or the like.

Therapheutically effective doses of known therapeutic agents are known in the related art, and an attending physician may adjust the amount considering various conditions such as the level of symptoms and coadministration with the composition of the present invention. By coadministering known therapeutic agents as described above, the side effects of the known therapeutic agents may be reduced by the composition of the present invention, and synergic curative effects can be expected as well. These known therapeutic agents may be administered simultaneously as a combination drug, or consecutively at time intevals with the composition of the present invention.

The term "administration" in the present invention means introducing a prescribed material to a patient using proper methods, and the composition may be administered via any general path as long as the composition reaches a target tissue. Although not limited thereto, the administration method is preferably non-oral administration, and more preferably, local administration to lesions. For local administration of drugs, double balloon catheters, dispatches or microporous balloons and the like may be used, and particularly, stents or sustained microparticles may be used for a long-term drug delivery. Most preferably, the composition of the present invention may be directly administered to the area of stenosis by applying the composition inside a stent.

In addition, the present invention provides a drug delivery device for local administration including the pharmaceutical composition for preventing or treating vascular diseases. The drug delivery device for local administration may include double balloon catheters, dispatches, microporous balloons, stents and the like, but is not limited thereto, and is preferably a stent.

The term "stent" in the present invention means a general device for endoluminal application as described above such as intravascular application, and means a cylindrical medical material normalizing a blood flow by being inserted to a narrowed or clogged vascular area under fluoroscopy without surgical laparotomy when the blood flow is disabled due to the development of diseases at a location to have a smooth blood flow. For example, a vascular stent is described in "Textbook of Interventional Cardiology" (Saunders Company, 1994) written by Eric J. Topol. Preferably the stent is a sustained drug-releasing stent.

As the method of coating the pharmaceutical composition of the present invention to the stent, common coating methods known to those skilled in the art may be applied, and examples thereof include a dip-coated method and a polymer-coated method, the dip-coated method is the simplest coating method, and biological effects of the drug itself are readily observed since only the pharmaceutical composition is coated, however, the method is not limited thereto. Preferably, the stent of the present invention may be prepared by coating the composition on a drug-releasing stent after being mixed with a polymer material so that the composition according to the present invention is slowly released. The polymer material that can be used as a drug-releasing stent is widely known in the art, and examples thereof include polyurethane, polyethylene terephthalate, PLLA-poly-glycolic acid copolymer (PLGA), polycarprolactone, poly-(hydroxybutyrate/hydroxyvalerate) copolymer, polyvinylpyrrolidone, polytetrafluoroethylene, poly(2-hydroxyethylmethacrylate), poly(etherurethane urea), silicone, acryl, epoxide, polyester, urethane, pyrene, a polyphosphazine polymer, a fluoro polymer, polyamide, polyolefin and a mixture thereof, but are not limited thereto.

The stent may be formed with one or more materials selected from the group consisting of polysaccharide, heparin, gelatin, collagen, alginate, hyaluronic acid, alginic acid, carrageenan, chondroitin, pectin, chitosan, and derivatives and copolymers thereof, or may be further coated with an antithrombotic layer including these. These materials may be properly combined to a biocompatible topcoat as described in US Patent Application Laid-Open Publication No. US 2006/0083772. The method for forming a stent from the mixture of a polymer and a drug compound is disclosed in Blindt et al., 1999, *Int. J. Artif. Organs*, 22: 843.

In another aspect, the present invention provides a pharmaceutical composition for inhibiting melanoma metastasis comprising the epidithiodioxopiperazine derivative represented by Chemical Formula 1 or pharmaceutically acceptable salts thereof as an active ingredient.

In addition, the present invention provides a method for inhibiting melanoma metastasis comprising administering the pharmaceutical composition into a subject in need of the composition.

The compound represented by Chemical Formula 1 included in the composition may be any one of compounds represented by Chemical Formulae 7 to 31.

The "melanoma" means malignant tumors of melanocyte producing melanin, a dark pigment, and is also referred to as malignant melanoma. The melanocyte determines a skin color, and usually appears on the skin, but may also appear on other body parts including intestine and eyes. Therefore, melanoma may occur in any body part in which melanocyte is distributed. Melanoma is not a general disease compared to other skin cancers, but is a much more dangerous disease since early detection is difficult, and most (75%) of the cause of a skin cancer-relating death is due to melanoma. Metastatic melanoma may cause non-specific symptoms such as the loss of apetite, nausea and fatigue. Although relatively rare, melanoma sometimes metastasizes at an early stage. Brain metastasis is most universally observed in metastatic melanoma patients. In addition, melanoma may metastasize to liver, bone, abdomen or even to lymph nodes at a long distance.

The inventors of the present invention have demonstrated that PrxII is involved in melanoma metastasis through specific examples. Specifically, it is identified that the level of intracellular hydrogen peroxide is high in cell lines in which the expression level of PrxII in the melanoma cell line is low (SK5 and SK28). Furthermore, it is identified that these cell lines have high propliferative and migratory activities compared to melanoma cell lines expressing PrxII (A375 and G361). Meanwhile, when the PrxII expression increases in the melanoma cell line hypoexpressing the PrxII, it is identified that the proliferation and the migration are reduced. Furthermore, when the PrxII is selectively knocked down in the melanoma cell line expressing the PrxII using siRNA, it is identified that the proliferation and the migration are enhanced. In addition, using a PrxII knockdown mouse model, the PrxII is identified to be involved in melanoma metastasis in vivo (Experimental Example 9 (1)). As described above, PrxII is one type of 2-Cys-Prx, and based on the idea that the epidithiodioxopiperazine derivative according to the present invention may mimic the activity of 2-Cys-Prx such as PrxII in the cells, it is identified that the metastatic potential of melanoma may be inhibited by treating with gliotoxin (GT), chaetocin and chetomin, which is one type of epidithiodioxopiperazine derivatives separated from fungal metabolites including an intramolecular disulfide bridged bond structure identified to exhibit the activity in the derivatives of the present invention (Experimental Example 9 (2) and (3)). As a result, the epidithiodioxopiperazine derivative according to the present invention may effectively inhibit the metastatis of melanoma caused by PrxII deficiency or inactivation by mimicking the PrxII activity in the cells.

In addition, the present invention provides a method for preparing a preventive or therapeutic agent for vascular restenosis including identifying whether the epidithiodioxopiperazine (ETP) compound including one or more epidithiodioxopiperazine rings represented by Chemical Formula 47 exhibits a 2-Cys-peroxiredoxin (2-Cys-Prx) activity; and producing the compound identified to exhibit the 2-Cys-peroxiredoxin (2-Cys-Prx) activity in the above step.

[Chemical Formula 47]

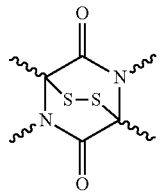

In addition, the present invention provides a method for screening a preventive or therapeutic agent for vascular restenosis including the steps of (a) identifying whether the compound including one or more epidithiodioxopiperazine rings represented by Chemical Formula 47 exhibits a 2-Cys-peroxiredoxin (2-Cys-Prx) activity; and (b) determining the compound as a preventive or therpeutic agent for vascular restenosis when a NADPH oxidation reaction or $H_2O_2$ reduction reaction occurs.

In Step (a), the identification of whether the compound exhibits a 2-Cys-peroxiredoxin (2-Cys-Prx) activity may be carried out by identifying whether the NADPH oxidation reaction or $H_2O_2$ reduction reaction occurs when the compound including one or more epidithiodioxopiperazine rings represented by Chemical Formula 47 is mixed and reacted with thioredoxin (Trx), thioredoxin reductase (TR), NADPH, a buffer solution and $H_2O_2$; and determining that the compound exhibits a 2-Cys-peroxiredoxin (2-Cys-Prx) activity when the NADPH oxidation reaction or $H_2O_2$ reduction reaction occurs.

The above compound including one or more epidithiodioxopiperazine rings represented by Chemical Formula 47 may have more than 1, 2, 3 or 4 epidithiodioxopiperazine rings, but is not limited thereto.

Specifically, an experimental group is prepared by first reacting the candidate compound including epidithiodioxopiperazine rings with Trx, TR, NADPH and EDTA in a buffer solution, then mixing with $H_2O_2$ to carry out an oxidation reaction, and a control group is prepared by carrying out the same reaction without the sample, and then each group may be compared by monitoring the absorbance decrease at 340 nm. Herein, the control group exhibits constant absorbance while absorbance decrease with time is observed when the candidate compound exhibiting the 2-Cys-Prx activity is included, and the activity is proportional to the degree of absorbance decrease. Accordingly, by performing the above steps, the candidate compound including epidithiodioxopiperazine rings for which the absorbance decrease is observed may be determined as a material having activities for preventing or treating vascular restenosis. The Trx and TR may be derived from yeast, humans or rats, and preferably derived from yeast. The identification of whether the compound exhibits a 2-Cys-peroxiredoxin (2-Cys-Prx) activity may be carried out according to a method described in Korean Patent Application Laid-Open Publication No. 10-2006-0020140, and the contents of the patent are included in the present specification as a reference.

Advantageous Effects

The present invention relates to a series of novel epidithiodioxopiperazine derivatives, and the derivative includes an intramolecular disulfide bridged bond which thereby has improved intracellular permeability, and is quickly reduced to a compound having 2 thiol groups in the cells, thereby suppressing intimal hyperplasia by mimicking the function of PrxII isoform particularly among 2-Cys-Prx, and inhibiting the migration and the proliferation of PDGF-induced vascular smooth muscle cells while improving reendothelialization by promoting the migration and the proliferation of VEGF-induced endothelial cells. Accordingly, the epidithiodioxopiperazine derivatives according to the present invention are useful as pharmaceutical compositions for preventing or treating vascular diseases. In addition, the derivatives are useful in treating melanoma since the derivatives may inhibit the metastatis of melanoma through mimicking an intracellular PrxII activity.

HASMCs (a) and HAECs (b) are serum-starved in a basal medium containing 0.5% FBS, then pretreated for 2 hours with the indicated concentrations of GT or chaetocin, and treated for 10 minutes with PDGF or VEGF. As the Data, the presentage of the superoxide amount in stimulated cells versus unstimulated cells is presented as mean±standard error (n=3, *p<0.05, **p<0.001).

Figure 23:
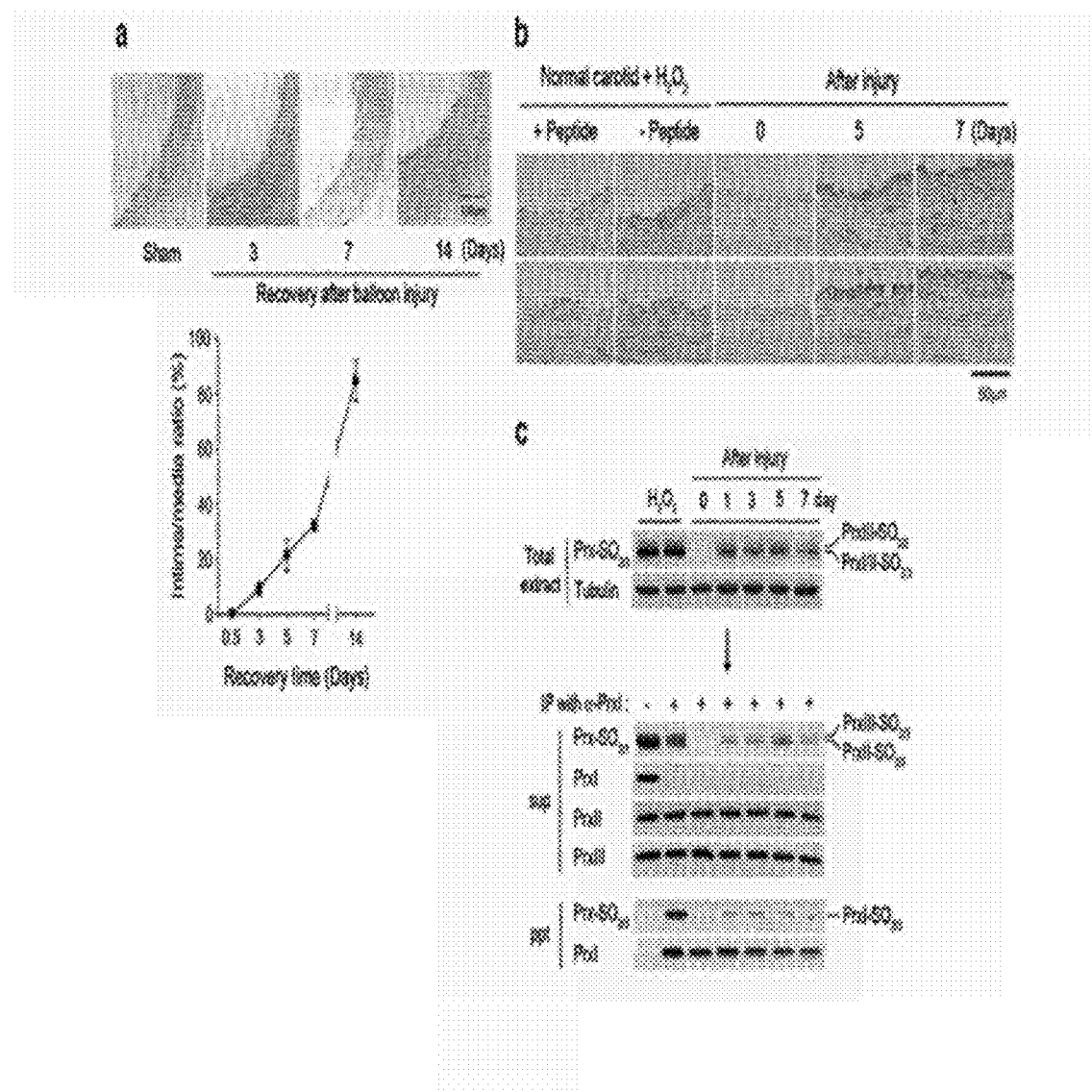

FIG. 23 is a diagram showing the effects of GT on suppressing vascular intimal hyperplasia and promoting reendothelialization in balloon-injured carotid arteries. (a) is representative HE-stained images showing intimal hyperplasia according to time during a recovery period in balloon-injured carotid arteries. The ratio of intima versus media measured from HE-stained carotid artery sections is presented as mean±standard error (n=4 per group). (b) indicates overoxidation of 2-Cys-Prx in carotid arterial vessels induced by balloon injury, and immunohistochemistry is performed using an anti-overoxidized 2-Cys-Prx (Prx-SO$_{2/3}$) antibody. For a positive control, normal carotid arterial vessels treated with a hydrogen peroxide solution for 10 minutes are stained. The blocking antigenic peptide eliminates the immune-positive signal. The representative DAB-stained images are shown from 4 independent samples. (c) shows the result of immunoblot analysis for intracellular 2-Cys-Prx overoxidation using injured carotid arterial extracts. For comparison, extracts from normal carotid arterial vessels treated with hydrogen peroxide are loaded together.

Figure 24:
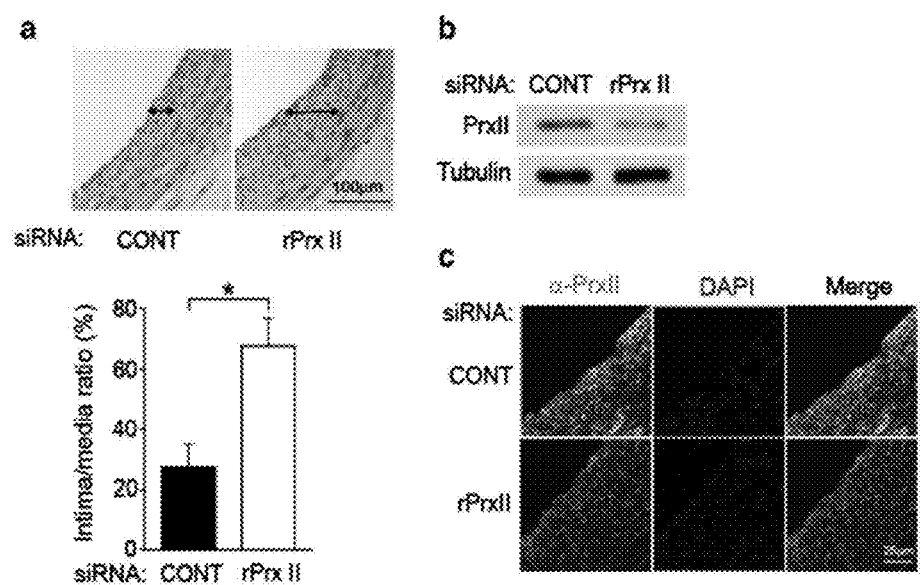

FIG. 24 is a diagram showing the effects of in vivo injection of PrxII siRNA on promoting intimal hyperplasia in balloon-injured carotid arteries. (a) shows the effects of PrxII knockdown for intimal hyperplasia induced by balloon injury as representative HE-stained images. The ratio of intima versus media measured from HE-stained carotid artery sections is presented as mean±standard error (n=7 per group, *p<0.01). (b) is the result of western blotting of injured carotid arterial extracts for rat PrxII. (c) is the result of immunofluorescence staining of rat PrxII in injured carotid artery tissue sections. This represents intrinsic PrxII knockdown by siRNA injection in balloon-injured carotid arteries.

Figure 25:
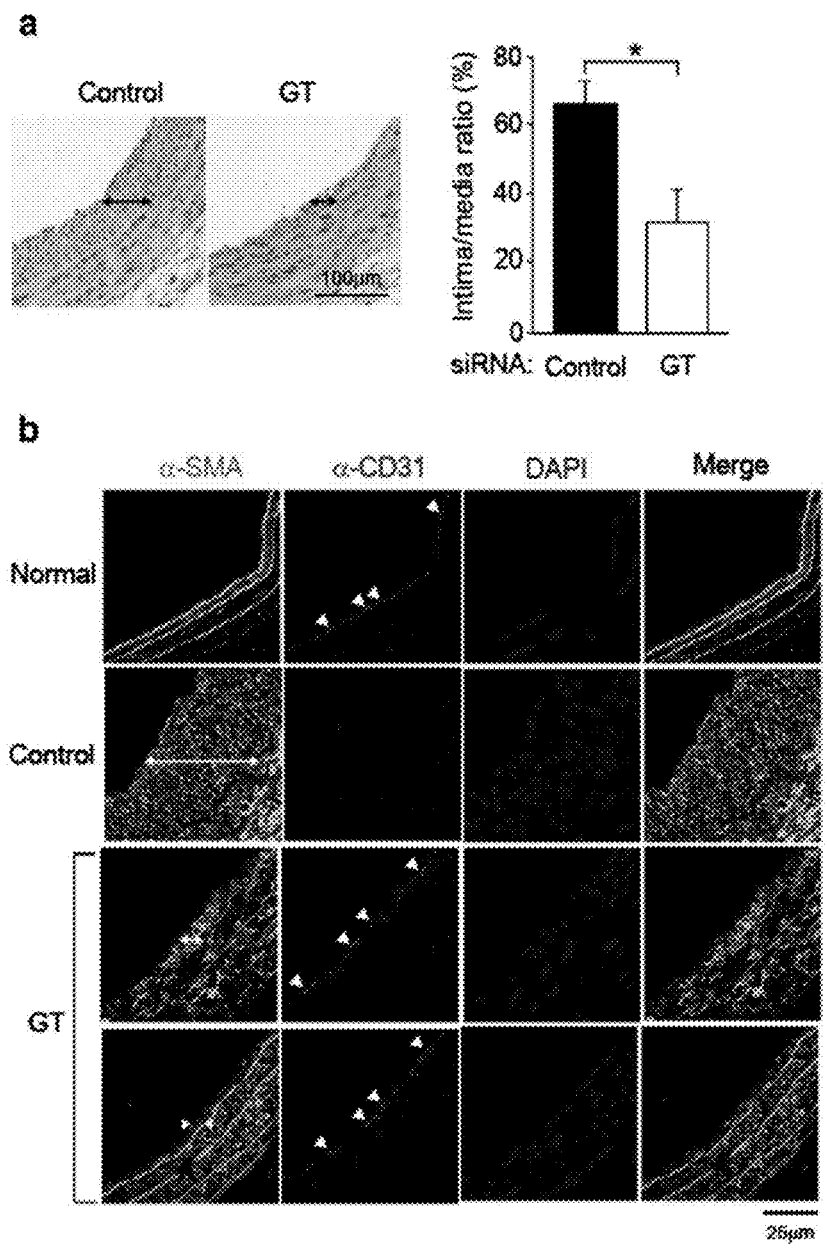

FIG. 25 is a diagram showing the effects of GT on intimal hyperplasia and endothelial layer regeneration in balloon injured rat carotid arteries. (a) is a diagram showing the vascular intima of balloon injured rat carotid arteries after treated with a control group and GT. Representative HE-stained images that are obtained by treating with DMSO and GT each and then incubating for 30 minutes are shown. The arrow indicates the thickened vascular intimal layer. The ratio of intima versus media measured from HE-stained carotid artery samples is presented as mean±standard error (n=9 per group, *p<0.01). (b) is a diagram showing the result of immunofluorescence staining of smooth muscle α-actin (SMA) and CD31 (n=3). Normal carotid arterial vessels show a typical endothelial monolayer (arrow). DAPI staining shows nuclei.

Figure 26:
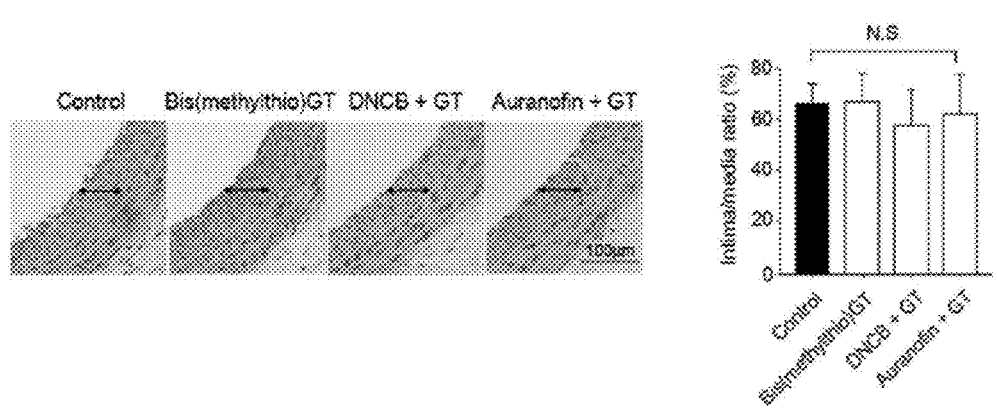

FIG. 26 is a diagram showing HE-stained images according to the treatment with bis-(methylthio)GT alone or GT+TR inhibitor (DNCB, auranofin) for intimal hyperplasia induced by balloon injury.

Figure 27:
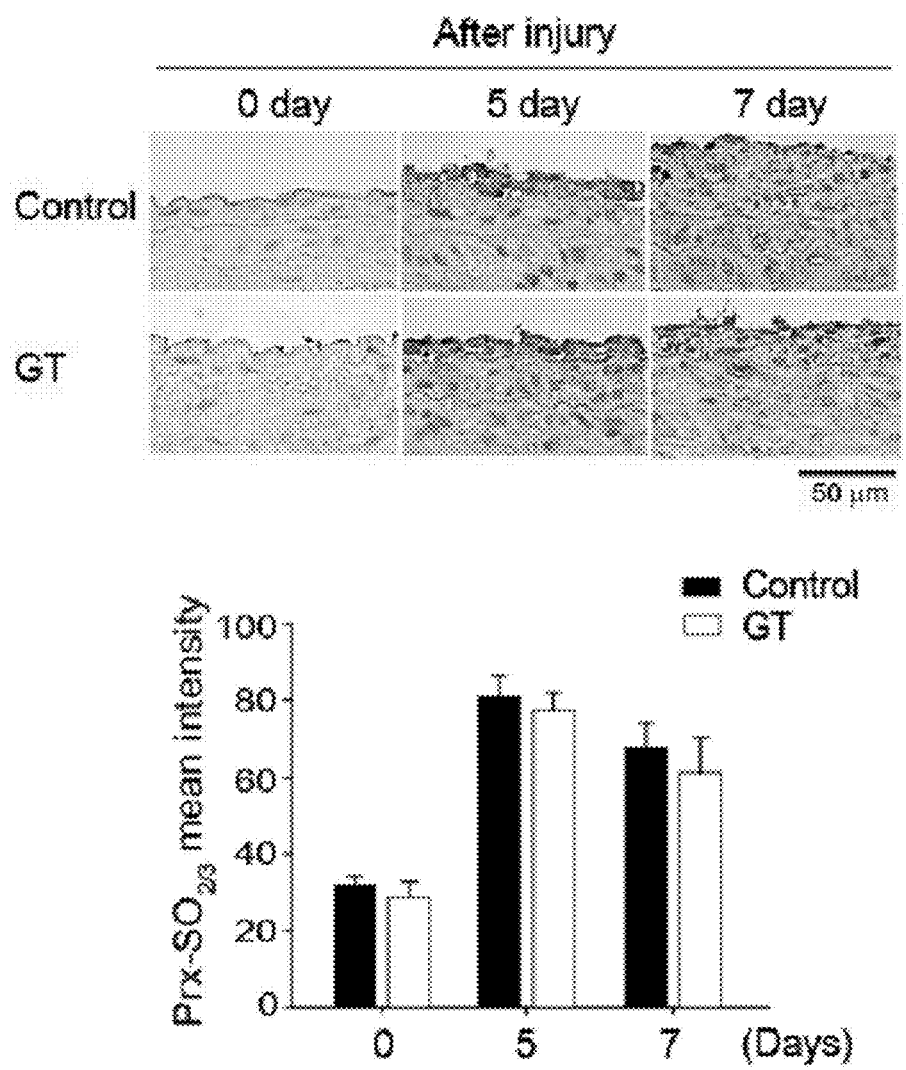

FIG. 27 is a diagram showing the result of immunohistochemistry staining verifying the effects of GT on 2-Cys-Prx overoxidation.

Figure 28:
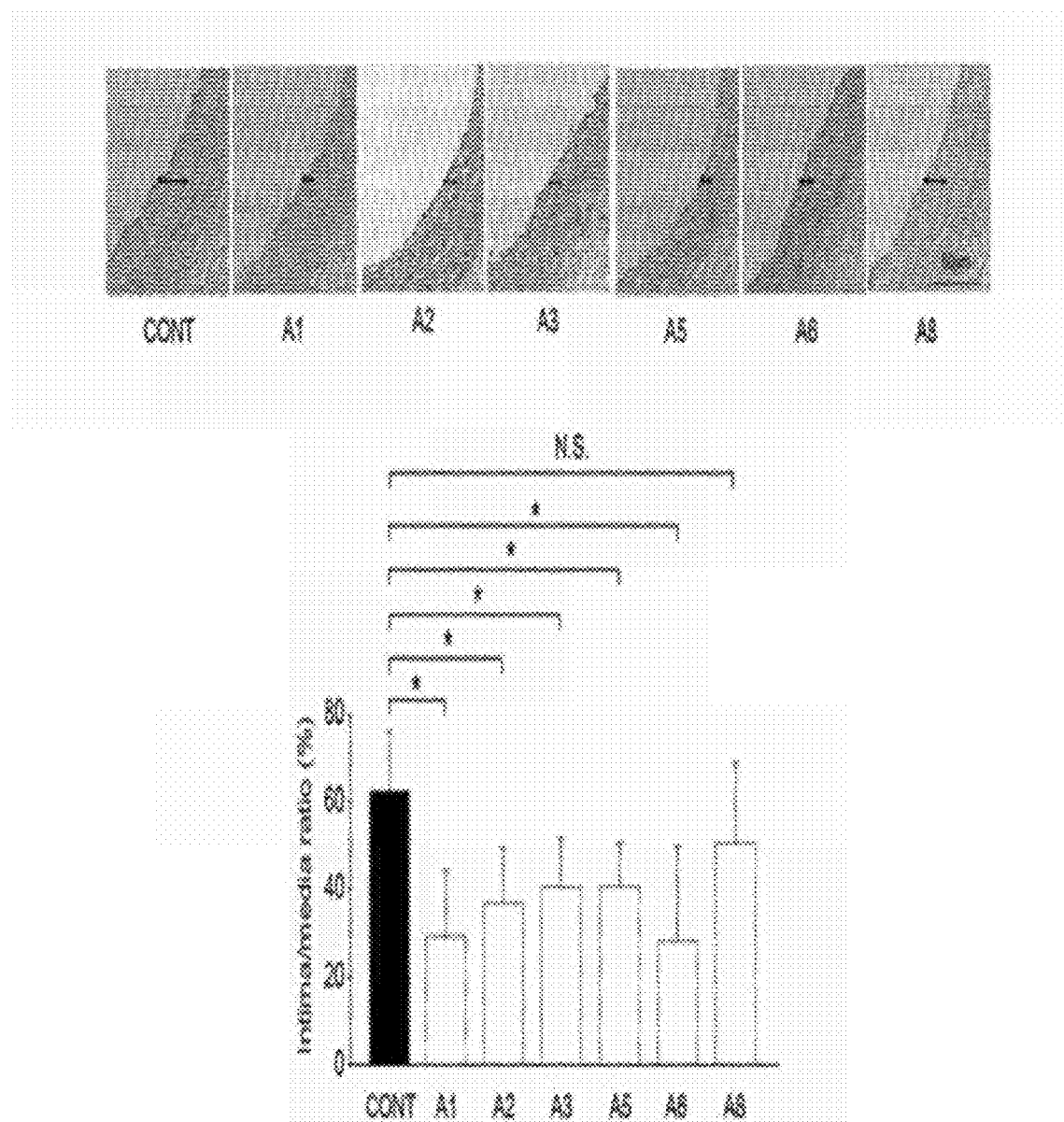

FIG. 28 is a diagram showing that A1 to A3, A5, A6 and A8, which are ETP derivatives according to the present invention, inhibit the proliferation of neointimal smooth muscle cells. Representative H&E staining images are shown, and the data shown in the graph are the ratio of intima versus media measured from HE-stained carotid artery sections and are presented as mean±standard error (*p<0.01). N.S. means not significant.

Figure 29:
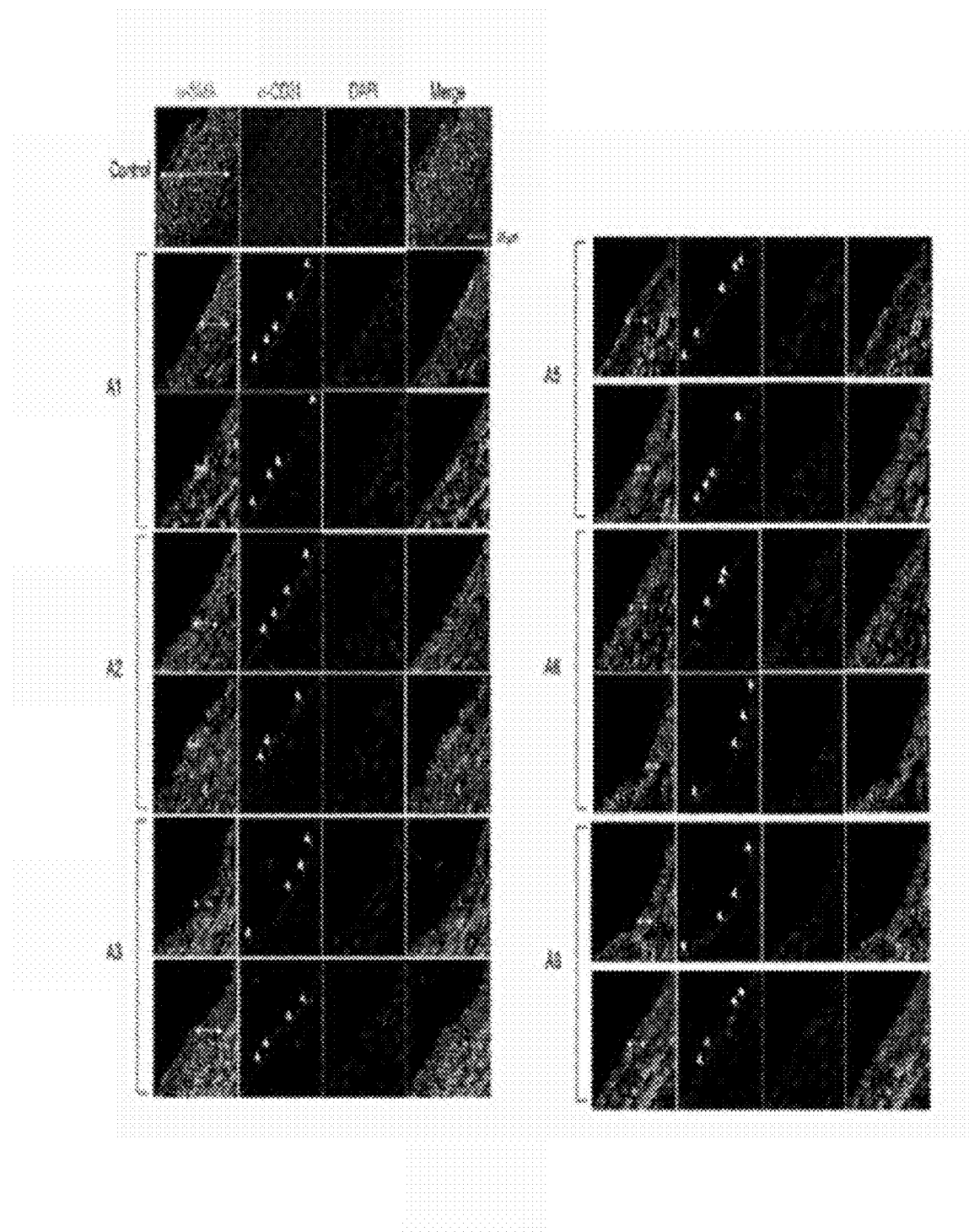

FIG. 29 is a diagram showing that reendothelialization is induced when a balloon injured carotid artery model is treated with A1 to A3, A5, A6 and A8 that are ETP derivatives according to the present invention. Costaining of CD31 and smooth muscle α-actin (SMA) is carried out in injured carotid arteries treated with DMSO or the ETP derivatives, and the corresponding parts are indicated. The arrow indicates the thickened neointima area, and the arrowhead indicates a typical endothelial monolayer of carotid arteries treated with the ETP derivatives. Nuclei are stained with DAPI. Representative images from 2 independent experiments are shown.

Figure 30:
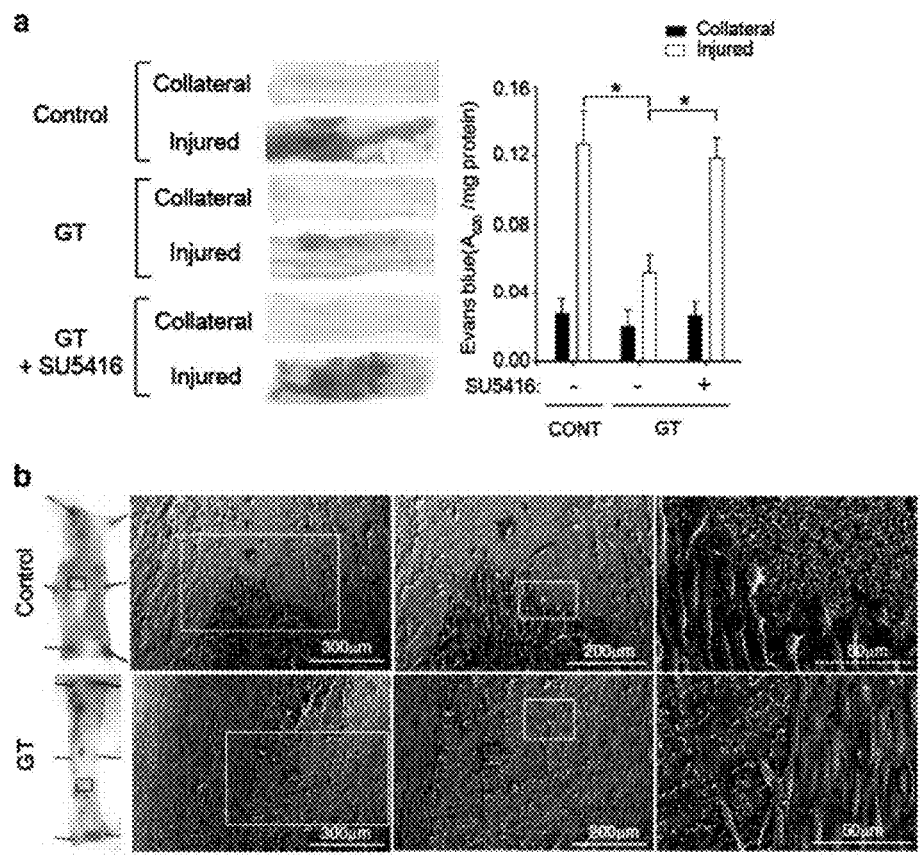

FIG. 30 is a diagram showing the effects of GT on vascular permeability and luminal surface status in balloon injured rat carotid arteries. (a) shows the extent of Evans blue inflow within balloon-injured rat carotid arterial vessels treated with a control group and GT. On the left side, representative images are shown, and in the graph on the right side, the Evans blue inflowed into the blood vessel is extracted and the absorbance at 620 nm is presented as mean±standard error (n=7 per group, *p<0.01). (b) is a scanning electron microscopic examination result of the luminal surface of balloon-injured rat carotid arterial vessels treated with a control group and GT. 3 independent experiments are carried out, and representative zoom-in images are shown.

Figure 31:
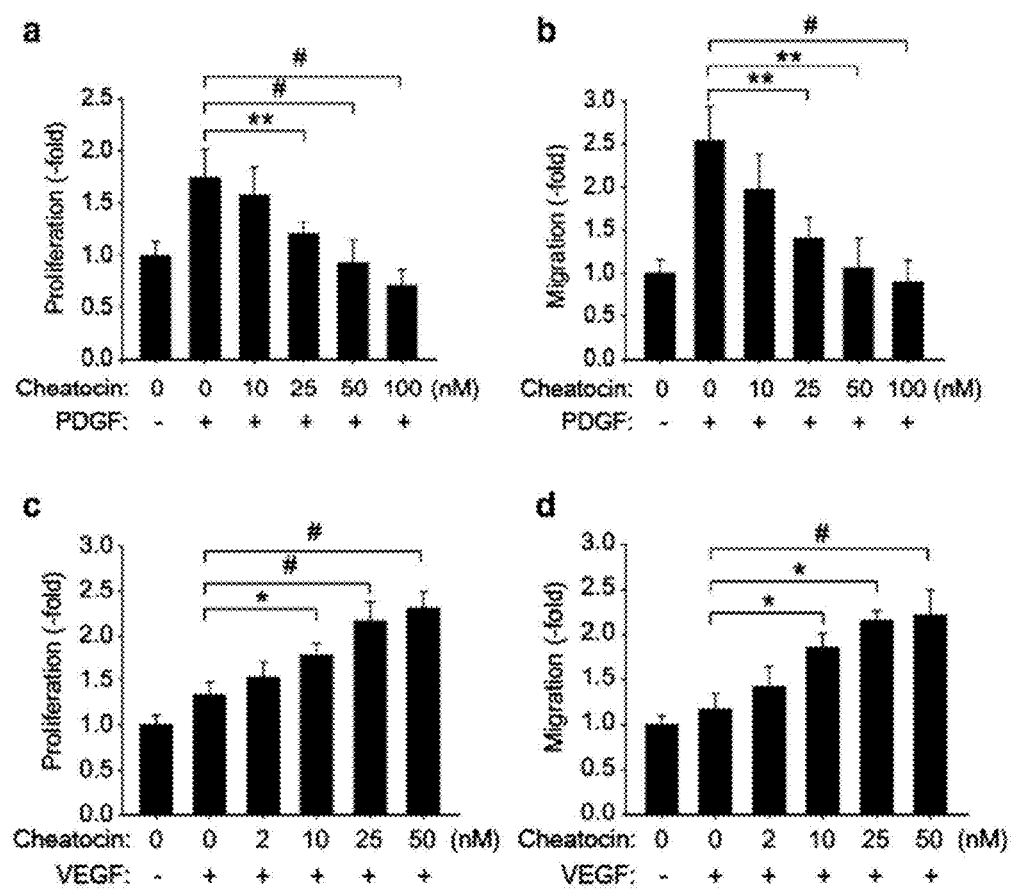

FIG. 31 is a diagram showing the effects of chaetocin treatment on cell proliferation and migration. PrxII knocked down HASMCs ((a) and (b)) and HAECs ((c) and (d)) are pretreated with chaetocin for 2 hours, and stimulated with PDFG or VEGF for 24 hours. The fold-increase is presented as mean±standard error in the graph (n=3, *p<0.01, **p<0.005, #p<0.001).

Figure 32:
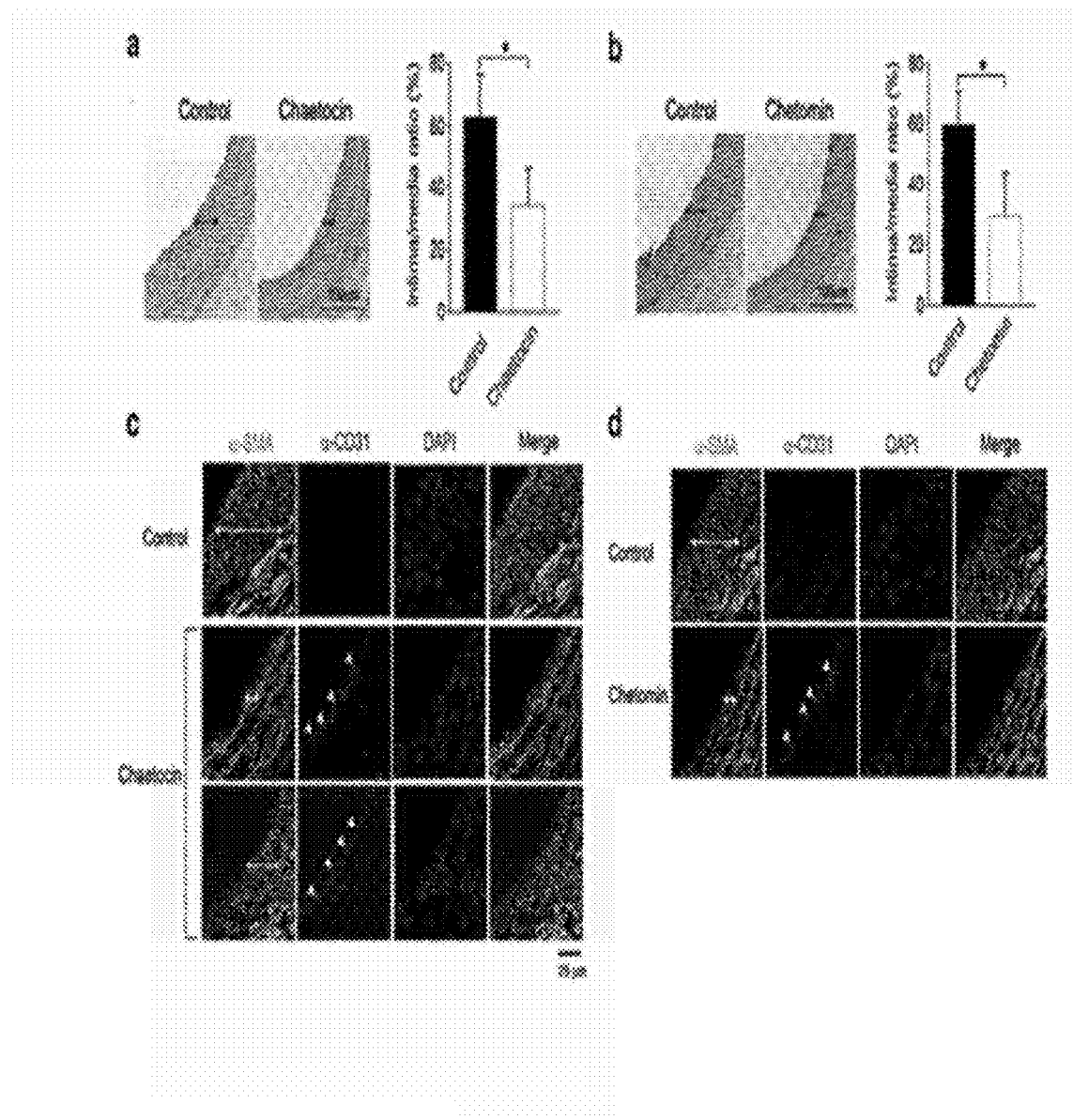

FIG. 32 is a diagram showing the effects of chaetocin and chetomin on intimal hyperplasia induced by balloon injury. The balloon injured rat carotid arteries are incubated with chaetocin or chetomin for 30 minutes. DMSO is used as a control group, and representative HE-stained images ((a) and (b)) are shown. The arrowhead indicates the thickened vascular intimal layer. The ratio of intima versus media measured from HE-stained carotid artery samples are presented as mean±standard error (n=9 per group, *p<0.01). (c) and (d) show the results of immunofluorescence staining of smooth muscle α-actin (SMA) and CD31. The arrow indicates an endothelial monolayer.

Figure 33:
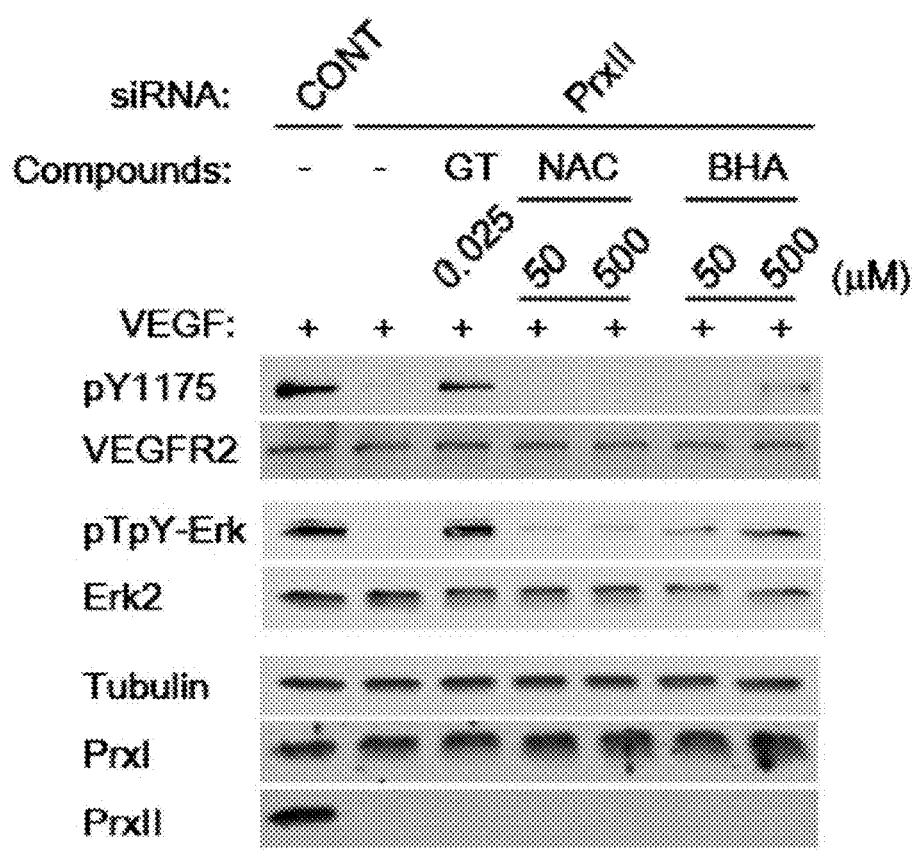

FIG. 33 is a diagram showing the effects of various antioxidant compounds on VEGF signaling in HAECs. PrxII siRNA is injected to VEC, and the result is pretreated with increasing concentrations of the indicated compounds (N-acetylcystein; NAC, butylated hydroxyanisole; BHA) for 2 hours. The cells are treated with VEGF for 10 minutes, and then analyzed by immunoblotting.

Figure 34:
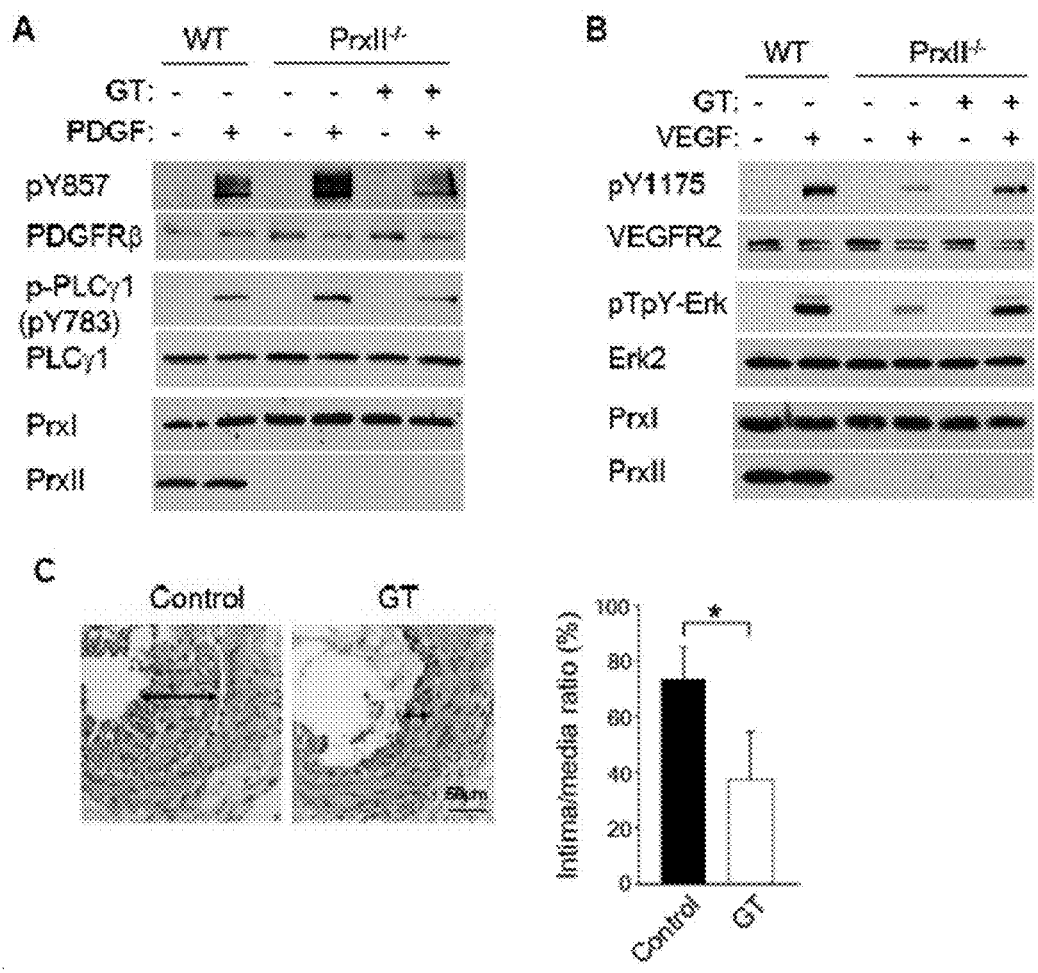

FIG. 34 is a diagram showing the western blot results verifying the effects of GT on PDGF- and VEGF-dependent tyrosine phosphorylation in PrxII-deficient vascular cells and ((a), (b)), and the HE-staining results verifying the effects of GT on ligation-induced vascular intimal hyperplasia in PrxII-deficient mice.

Figure 35:
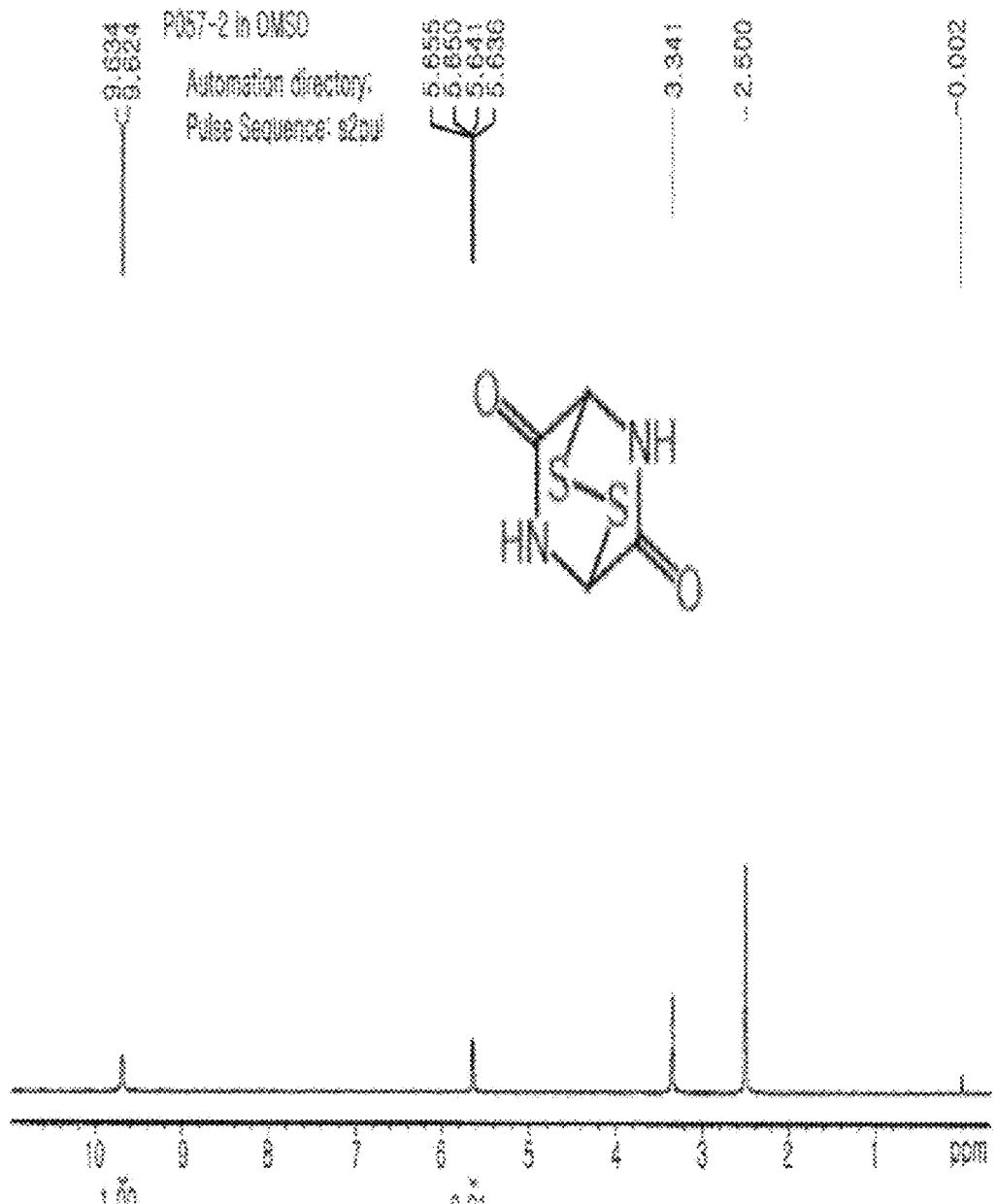

FIG. 35 is a diagram showing a $^1$H NMR spectrum of Compound A1 (Chemical Formula 15) according to the present invention.

Figure 36:
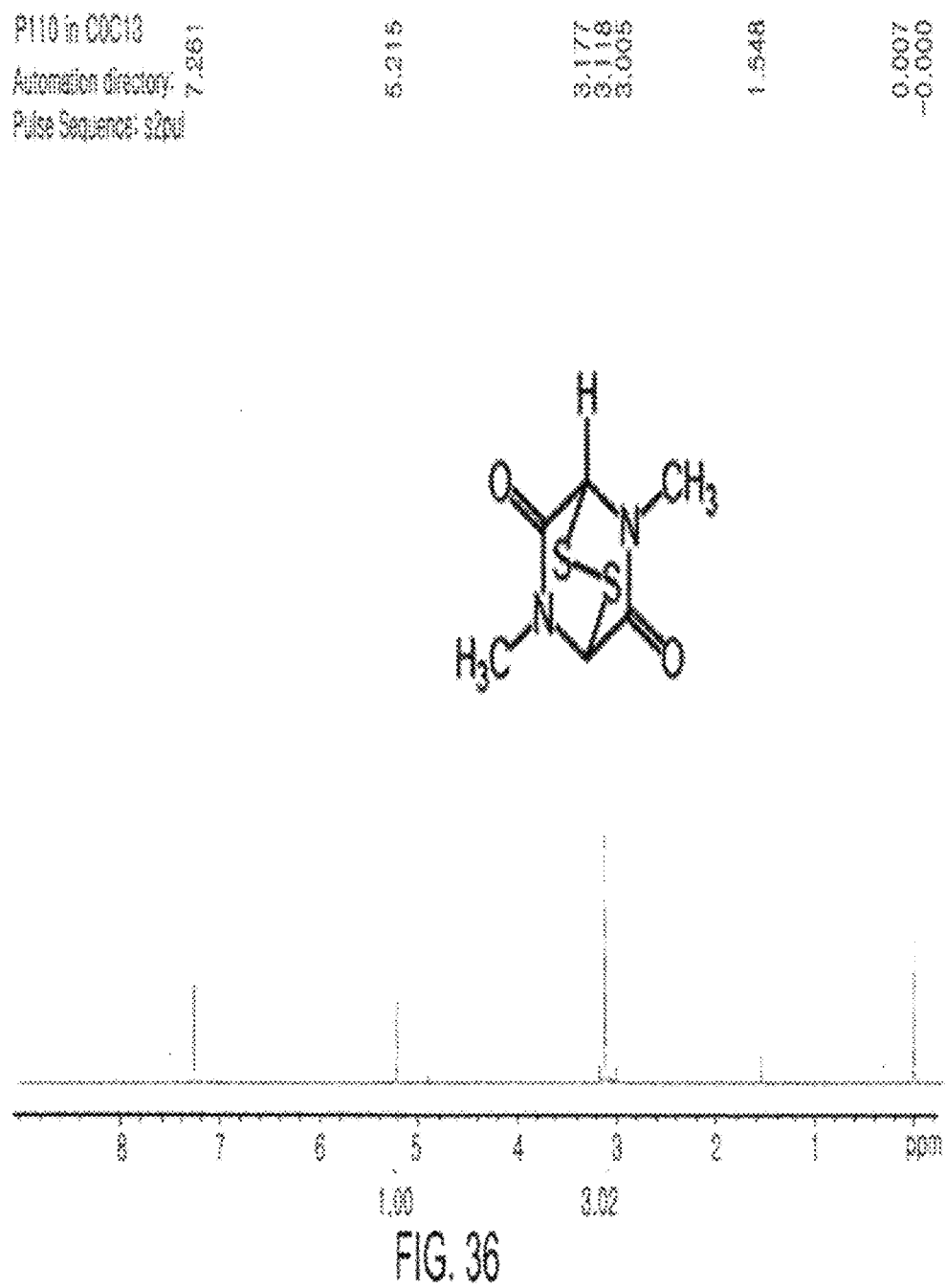

FIG. 36 is a diagram showing a $^1$H NMR spectrum of Compound A2 (Chemical Formula 7) according to the present invention.

Figure 37:
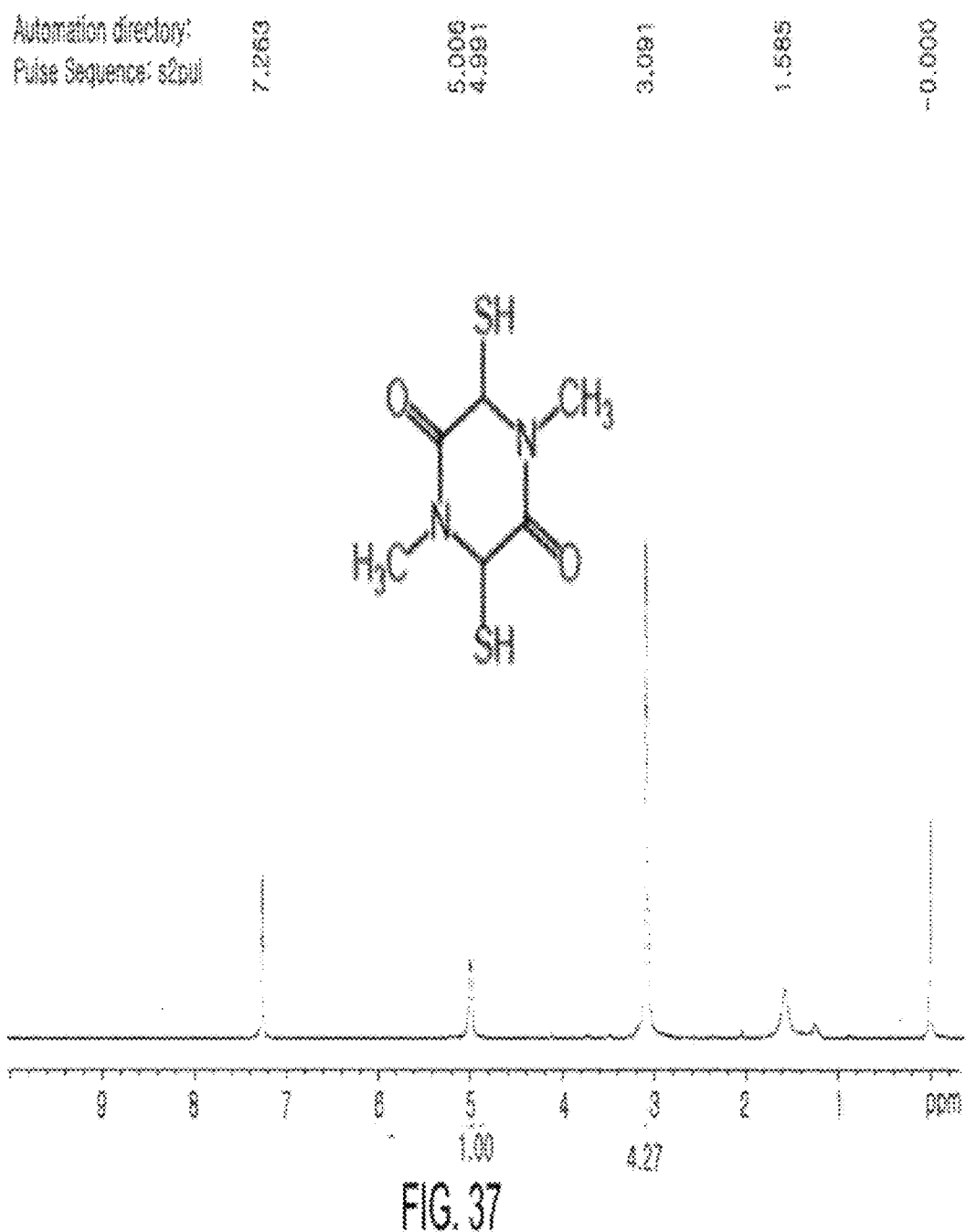

FIG. 37 is a diagram showing a $^1$H NMR spectrum of Compound A2R according to the present invention.

Figure 38:
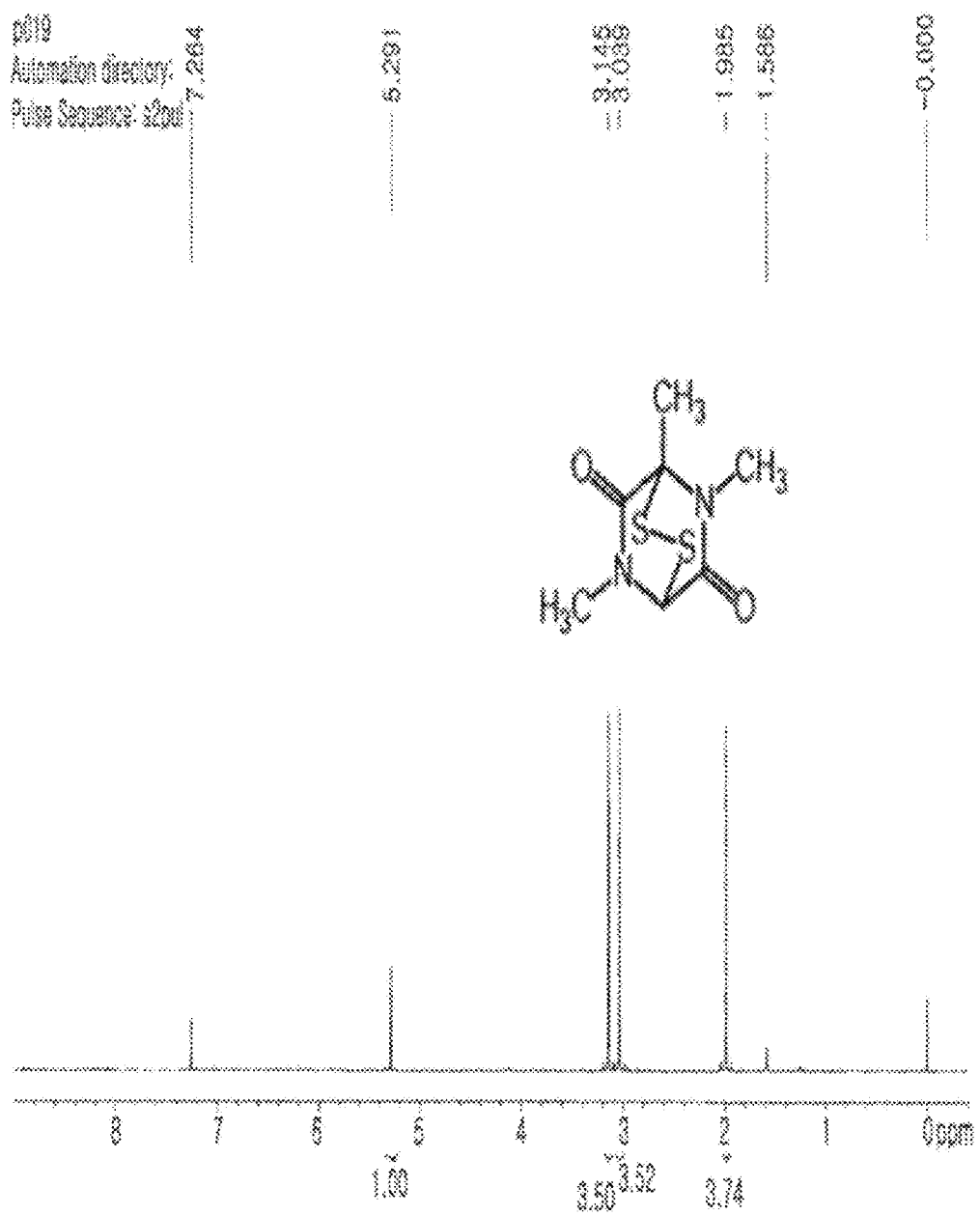

FIG. 38 is a diagram showing a $^1$H NMR spectrum of Compound A3 (Chemical Formula 8) according to the present invention.

Figure 39:
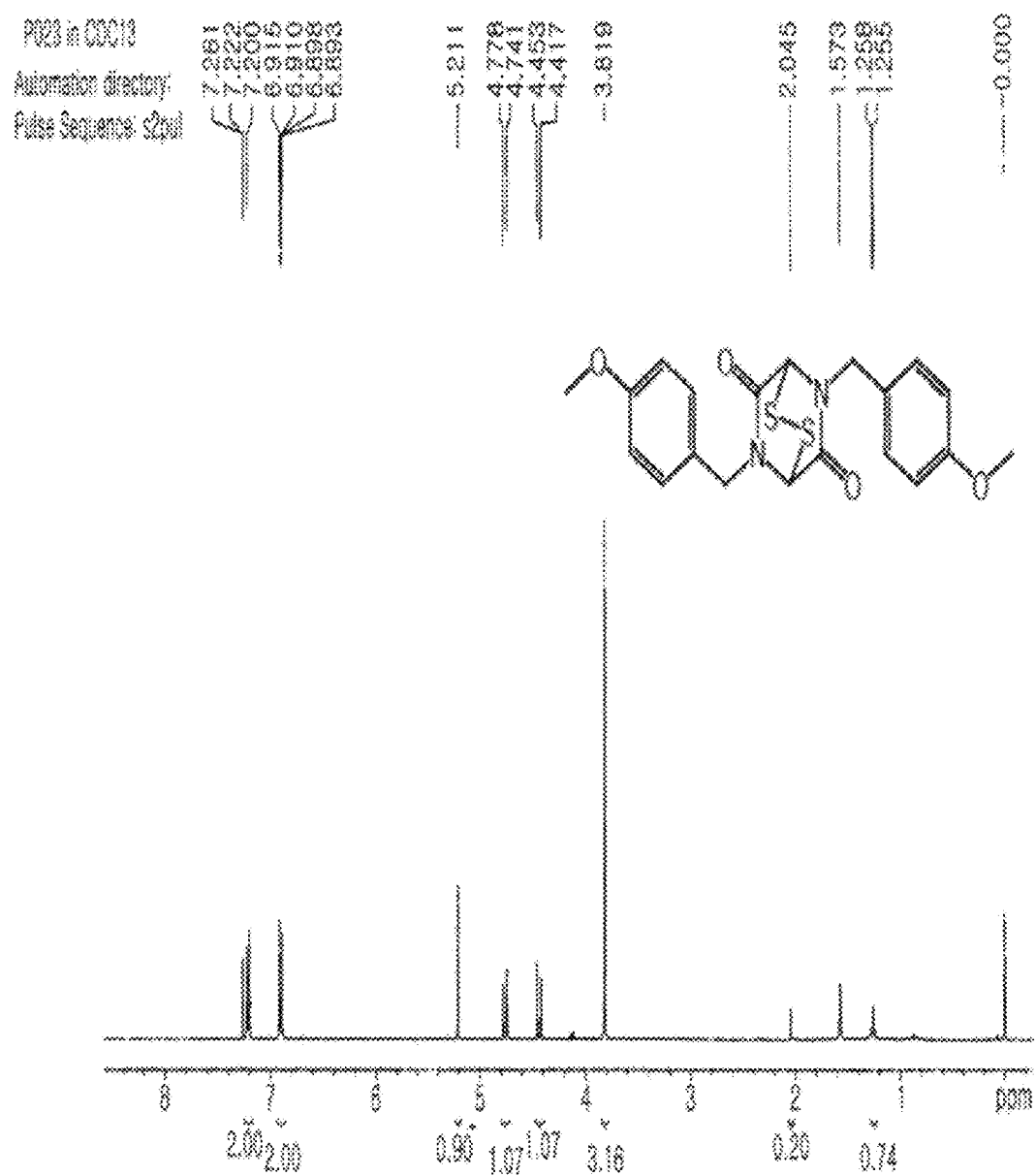

FIG. 39 is a diagram showing a $^1$H NMR spectrum of Compound A4 (Chemical Formula 9) according to the present invention.

Figure 40:
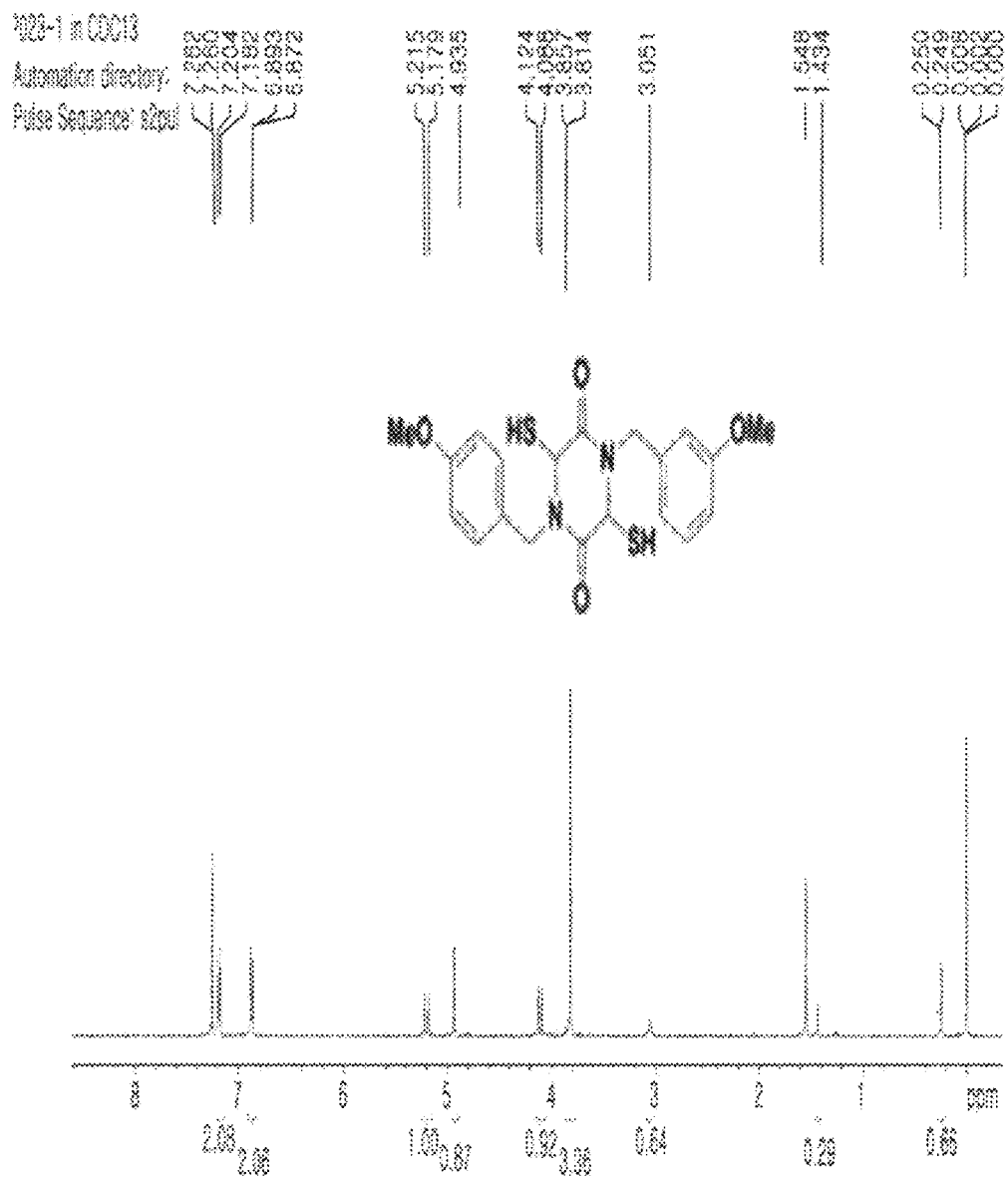

FIG. 40 is a diagram showing a $^1$H NMR spectrum of Compound A4R according to the present invention.

Figure 41:
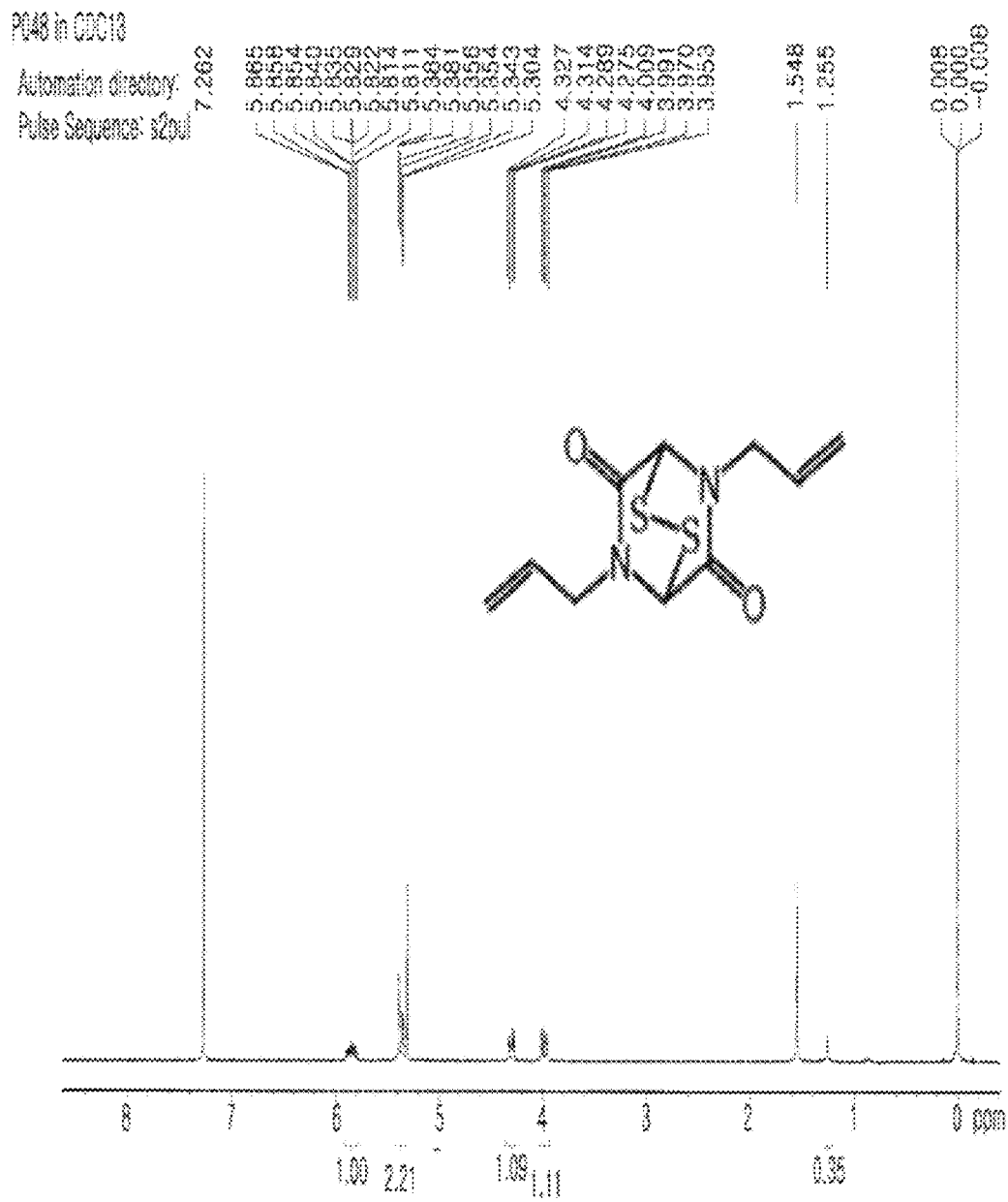

FIG. 41 is a diagram showing a $^1$H NMR spectrum of Compound A5 (Chemical Formula 10) according to the present invention.

Figure 42:
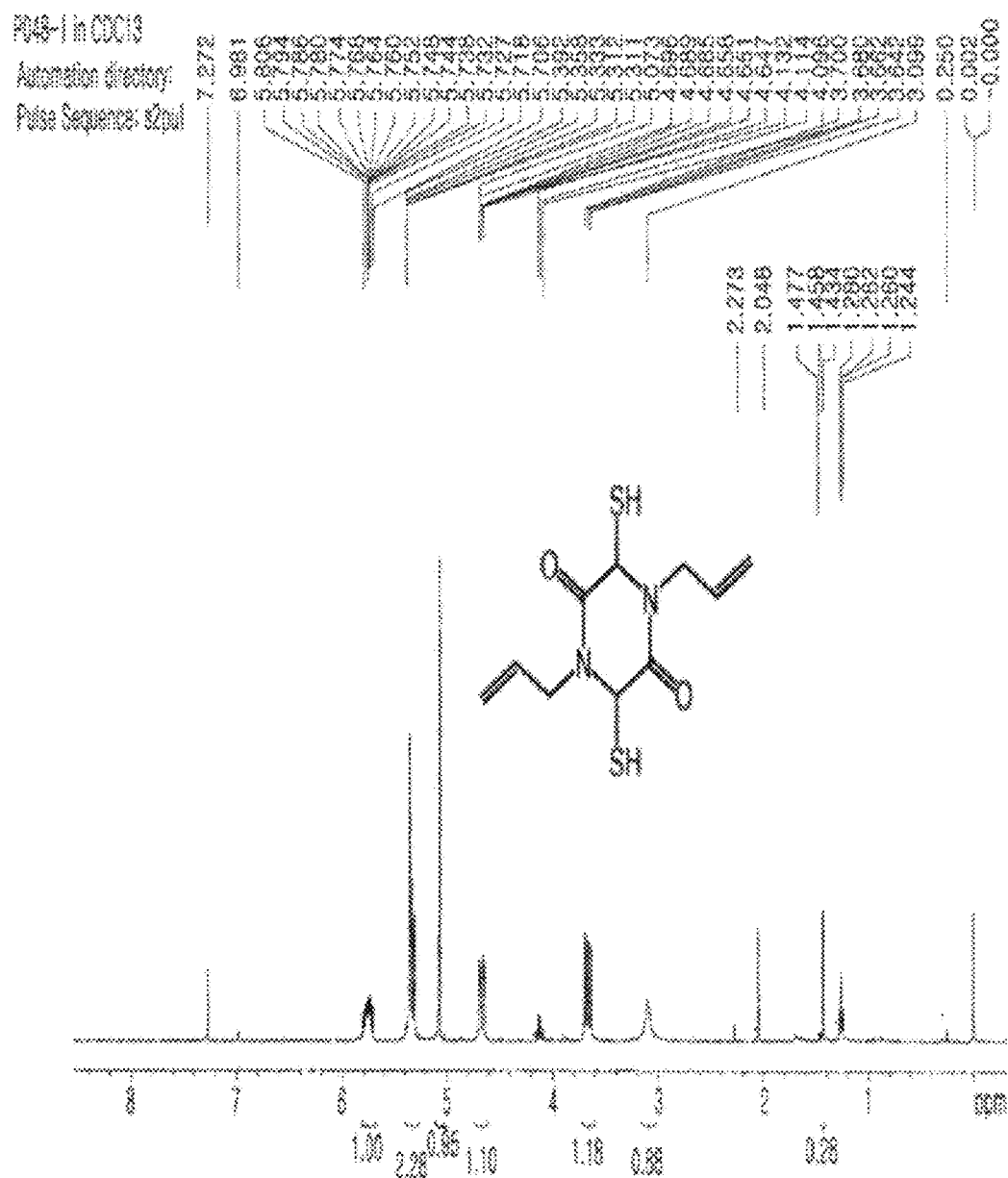

FIG. 42 is a diagram showing a $^1$H NMR spectrum of Compound A5R according to the present invention.

Figure 43:
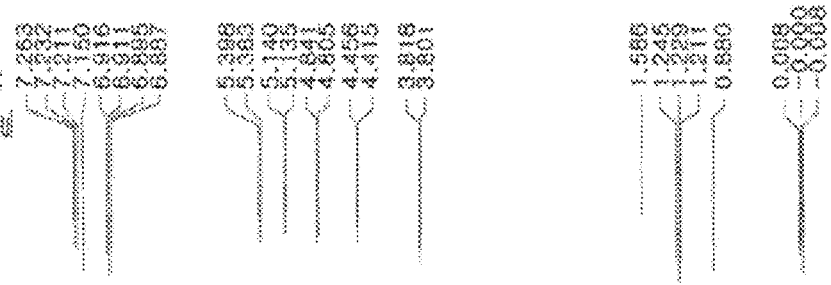
Figure 43:
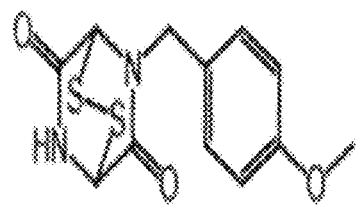
Figure 43:
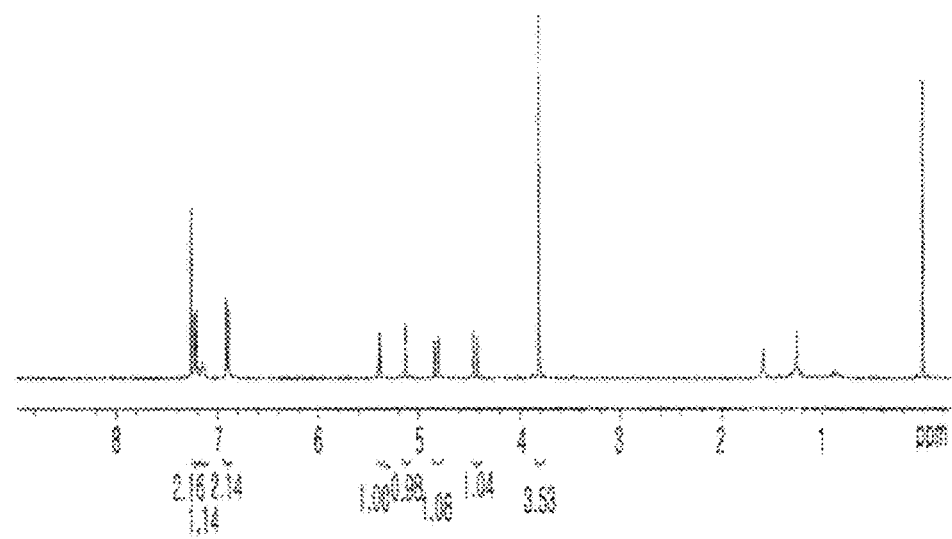

FIG. 43 is a diagram showing a $^1$H NMR spectrum of Compound A6 (Chemical Formula 11) according to the present invention.

Figure 44:
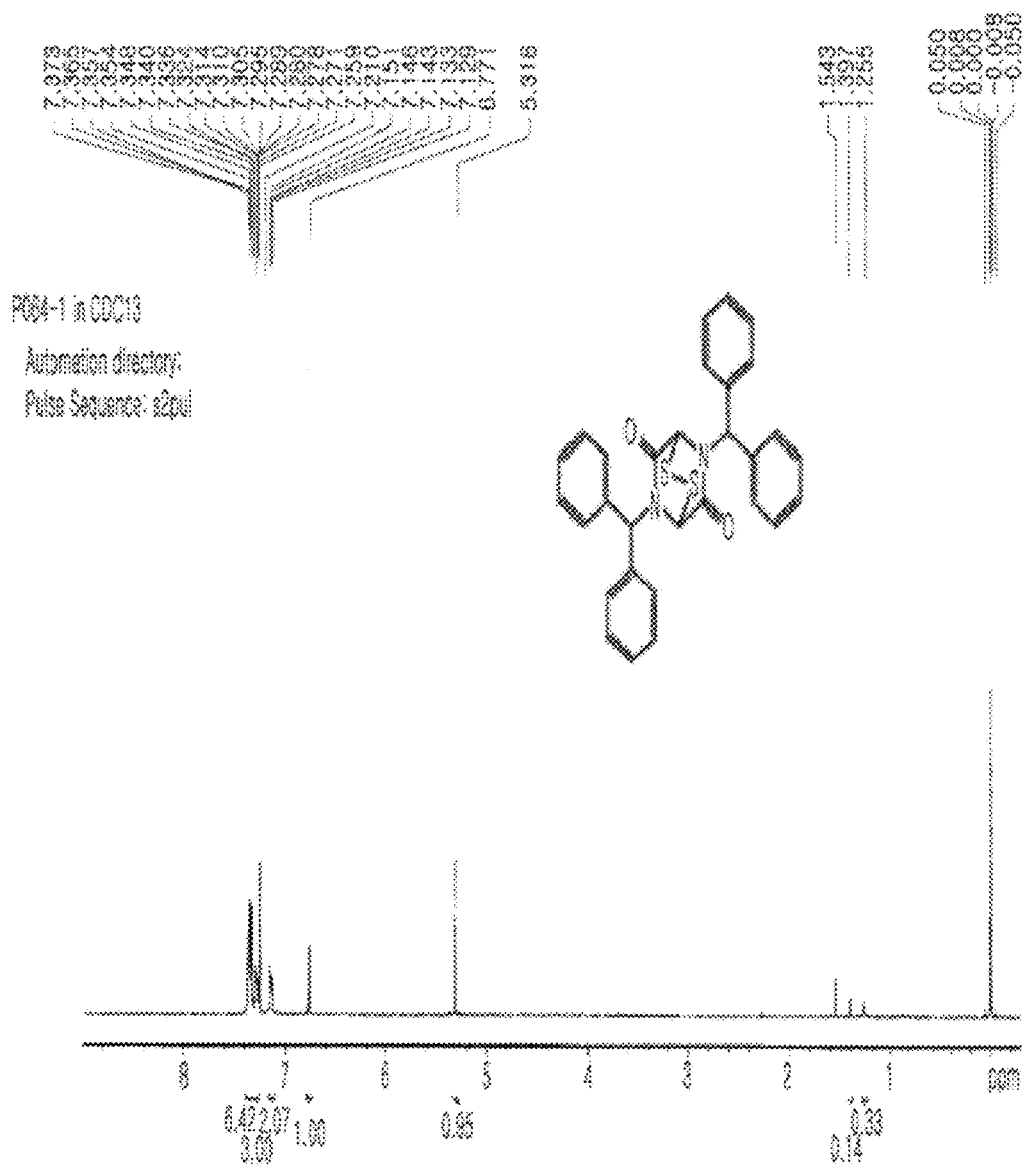

FIG. 44 is a diagram showing a $^1$H NMR spectrum of Compound A7 (Chemical Formula 12) according to the present invention.

Figure 45:
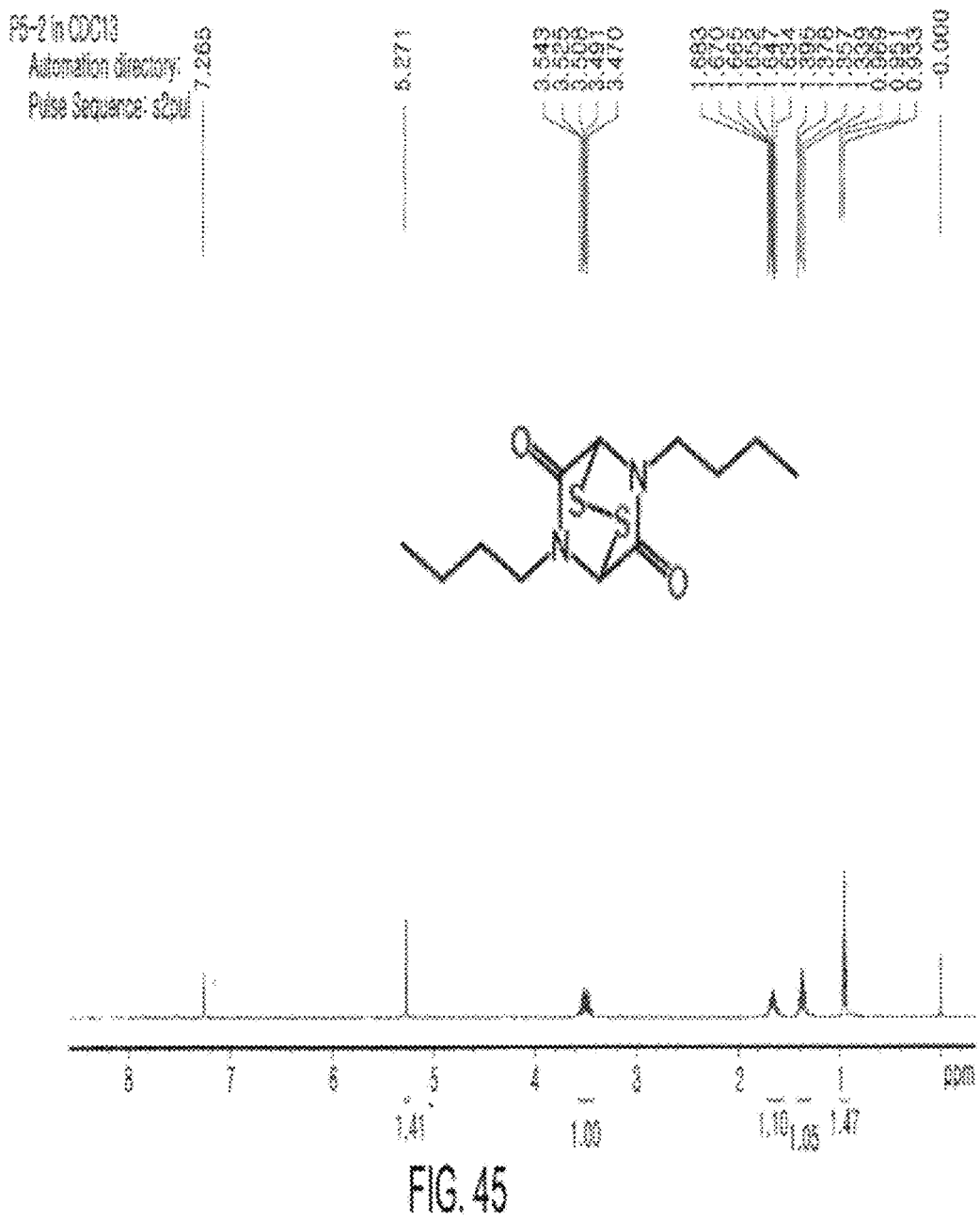

FIG. 45 is a diagram showing a $^1$H NMR spectrum of Compound A8 (Chemical Formula 13) according to the present invention.

Figure 46:
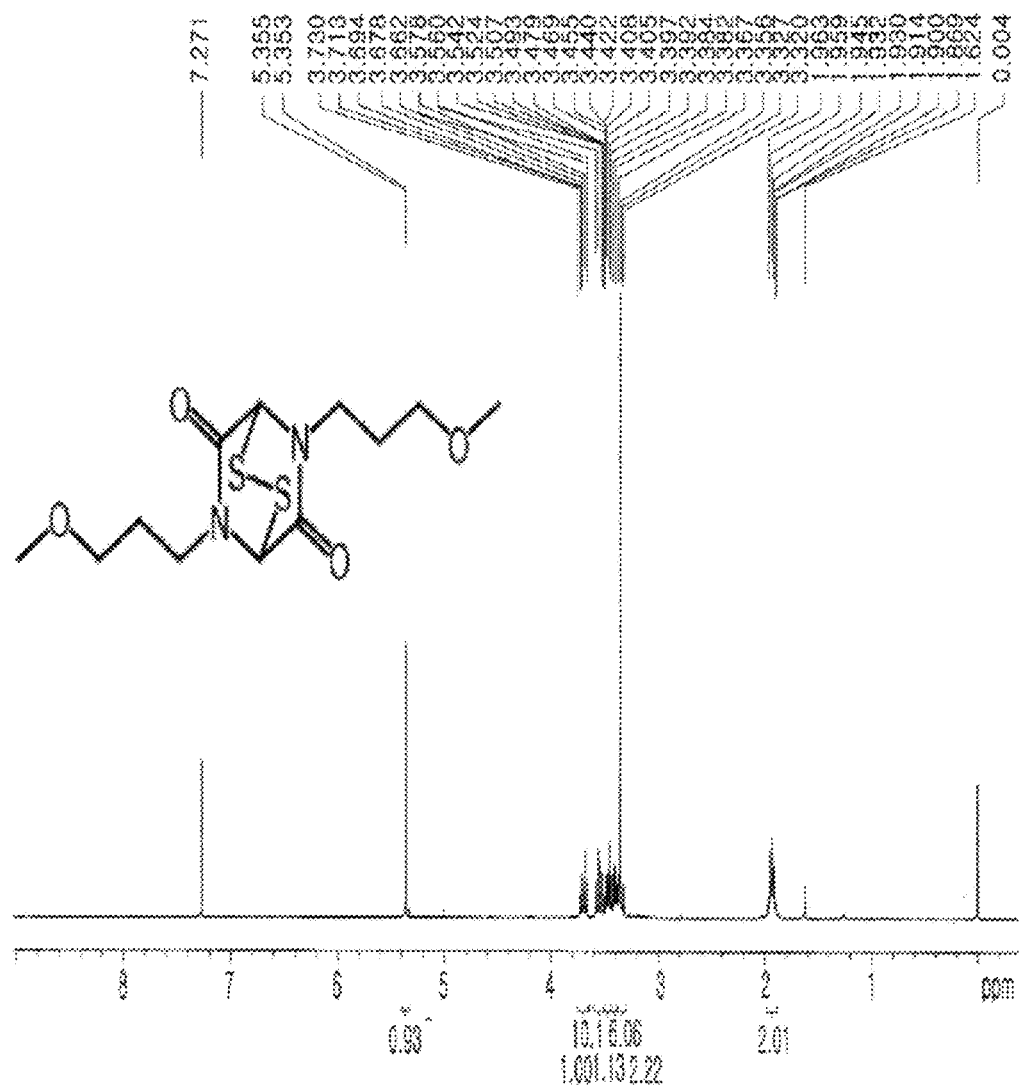

FIG. 46 is a diagram showing a $^1$H NMR spectrum of Compound A9 (Chemical Formula 14) according to the present invention.

Figure 47:
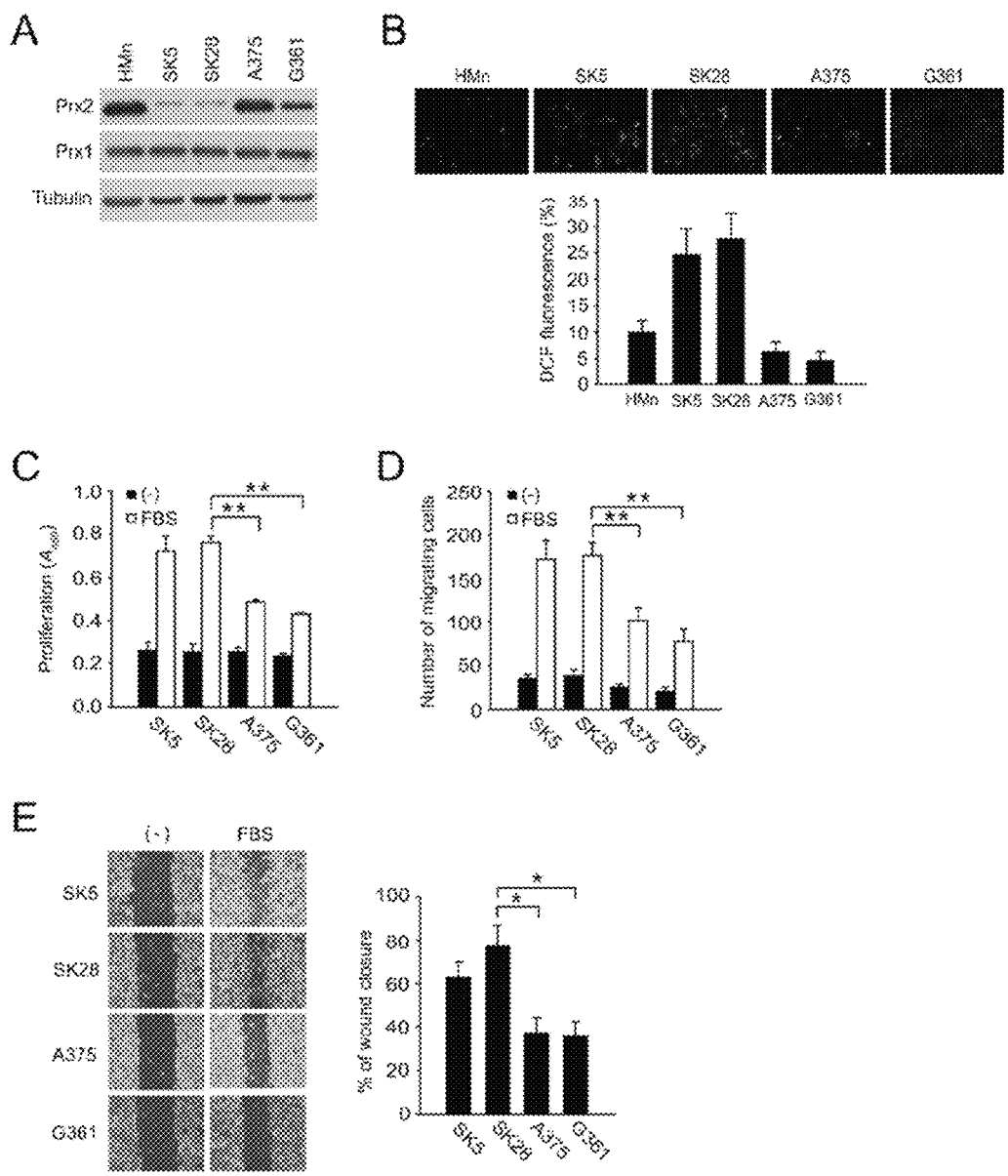

FIG. 47 is a diagram showing the effects of PrxII (Prx2) on the proliferation and the migration of melanoma cell lines. A shows the expression level of PrxII in 4 different types of melanoma cell lines (SK5, SK28, A375 and G361). B shows the intracellular hydrogen peroxide level of the melanoma cell lines. The intracellular hydrogen peroxide level is detected using DCFH-DA, an oxidation-sensitive dye, and quantified. Representative images are shown, and the bars in the graph are mean±standard deviation of the relative fluorescence values averaged from 60 to 80 cells. C is a diagram showing the proliferative activity comparisons between the melanoma cell lines. D and E are diagrams showing the migratory activity comparisons between the melanoma cell lines, and the activities are measured by chemotactic transmigration assay (D) and wound healing assay (E). The experiment is repeated 3 times (*P<0.01; **P<0.005).

Figure 48:
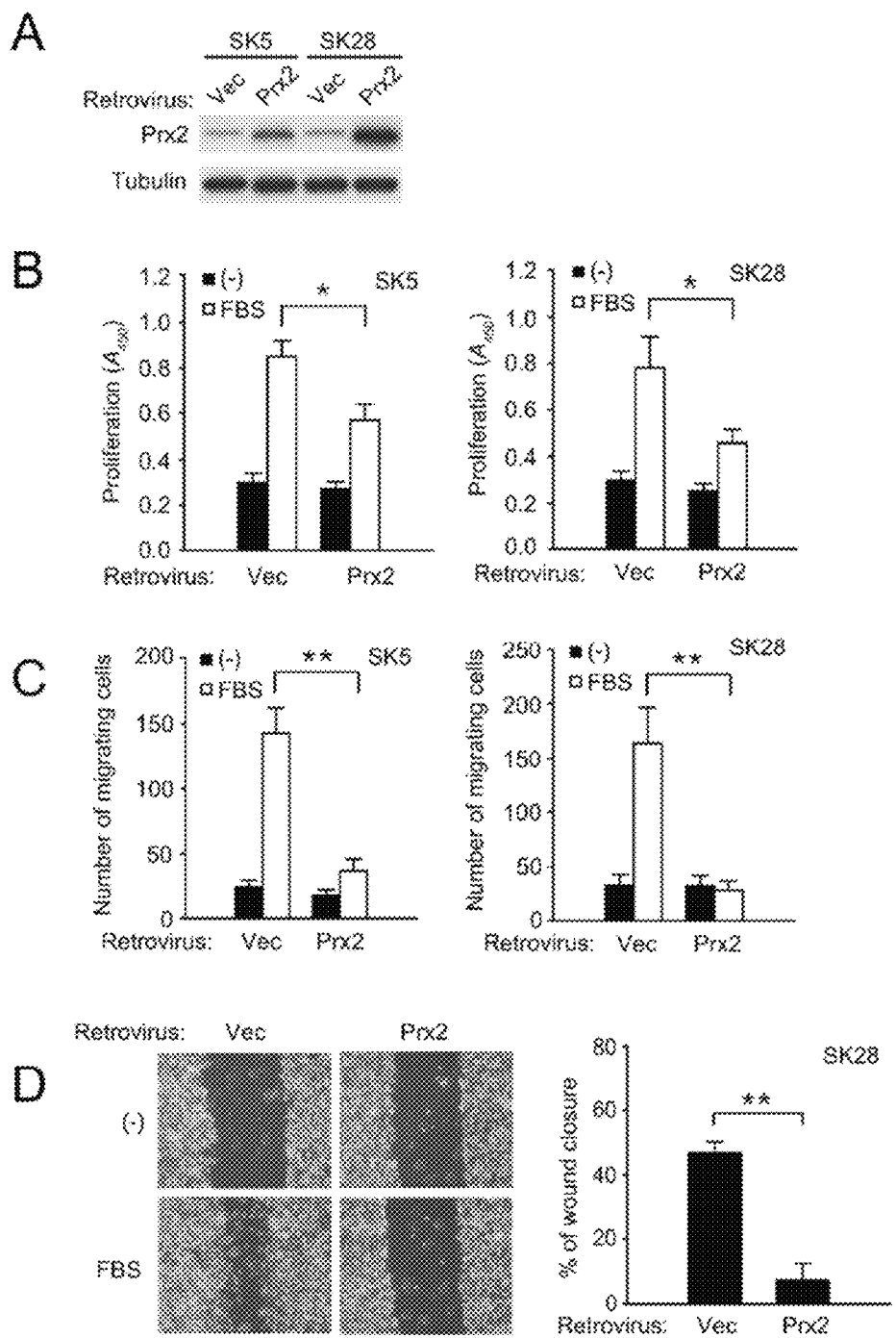

FIG. 48 is a diagram showing the effects of proliferation and migration inhibition by the expression of PrxII in PrxII-deficient SK-MEL cell lines. A is a diagram showing the retroviral expression of PrxII in SK-MEL cell lines. B to D are diagrams each showing the proliferation (B) and the migration (C and D) of control group (vec)- and PrxII-expressed SK-MEL cell lines. The cells are infected with control- and PrxII-encoding retroviruses for 24 hours. The experiment is repeated 3 times (*P<0.01, **P<0.005).

Figure 49:
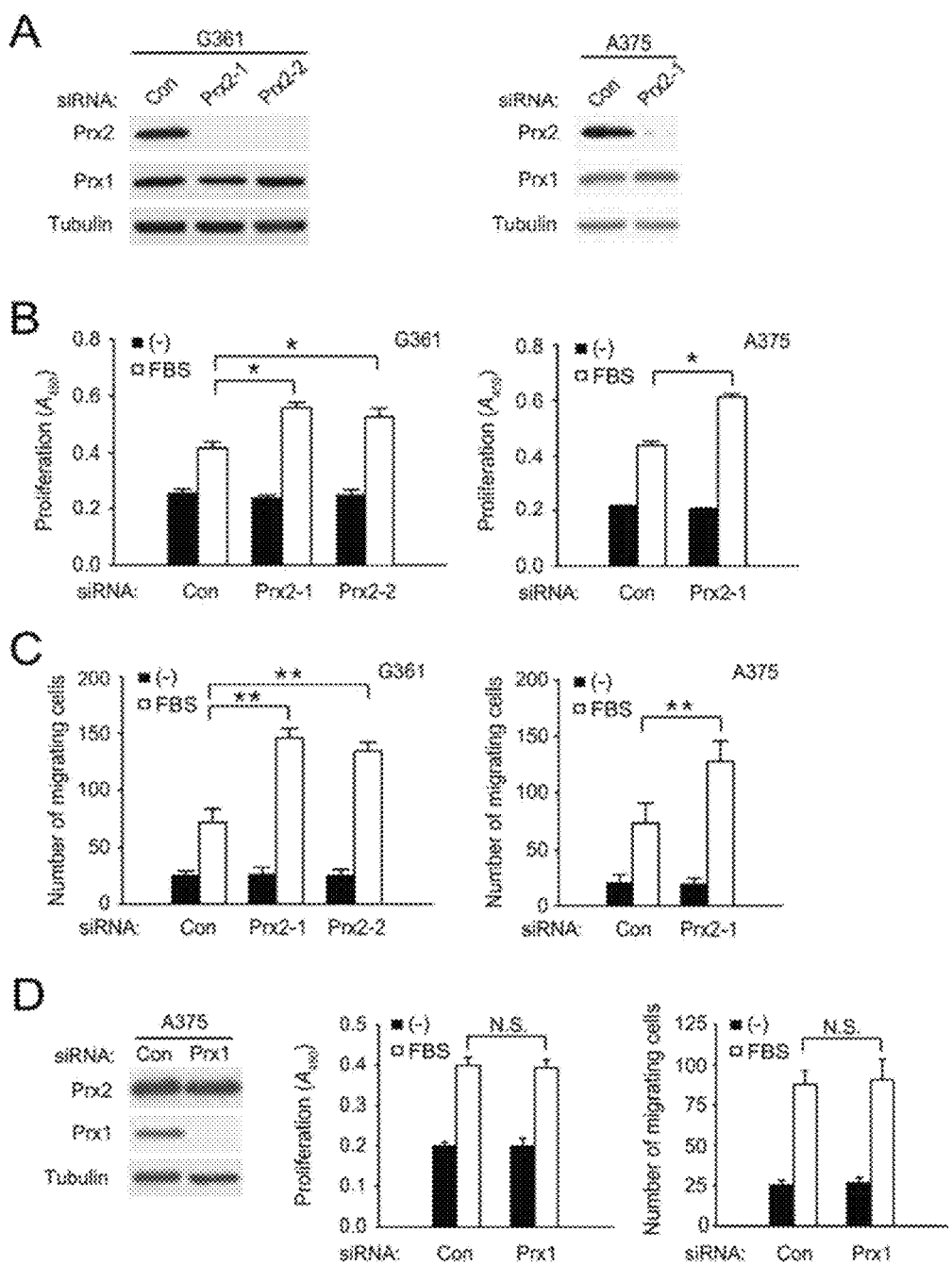

FIG. 49 is a diagram showing the effects of PrxII knockdown on the proliferation and the migration of PrxII-expressed melanoma cell lines. A is a diagram showing selective human PrxII knockdown in G361 and A375 cell lines using two different specific siRNA. B and C are diagrams showing proliferation (B) and migration (C) of G361 and A375 cell lines knocked down with a control group (con) and PrxII. D is a diagram showing proliferation and migration of PrxI knocked down A375 cells for serum stimulation using specific siRNA. The cells are infected with a control or isoform-specific siRNA for 24 hours as indicated. The experiment is repeated 3 times (*P<0.01; **P<0.005; N.S. means not significant).

Figure 50:
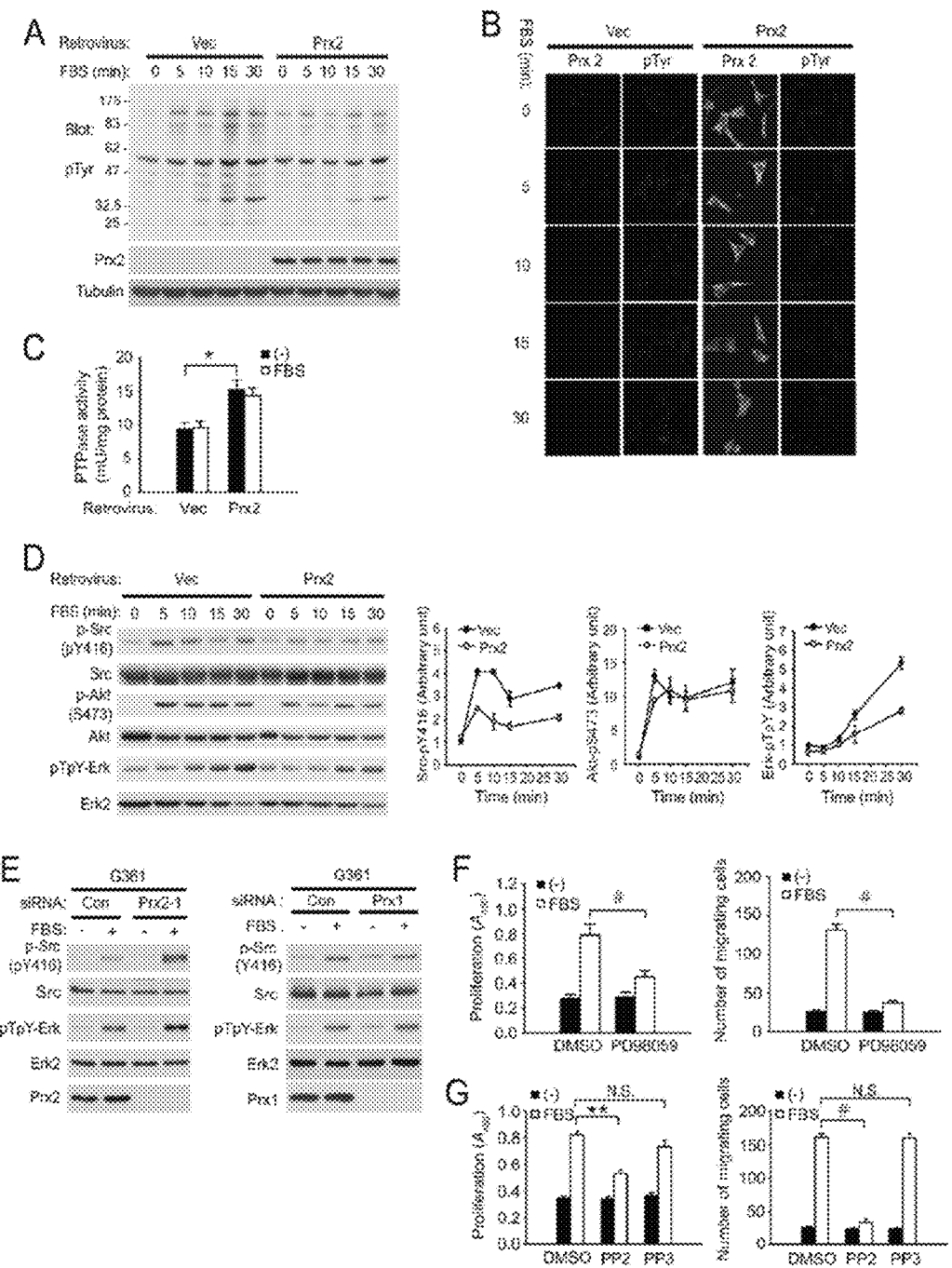

FIG. 50 is a diagram showing the inhibition effects of PrxII on serum-induced Src and ERK activation through the preservation of PTP activities. A and B are diagrams showing serum-induced tyrosine phosphorylation in control group (vec)- and PrxII-expressed SK28 cells. Tyrosine phosphorylation is detected by immunoblotting (A) and immunostaining (B) using an anti-pTyr antibody (4G10). Representative blots and images are shown (n=3). C is a diagram showing the PTP activities in control group- and PrxII-expressed SK28 cells. The total PTP activities are measured using a poly-(Glu4-pTyr) peptide. D and E are diagrams showing the activities of intracellular signaling molecules in PrxII-expressed SK28 cells (D) and PrxI/II-deficient G361 cells (E). The G361 cells are stimulated with serum for 30 minutes. The phospho-specific band is quantified, and the intensity of the corresponding non-phospho protein band is normalized. The data are presented as mean±standard deviation of the relative band intensities from 3 independent experiments. F and G are diagrams showing the proliferation and the migration of SK28 melanoma cells when specific MEK (F) and Src (G) inhibitors are present. The SK28 cells are serum-starved for 24 hours, and pretreated with PD98059 (5 µM) or PP2/PP3 (1 µM each) for 1 hour prior to serum stimulation. PP3 is an inactive analog of PP2. DMSO is used as a control vehicle for non-treated samples. The experiment is repeated 3 times (*P<0.01; **P<0.005; #P<0.001; N.S. means not significant).

Figure 51:
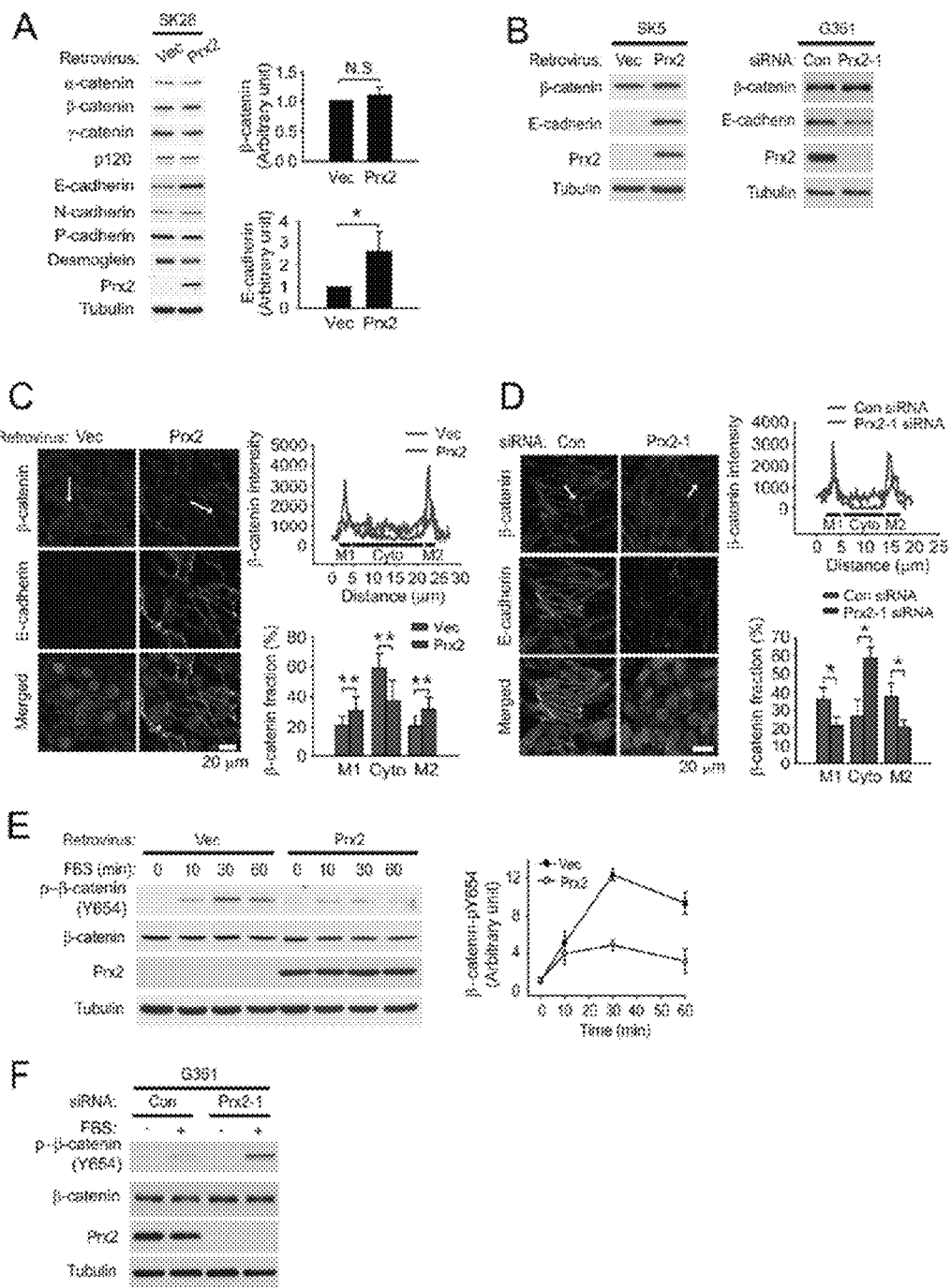

FIG. 51 is a diagram showing an E-cadherin/β-catenin complex increase at the adherens junction of melanoma cells by PrxII expression. A shows the expression of adherens junction protein in the control group (vec) and PrxII-expressed SK28 cells. The intensities of β-catenin and E-cadherin bands are quantified, and normalized with respect to the intensity of the corresponding tubulin band. The data are presented as mean±standard deviation of the relative band intensities from 3 independent experiments (*P<0.005; N.S., not significant). B is a diagram showing the expression of β-catenin and E-cadherin in PrxII-expressed SK5 and PrxII-deficient G361 cells. C and D are diagrams showing the immunostaining of β-catenin and E-cadherin in PrxII-expressed SK5 (C) and PrxII-deficient G361 (D) cells. The overlapped image represents the coexistence of two proteins in the plasma membrane of the PrxII-expressed cells (Yellow). The fluorescence intensities are quantified following the white arrow (Upper right) and presented as the percentage of the intensity of the indicated fraction with respect to the total intensity (Lower right, n=33 cells per group, *P<0.001). M1 and M2 represent plasma membrane, and Cyto represents cytoplasm. E is a diagram showing the decrease of β-catenin Y654 phosphorylation due to the PrxII expression in the SK28 cells. The phospho-specific band is quantified, and normalized with respect to the intensity of the corresponding non-phospho protein band. The data are presented as mean±standard deviation of the relative band intensities from 3 independent experiments. F is a diagram showing the increased β-catenin Y654 phosphorylation by the PrxII knockdown in G361 cells. A representative immunoblot is shown from 3 independent experiments giving the same results.

Figure 52:
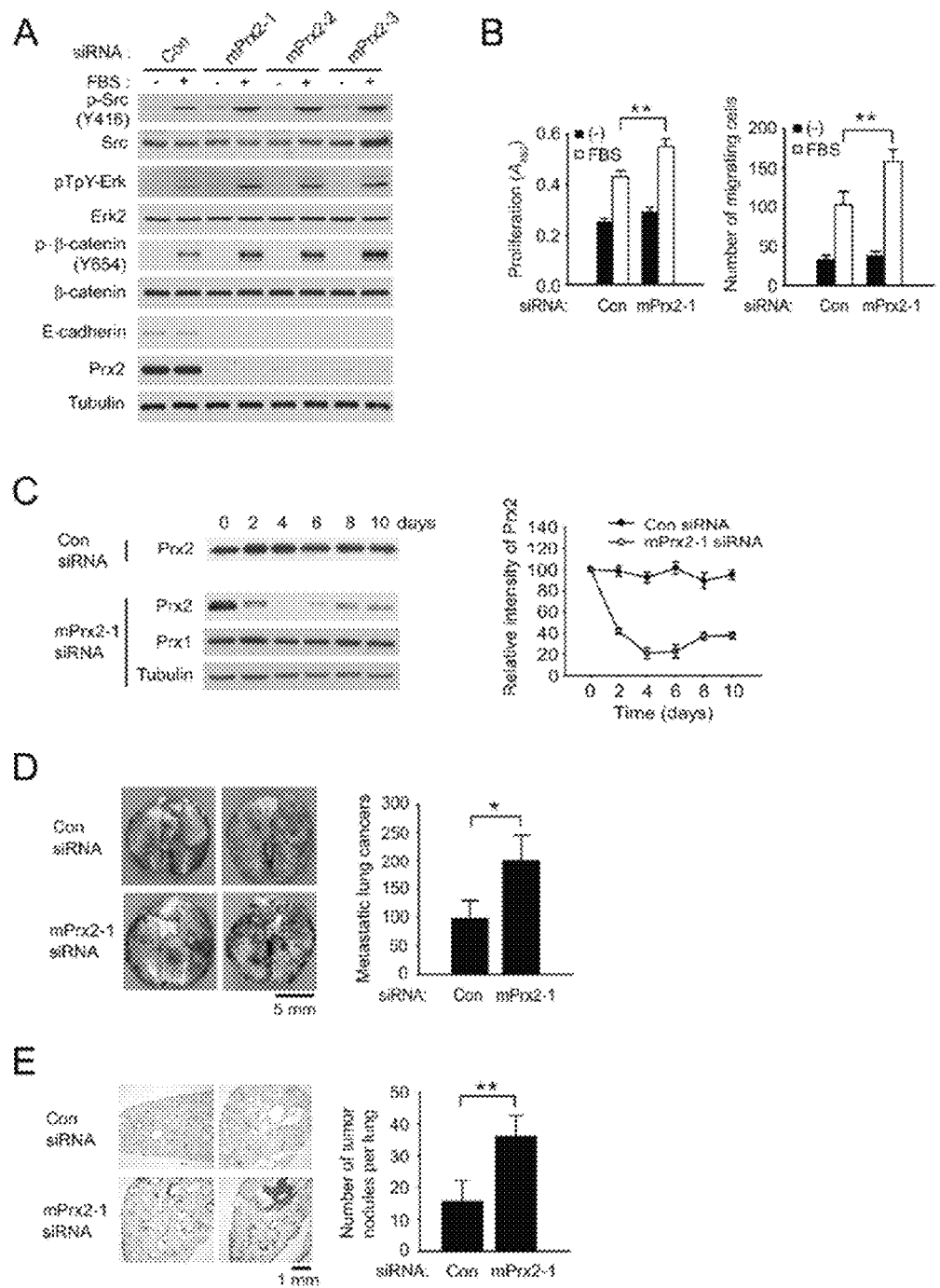

FIG. 52 is a diagram showing the effects of PrxII in inhibiting the metastatic activity of melanoma cells in vivo. A is a diagram showing improved Src/ERK activation and β-catenin phosphorylation, and reduced E-cadherin expression by the PrxII knockdown in B16F10 mouse melanoma cells. B is a diagram showing proliferation and migration with serum stimulation in control group- and PrxII-deficient B16F10 mouse melanoma cells (n=3, **P<0.001). C is a diagram showing a PrxII expression level according to the PrxII knockdown period of time in B16F10 cells. The cells are transfected with mPrx2-1 siRNA, and immunoblot analysis is carried out. The intensity of PrxII band is quantified, and normalized with respect to the intensity of the corresponding tubuline band. The data are presented as mean±standard deviation of relative band intensities from 3 independent experiments. D and E are diagrams showing the metastasis of control group- and PrxII knocked down B16F10 melanoma cells to lung. The transfected cells are injected to a mouse by intravenous injection. After 10 days, the lung is removed, and the melanoma tumor nodules are counted in the (D) surface and (E) HE-stained tissue sections. The data are presented as mean±standard error (S.E.M.) (*P<0.005, **P<0.001).

Figure 53:
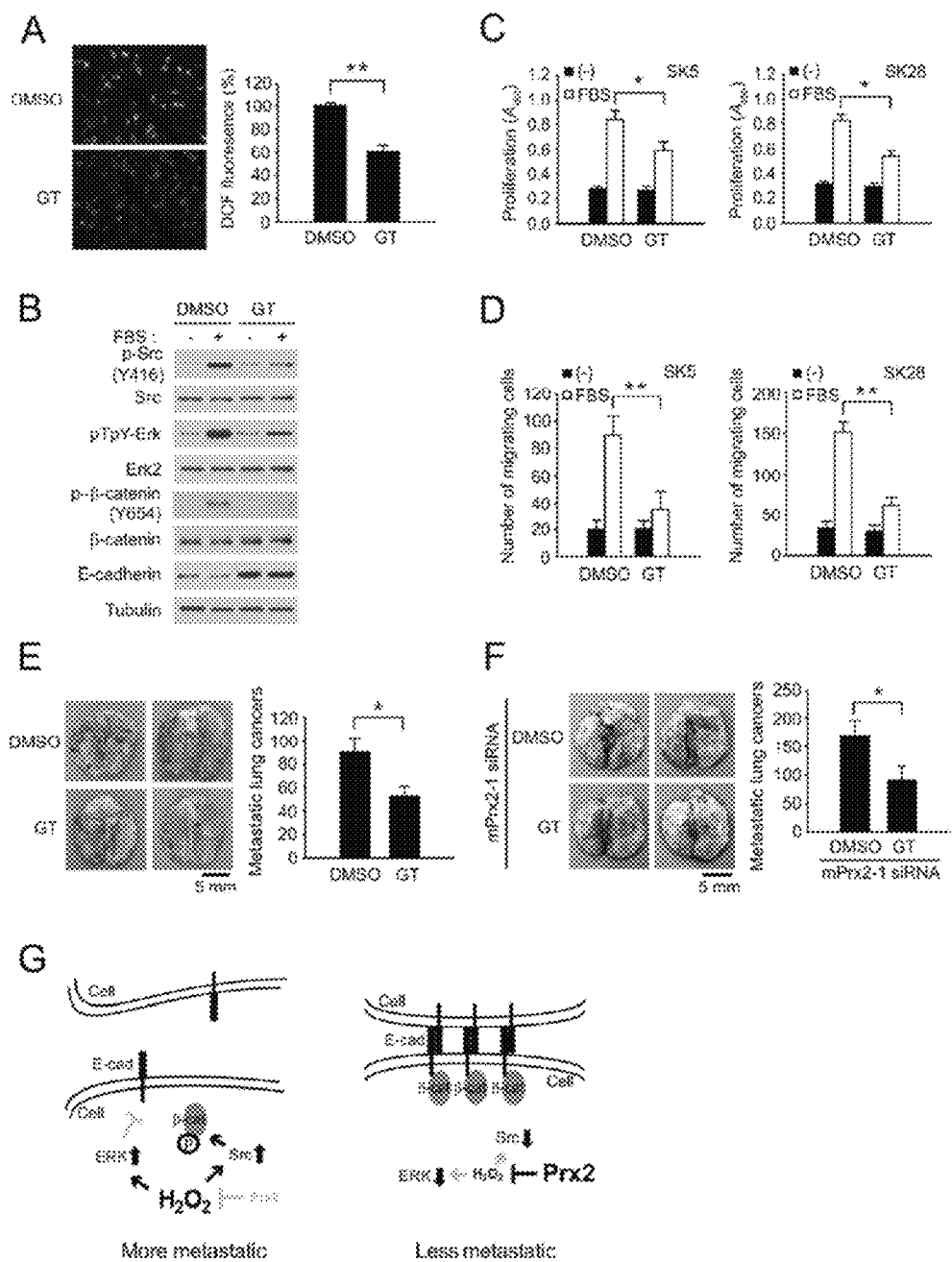

FIG. 53 is a diagram showing the effects of gliotoxin (GT), an ETP derivative, in inhibiting the metastatic activity of melanoma cells. A is a diagram showing the intracellular hydrogen peroxide level in a control vehicle (DMSO)- or GT-treated SK28 melanoma cell line. Representative images are shown, and the bars in the graph are mean±standard deviation (**P<0.005) of relative DCF fluorescence values averaged from 60 to 80 cells. B is a diagram showing the expression of serum-induced protein phosphorylation and E-cadherin in control vehicle (DMSO)- and GT-treated SK28 cells. C and D are diagrams showing the proliferation (C) and the migration (D) of control vehicle (DMSO)- and GT-treated SK5 and SK28 cell lines. The serum-starved cells are pretreated with GT (100 nM) for 1 hour, and then stimulated with serum. The experiment is repeated 3 times (*P<0.01, **P<0.005). E and F are diagrams showing the metastasis of B16F10 melanoma cells to lung in control vehicle- and GT-injected mice. Parent (E) or mPrx2-1 siRNA-transfected (F) B16F10 melanoma cells are intravenously injected to mice (7 per each group), and then DMSO or GT (300 μg/kg, i.p.) is injected 5 times over 10 days. After that, the lung is removed, and melanoma tumor nodules are counted on the surface. The data are presented as mean±standard error (S.E.M.) (*P<0.01). G is a schematic diagram showing the anti-metastatic function of PrxII in melanoma cells. When PrxII is not present, the intracellular hydrogen peroxide level increases. The increased cellular hydrogen peroxide level improves the activities of Src and ERK with respect to stimulation. The activated Src kinase phosphorylates β-catenin ((β-cat) and triggers the release of β-cat from the adherens junction with respect to cytoplasm, while the activated ERK kinase inhibits the expression of E-cadherin (E-cad). Consequently, E-cadherin/β-catenin complexes are destroyed at the adherens junction, and as a result, melanoma cells have higher metastatic ability. By contrast, the PrxII expression removes intracellular hydrogen peroxide thereby inhibits Src and ERK activation. Accordingly, β-catenin protein is maintained, and the E-cadherin level increases, and therefore, E-cadherin/β-catenin complexes are increased at the adherens junction. As a result, the PrxII expression strengthens adhesivity between melanoma cells so as not to be metastasized.

Figure 54:
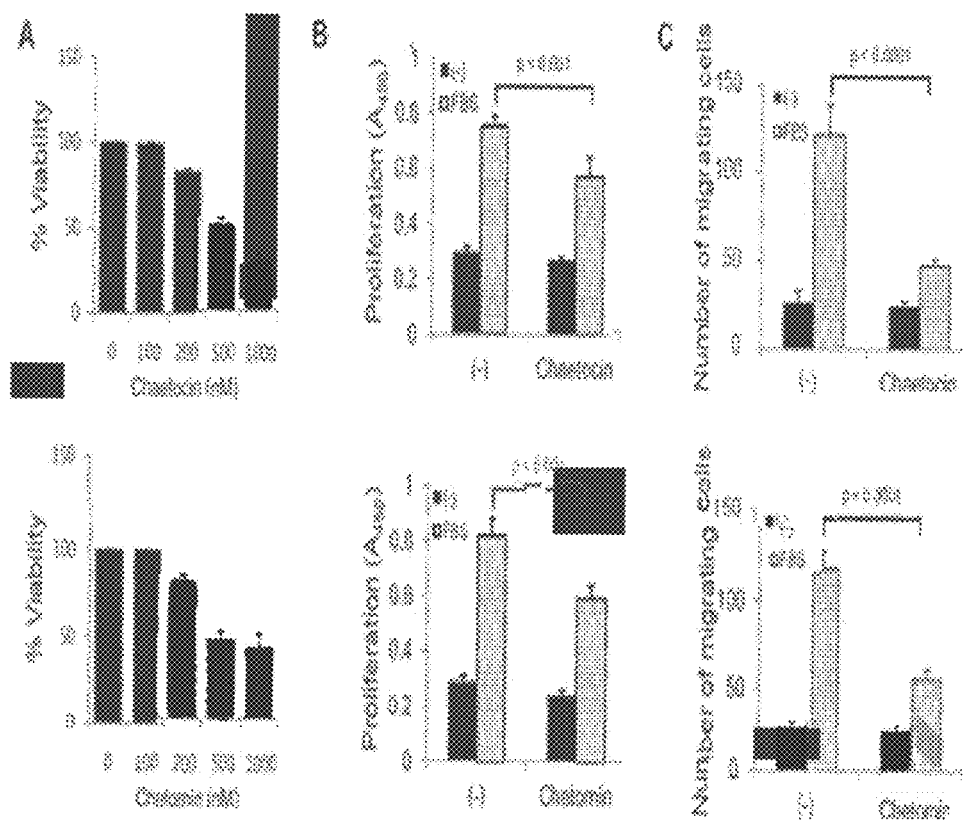

FIG. 54 is a diagram showing the inhibition of melanoma cell proliferation and migration by chaetocin and chetomin. A vehicle (DMSO) or 100 nM of the indicated ETP compound is treated with SK-MEL28 melanoma cells, and the results of cell cytotoxicity (A), proliferation (B) and migration (C) measurements are shown in the graphs. The ETP compound was used at a concentration of 100 nM exhibiting no cytotoxicity.

The proliferation and the migration of cells are promoted by serum (FBS). The p value in each graph means a statistically significant value.

Figure 55:
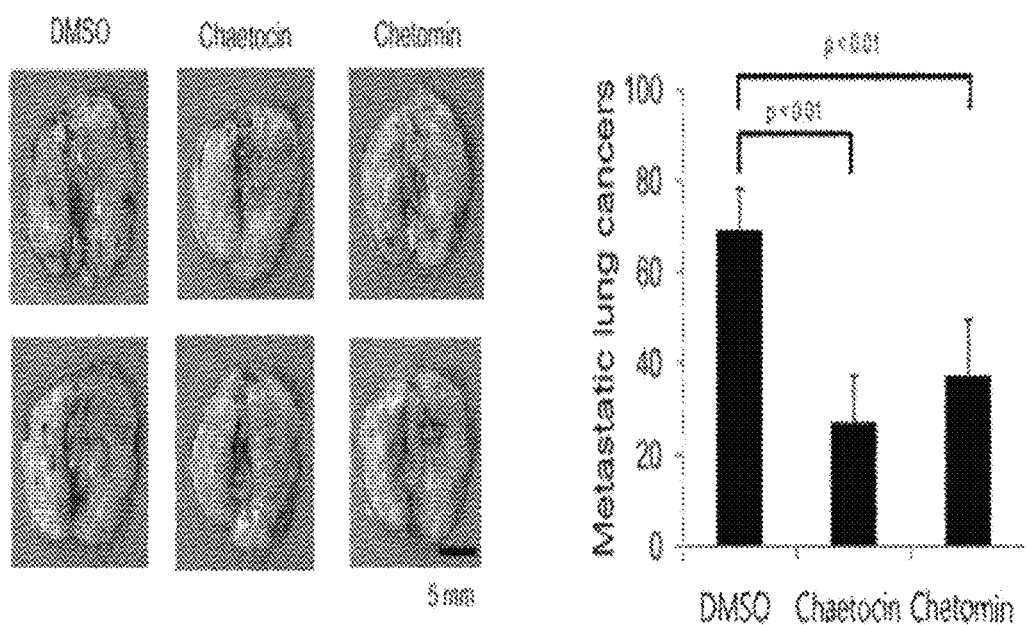

FIG. 55 is a graph showing that whether the metastasis of B16F10 melanoma cells to lung occurs in a control vehicle- or ETP compound-injected mouse. B16F10 melanoma cells are intravenously injected to mice (5 per group), and then DMSO (DMSO) or an ETP compound (300 mg/kg, i.p.) is injected 5 times over 10 days. Melanoma tumor nodules located on the surface of the separated lung are counted, and this is shown in the graph. The p value in the graph means a statistically significant value.

DETAILED DESCRIPTION OF THE PREFERRED EMBODIMENTS

Hereinafter, the present invention will be described in more detail with reference to examples. However, these examples for illustrative purposes only, and the scope of the present invention is not limited to these examples.

Synthesis of Epidithiodioxopiperazine Derivative Including Intramolecular Disulfide Bridged Bond Preparation Example 1: Preparation of 2,3-dithia-5,7-diazabicyclo[2.2.2]octane-6,8-dione (A1, Chemical Formula 15)

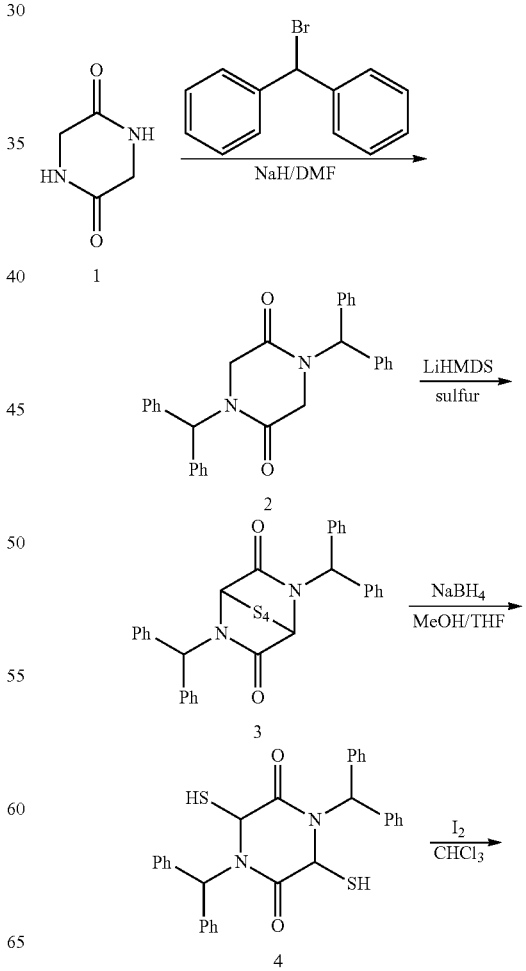

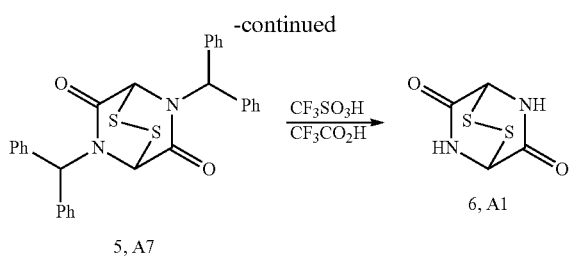

A. 1,4-dibenzhydrylpiperazine-2,5-dione (2)

After NaH (60% dispersed in mineral oil, 385 mg, 9.64 mmol) was dispersed in 10 ml of DMF, anhydrous glycine (500 mg, 4.38 mmol) was added thereto in an ice water bath. After the mixture was stirred for 10 minutes, bromodiphenyl methane (2.27 g, 2.1 eq.) was slowly added thereto. The result was reacted overnight at room temperature. Water was added to the reaction solution and the result was stirred. The precipitates were filtered, washed with water, and then dried under reduced pressure to obtain 1,4-dibenzhydrylpiperazine-2,5-dione (2) (1.4 g, yield 71%).

$^1$H NMR (400 MHz, CDCl$_3$): δ ppm 7.39-7.31 (m, 12H), 7.21-7.19 (d, 8H), 7.09 (s, 2H), 3.83 (s, 4H).

B. 7,9-dibenzhydryl-2,3,4,5-tetrathia-7,9-diazabicyclo[4.2.2]decane-8,10-dione (3)

After sulfur (402 mg, 12.54 mmol) was dispersed in 5 ml of dry THF, LiHMDS (1.0 M in THF, 4.7 ml, 3.0 eq.) was added thereto drop by drop over 2 minutes under argon atmosphere. After the mixture was stirred for approximately 1 minute, a solution in which the compound (2; 700 mg, 1.567 mmol) obtained in Step A was dissolved in 20 ml of THF was added thereto drop by drop. After the result was stirred for approximately 1 minute, LiHMDS (1.0 M in THF, 3.13 ml, 2.0 eq.) was added thereto drop by drop, and then the result was stirred for 30 minutes. After the reaction was complete, the result was extracted twice by adding a saturated NH$_4$Cl solution and ethyl acetate (EA) (×3). The organic layers were combined, treated with magnesium sulfate, filtered, and then the solvent was removed. The residue was purified using silica gel column chromatography (Hex:EA=2:1) to obtain 7,9-dibenzhydryl-2,3,4,5-tetrathia-7,9-diazabicyclo[4.2.2]decane-8,10-dione (3; 230 mg, yield: 26%).

$^1$H NMR (400 MHz, CDCl$_3$): δ ppm 7.39-7.32 (m, 12H), 7.21 (m, 4H), 7.07 (m, 4H), 6.95 (s, 2H), 5.14 (s, 2H).

C. 3,6-dimercapto-1,4-dibenzhydrylpiperazine-2,5-dione (4)

After 7,9-dibenzhydryl-2,3,4,5-tetrathia-7,9-diazabicyclo[4.2.2]decane-8,10-dione (3; 230 mg, 0.401 mmol) was dissolved in methanol, NaBH$_4$ (45 mg, 3.0 eq.) was slowly added thereto in an ice water bath. After the mixture was stirred for 30 minutes and the reaction was complete, the solvent was removed. Water and EA (×3) were added to the crude compound and the result was extracted. The organic layers were combined, treated with magnesium sulfate, filtered, and then the solvent was removed. The residue was dried under reduced pressure to obtain 3,6-dimercapto-1,4-dibenzhydrylpiperazine-2,5-dione (4). The compound was used for the next reaction without further purification.

D. 5,7-dibenzhydryl-2,3-dithia-5,7-diazabicyclo[2.2.2]octane-6,8-dione (5)

After the dithiol crude compound (4) was dissolved in 30 ml of chloroform, 20 ml of a solution in which iodine (101 mg, 0.401 mmol) was dissolved in chloroform was added thereto. After the mixture was reacted for 30 minutes at room temperature, the solvent was removed, and the residue was purified using silica gel column chromatography (EA: Hex=1:2) to obtain 5,7-dibenzhydryl-2,3-dithia-5,7-diazabicyclo[2.2.2]octane-6,8-dione (5) (130 mg, 2 step yield- 63%).

$^1$H NMR (400 MHz, CDCl$_3$): δ ppm 7.37-7.28 (m, 12H), 7.27 (m, 4H), 7.14 (m, 4H), 6.77 (s, 2H), 5.31 (s, 2H).

ESI-MS (M+Na): 531 calculated for C$_{30}$H$_{24}$N$_2$O$_2$S$_2$ 508.

E. 2,3-dithia-5,7-diazabicyclo[2.2.2]octane-6,8-dione (6; A1)

After the crude compound (5; 50 mg) obtained in Step D was dissolved in trifluoroacetic acid (TFA, 1 mL), triflic acid (CF$_3$SO$_3$H, 0.1 mL) was added thereto and reacted in an ice water bath. After the mixture was reacted for 30 minutes, the reaction was terminated by adding ice-cold water to the reaction solution, and the result was stirred. The produced solids were filtered and dried. After that, the solids were stirred in ether, filtered, and dried under reduced pressure to obtain 2,3-dithia-5,7-diazabicyclo[2.2.2]octane-6,8-dione (6; 8 mg, 47%). The NMR data of the obtained final product was shown in FIG. 35.

$^1$H NMR (400 MHz, CDCl$_3$): δ ppm 9.69 (br d, 2H), 5.65 (d, 2H).

ESI-MS (M-1): 175 calculated for C$_4$H$_4$N$_2$O$_2$S$_2$ 176.

Preparation Example 2: Preparation of 5,7-dimethyl-2,3-dithia-5,7-diazabicyclo[2.2.2]-octane-6,8-dione (A2, Chemical Formula 7)

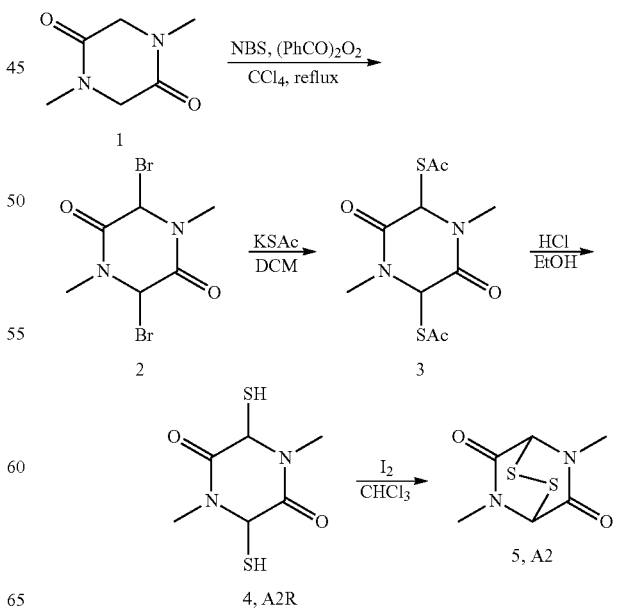

A. 3,6-dibromo-1,4-dimethylpiperazine-2,5-dione (2)

After a sarcosine anhydride (1) (500 mg, 3.52 mmol), N-bromosuccimide (1.87 g, 3.0 eq.) and benzoyl peroxide (85 mg, 0.1 eq.) were dispersed in carbon tetrachloride (50 ml), the mixture was heated under reflux for 2 hours. After the reaction was complete and the reaction material was cooled to room temperature, the obtained succinimide was filtered and washed with carbon tetrachloride. The filtrates were combined, dried with magnesium sulfate, and then filtered once again. The solvent was removed, and the residue was dried under reduced pressured to obtain 3,6-dibromo-1,4-dimethylpiperazine-2,5-dione (2). The obtained compound was used as it was for the next reaction without further purification.

$^1$H NMR (400 MHz, CDCl$_3$): δ ppm 6.04 (s, 2H), 3.15 (s, 6H).

B. 1,4-dimethyl-3,6-dioxopiperazine-2,5-diyl-diethanethioate (3)

After 3,6-dibromo-1,4-dimethylpiperazine-2,5-dione (2) (crude 1.05 mg, 3.52 mmol) was dissolved in dichloromethane (DCM; 100 ml), potassium thioacetate (1.2 g, 3.0 eq.) was added thereto in an ice water bath. The mixture was stirred overnight at room temperature, and the obtained precipitates were filtered and washed with DCM. The filtrates were combined and the solvent was evaporated under vacuum. The residue was purified using silica gel column chromatography (DCM:ethyl acetate (EA)=5:1) to obtain 1,4-dimethyl-3,6-dioxopiperazine-2,5-diyl-diethanethioate (3) (white solids; 200 mg, 2 step yield-20%).

$^1$H NMR (400 MHz, CDCl$_3$): δ ppm 5.77 (s, 2H), 2.94 (s, 6H), 2.48 (s, 6H).

C. 3,6-dimercapto-1,4-dimethylpiperazine-2,5-dione (4)

After dithioacetate (195 mg, 0.67 mmol) was dissolved in ethanol (20 ml), an ethanolic hydrochloric acid solution (prepared by adding 1.5 ml of acetyl chloride to 7 ml of ethanol) was added thereto. The mixture solution was heated under reflux for 2 hours. After the reaction was complete, the solvent was removed, and the residue was dried under reduced pressure to obtain 3,6-dimercapto-1,4-dimethylpiperazine-2,5-dione (4) in bright yellow solids (90 mg, 65%). The obtained compound was used for the next reaction without further purification.

$^1$H NMR (400 MHz, CDCl$_3$): δ ppm 5.00 (s, 2H), 3.09 (s, 6H).

ESI-MS (M-1): 205 calculated for C$_6$H$_{10}$N$_2$O$_2$S$_2$ 206.

D. 5,7-dimethyl-2,3-dithio-5,7-diazabicyclo[2,2,2]octane-6,8-dione (5; A2)

A solution in which iodine (63 mg, 1.0 eq.) was dissolved in 10 ml of DCM was added to a solution in which 3,6-dimercapto-1,4-dimethylpiperazine-2,5-dione (50 mg, 0.242 mmol) was dissolved in 10 ml of chloroform. The mixture was reacted for 30 minutes at room temperature. After the reaction was complete, a saturated NaHCO$_3$ solution containing sodium thiosulfate was poured into the reaction material, and the result was stirred until the color due to iodine disappeared. After the organic layer was separated and the aqueous layer was further extracted twice with DCM, the organic layers were combined and then dried with magnesium sulfate. After that, the organic layer was filtered and vacuum concentrated to give a residue, and the residue was recrystallized using ethanol, filtered, then washed with hexane (Hex), and dried under reduced pressure to otabin 5,7-dimethyl-2,3-dithio-5,7-diazabicyclo[2,2,2]octane-6,8-dione (5) in bright yellow solids (18 mg, 36%). The NMR data of the obtained final product was shown in FIG. 36.

$^1$H NMR (400 MHz, CDCl$_3$): δ ppm 5.21 (s, 2H), 3.12 (s, 6H).

ESI-MS (M+Na): 227 calculated for C$_6$H$_8$N$_2$O$_2$S$_2$ 204.

Preparation Example 3: Preparation of 1,5,7-trimethyl-2,3-dithia-5,7-diazabicyclo[2.2.2]octane-6,8-dione (A3, Chemical Formula 8)

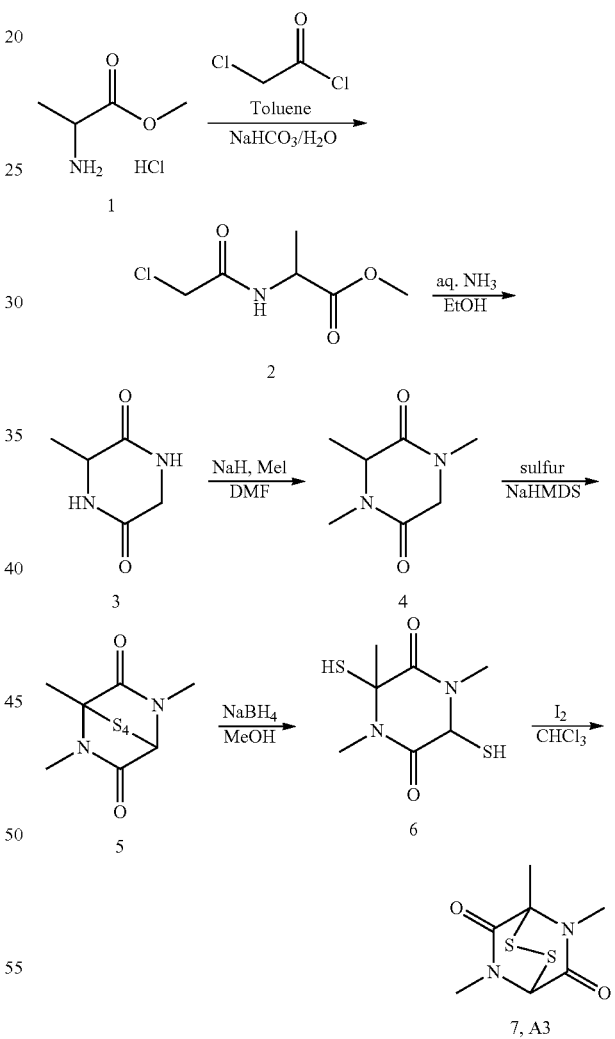

A. methyl 2-(2-chloroacetamido)propanoate (2)

After alanine methyl ester hydrochloride (2 g, 14.3 mmol) was dissolved in 6 ml of water, sodium bicarbonate (NaHCO$_3$; 2.8 g, 33.6 mmol) was slowly added thereto in an ice water bath. To the reaction material, a chloroacetyl chloride (1.67 ml, 20.9 mmol) solution dissolved in 5 ml of toluene was mixed by being added drop by drop, and the result was vigorously stirred for 3 hours at room temperature. After the reaction was complete, the organic layer was separated and the aqueous layer was further washed with toluene. The organic layers were combined, treated with magnesium sulfate, filtered, and then the solvent was removed. The residue was dried under reduced pressure to obtain crude methyl 2-(2-chloroacetamido)propanoate (2) (2.6 g).

$^1$H NMR (400 MHz, CDCl$_3$): δ ppm 7.23 (br s, 1H), 4.65 (m, 1H), 4.11 (s, 2H), 3.79 (s, 3H), 1.42 (d, 3H).

B. 3-methylpiperazine-2,5-dione (3)

After methyl 2-(2-chloroacetamido)propanoate (2; 2.6 g, 14.3 mmol) was dissolved in 12 ml of ethanol, 6.1 ml (43.4 mmol) of a 30% aqueous ammonia solution was added thereto. The mixture was reacted for 5 hours at 70° C. After the reaction was complete and the reaction material was cooled to room temperature, ethanol was removed. When solids were formed in the remaining small amount of water, the solids were filtered and then washed with water and hexane. The washed solids were dried under reduced pressure to obtain 3-methylpiperazine-2,5-dione (3) in white solids (420 mg, 2 step yield-23%).

$^1$H NMR (400 MHz, DMSO-d6): δ ppm 8.13 (br s, 1H), 7.95 (br s, 1H), 3.84 (q, 1H), 3.72 (s, 2H), 1.26 (d, 3H).

C. 1,3,4-trimethylpiperazine-2,5-dione (4)

After 3-methylpiperazine-2,5-dione (3; 420 mg, 3.28 mmol) was dispersed in 25 ml of dimethylformamide (DMF), NaH (400 mg, 9.83 mmol) was added thereto in an ice water bath. Methyl iodide (2 ml, 10 eq.) was added thereto, and the mixture was stirred for 4 hours at room temperature. After the reaction was complete, DMF was removed and the residue was purified using silica gel column chromatography (DCM:methanol=20:1 to 9:1) to obtain 1,3,4-trimethylpiperazine-2,5-dione (4) (colorless solids; 440 mg, yield 86%).

$^1$H NMR (400 MHz, CDCl$_3$): δ ppm 4.08 (d, 1H), 3.92 (q, 1H), 3.85 (d, 1H), 2.98 (s, 6H), 1.47 (d, 3H).

D. 6,7,9-trimethyl-2,3,4,5-tetrathia-7,9-diazabicyclo[4.2.2]decane-8,10-dione (5)

After sulfur (1.64 g, 51.2 mmol) was dispersed in 20 ml of dry THF, NaHMDS (1.0 M in THF, 19.2 ml) was added thereto drop by drop over 2 minutes under argon atmosphere. After the mixture was stirred for approximately 1 minute, a solution in which the compound (4; 1 g, 6.4 mmol) obtained in Step C was dissolved in 20 ml of THF was added thereto drop by drop. After the result was stirred for approximately 1 minute, NaHMDS (1.0 M in THF, 12.8 ml, 2.0 eq.) was added thereto drop by drop, and then the result was stirred for 30 minutes. After the reaction was complete, the result was extracted by adding a saturated NH$_4$Cl solution and DCM (×3). The organic layers were combined, treated with magnesium sulfate, filtered, and then the solvent was removed. The residue was purified using silica gel column chromatography (EA:hexane=1:1) to obtain 6,7,9-trimethyl-2,3,4,5-tetrathia-7,9-diazabicyclo[4.2.2]decane-8,10-dione (5; 250 mg, yield: 14%).

$^1$H NMR (400 MHz, CDCl$_3$): δ ppm 5.13 (s, 1H), 3.06 (d, 6H), 2.00 (s, 3H).

E. 3,6-dimercapto-1,3,4-trimethylpiperazine-2,5-dione (6)

After 6,7,9-trimethyl-2,3,4,5-tetrathia-7,9-diazabicyclo[4.2.2]decane-8,10-dione (5) (250 mg, 0.885 mmol) was dissolved in 20 ml of methanol, the result was slowly added to NaBH$_4$ (167 mg, 4.43 mmol) in an ice water bath. After the mixture was stirred for 30 minutes and the reaction was complete, the solvent was removed. Water and DCM (×3) were added to the crude compound and the result was extracted. The organic layers were combined, treated with magnesium sulfate, filtered, and then the solvent was removed. The residue was dried under reduced pressure to obtain 3,6-dimercapto-1,3,4-trimethylpiperazine-2,5-dione (6). The compound was used for the next reaction without further purification.

F. 1,5,7-trimethyl-2,3-dithia-5,7-diazabicyclo[2.2.2]octane-6,8-dione (7; A3)

After the dithiol compound (35 mg) obtained above was dissolved in 30 ml of chloroform, 25 ml of a solution in which iodine (249 mg, 1.0 eq.) was dissolved in chloroform was added thereto. After the mixture was reacted for 30 minutes at room temperature, the solvent was removed, and the residue was purified using silica gel column chromatography (EA:Hex=1:1) to obtain 1,5,7-trimethyl-2,3-dithia-5,7-diazabicyclo[2.2.2]octane-6,8-dione (7) in bright yellow solids (24 mg, 2 step yield-12%). The NMR data of the obtained final product was shown in FIG. 38.

$^1$H NMR (400 MHz, CDCl$_3$): δ ppm 5.29 (s, 1H), 3.14 (s, 3H), 3.03 (s, 1H), 1.98 (s, 3H).

ESI-MS (M+Na): 241 calculated for C$_7$H$_{10}$N$_2$O$_2$S$_2$ 218.

Preparation Example 4: Preparation of 1,4-bis(4-methoxybenzyl)-2,3-dithia-5,7-diazabicyclo[2.2.2]octane-6,8-dione (A4, Chemical Formula 9)

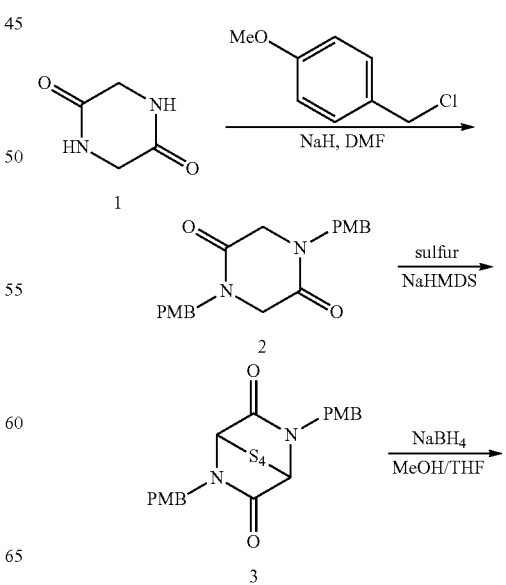

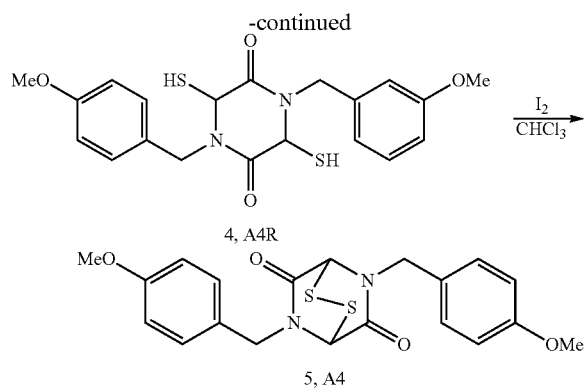

4, A4R

5, A4

A. 1,4-bis(4-methoxybenzyl)piperazine-2,5-dione (2)

After NaH (1.54 g, 38.5 mmol) was dispersed in 20 ml of DMF, anhydrous glycine (2 g, 17.5 mmol) was added thereto in an ice water bath. After the mixture was stirred for 10 minutes, benzyl chloride (5.94 ml, 2.5 eq) was slowly added thereto over 30 minutes. After the result was reacted for 1 hour at room temperature, water was added thereto and the result was stirred. The precipitates were filtered and then washed with water. The solid compound obtained was stirred in a mixed solvent of EA and hexane (EA:Hex=9:1), filtered and then dried under reduced pressure to obtain 1,4-bis(4-methoxybenzyl)piperazine-2,5-dione (2; 5.1 g, 82%).

$^1$H NMR (400 MHz, CDCl$_3$): δ ppm 7.21 (d, 4H), 6.87 (d, 4H), 4.51 (s, 4H), 3.89 (s, 4H), 3.80 (s, 6H).

B. 7,9-bis(4-methoxybenzyl)-2,3,4,5-tetrathia-7,9-diazabicyclo[4.2.2]decane-8,10-dione (3)

After sulfur (72 mg, 2.257 mmol) was dispersed in 2 ml of dry THF, NaHMDS (1.0 M in THF, 0.85 ml, 3.0 eq.) was added thereto drop by drop over 2 minutes under argon atmosphere. After the mixture was stirred for approximately 1 minute, a solution in which the compound (2; 100 mg, 0.282 mmol) obtained in Step A was dissolved in 20 ml of THF was added thereto drop by drop. After the result was stirred for approximately 1 minute, NaHMDS (1.0 M in THF, 0.56 ml, 2.0 eq.) was added thereto drop by drop, and the result was stirred for 30 minutes. After the reaction was complete, the result was extracted by adding a saturated NH$_4$Cl solution and EA (×2). The organic layers were combined, treated with magnesium sulfate, filtered, and then the solvent was removed. The residue was purified using silica gel column chromatography (Hex:EA=4:1 to 2:1) to obtain 7,9-bis(4-methoxybenzyl)-2,3,4,5-tetrathia-7,9-diazabicyclo[4.2.2]decane-8,10-dione (3; 35 mg, yield: 26%).

$^1$H NMR (400 MHz, CDCl$_3$): δ ppm 7.21 (d, 4H), 6.87 (d, 4H), 5.37 (d, 2H), 4.99 (s, 2H), 3.84 (d, 2H), 3.81 (s, 6H).

C. 3,6-dimercapto-1,4-bis(4-methoxybenzyl)piperazine-2,5-dione (4)

After 7,9-bis(4-methoxybenzyl)-2,3,4,5-tetrathia-7,9-diazabicyclo[4.2.2]decane-8,10-dione (3) (420 mg, 0.873 mmol) was dissolved in 20 ml of methanol, the result was slowly added to NaBH$_4$ (99 mg, 3.0 eq.) in an ice water bath. After the mixture was stirred for 30 minutes and the reaction was complete, the solvent was removed. Water and EA (×3) were added to the crude compound and the result was extracted. The organic layers were combined, treated with magnesium sulfate, filtered, and then the solvent was removed. The residue was dried under reduced pressure to obtain 3,6-dimercapto-1,4-bis(4-methoxybenzyl)piperazine-2,5-dione (4). The compound was used for the next reaction without further purification.

$^1$H NMR (400 MHz, CDCl$_3$): δ ppm 7.20 (d, 4H), 6.89 (d, 4H), 5.21 (d, 2H), 4.93 (s, 2H), 4.12 (d, 2H), 3.85 (s, 6H), 3.05 (br s, 2H).

ESI-MS (M+Na): 441 calculated for C$_{20}$H$_{22}$N$_2$O$_4$S$_2$ 418.

D. 5,7-bis(4-methoxybenzyl)-2,3-dithia-5,7-diazabicyclo[2.2.2]octane-6,8-dione (5; A4)

After the dithiol compound (4; 380 mg) obtained above was dissolved in 50 ml of chloroform, 100 ml of a solution in which iodine (221 mg, 0.873 mmol) was dissolved in chloroform was added thereto. After the mixture was reacted for 30 minutes at room temperature, the solvent was removed, and the residue was purified using silica gel column chromatography (EA:Hex=1:1) to obtain 5,7-bis(4-methoxybenzyl)-2,3-dithia-5,7-diazabicyclo[2.2.2]octane-6,8-dione (5) (120 mg, 2 step yield-33%). The NMR data of the obtained final product was shown in FIG. 39.

$^1$H NMR (400 MHz, CDCl$_3$): δ ppm 7.22 (d, 4H), 6.91 (d, 4H), 5.21 (s, 2H), 4.77 (d, 2H), 4.45 (d, 2H), 3.81 (s, 6H).

ESI-MS (M+Na): 439 calculated for C$_{20}$H$_{20}$N$_2$O$_4$S$_2$ 416.

Preparation Example 5: Preparation of 5,7-diallyl-2,3-dithia-5,7-diazabicyclo[2.2.2]octane-6,8-dione (A5, Chemical Formula 10)

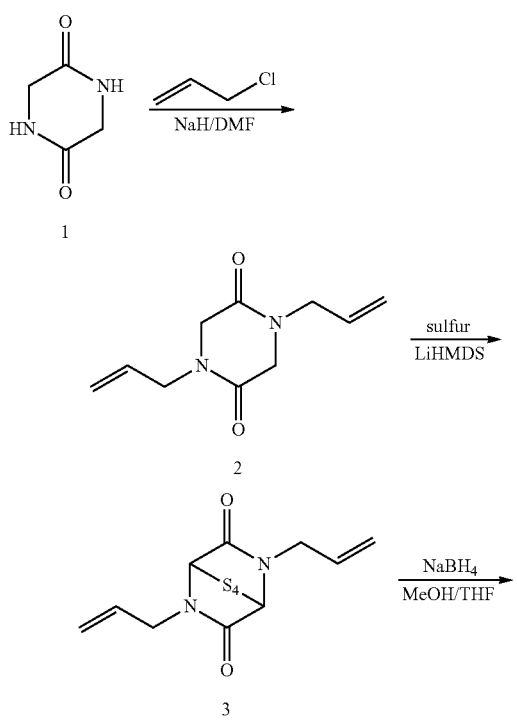

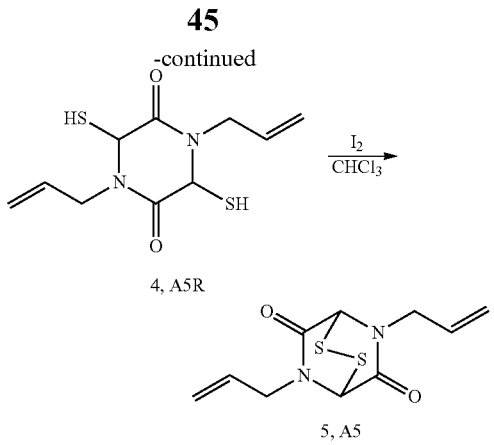

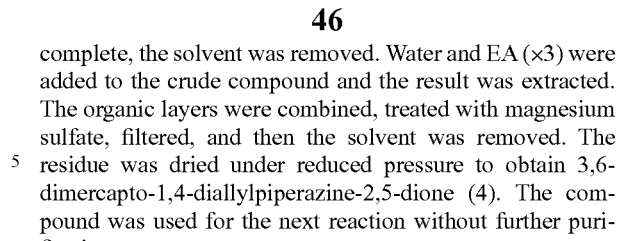

A. 1,4-diallylpiperazine-2,5-dione (2)

After NaH (1.3 g, 32.8 mmol) was dispersed in 25 ml of DMF, anhydrous glycine (1.5 g, 13.1 mmol) was added thereto in an ice water bath. After the mixture was stirred for 10 minutes, allyl chloride (3.2 ml, 3.0 eq.) was slowly added thereto over 30 minutes. The result was reacted for 1 hour at room temperature, and then the reaction solution was extracted by adding EA (×2) and a saturated NH$_4$Cl solution. The organic layers were combined, treated with magnesium sulfate, filtered, and then the solvent was removed. The residue was purified using silica gel column chromatography (DCM:EA=1:1) to obtain 1,4-diallylpiperazine-2,5-dione (2) (1.4 g, yield 56%).

$^1$H NMR (400 MHz, CDCl$_3$): δ ppm 5.79-5.69 (m, 2H), 5.30-5.22 (m, 4H), 4.04 (d, 4H), 3.96 (s, 4H).

B. 7,9-diallyl-2,3,4,5-tetrathia-7,9-diazabicyclo[4.2.2]decane-8,10-dione (3)

After sulfur (1.32 g, 41.2 mmol) was dispersed in 10 ml of dry THF, NaHMDS (1.0 M in THF, 15.4 ml, 3.0 eq.) was added thereto drop by drop over 2 minutes under argon atmosphere. After the mixture was stirred for approximately 1 minute, a solution in which the compound (2; 1 g, 5.15 mmol) obtained in Step A was dissolved in 20 ml of THF was added thereto drop by drop. After the result was stirred for approximately 1 minute, NaHMDS (1.0 M in THF, 10.3 ml, 2.0 eq.) was added thereto drop by drop, and the result was stirred for 30 minutes. After the reaction was complete, the result was extracted by adding a saturated NH$_4$Cl solution and EA (×3). The organic layers were combined, treated with magnesium sulfate, filtered, and then the solvent was removed. The residue was purified using silica gel column chromatography (Hex:EA=9:1 to 4:1) to obtain 7,9-diallyl-2,3,4,5-tetrathia-7,9-diazabicyclo[4.2.2]decane-8,10-dione (3; 530 mg, yield: 32%).

$^1$H NMR (400 MHz, CDCl$_3$): δ ppm 5.83-5.73 (m, 2H), 5.40-5.33 (m, 4H), 5.21 (s, 2H), 4.81 (d, 2H), 3.51-3.45 (m, 2H).

C. 3,6-dimercapto-1,4-diallylpiperazine-2,5-dione (4)

After 7,9-diallyl-2,3,4,5-tetrathia-7,9-diazabicyclo[4.2.2]decane-8,10-dione (3) (530 mg, 1.65 mmol) was dissolved in a methanol/THF mixed solvent, NaBH$_4$ (187 mg, 3.0 eq.) was slowly added thereto in an ice water bath. After the mixture was stirred for 30 minutes and the reaction was complete, the solvent was removed. Water and EA (×3) were added to the crude compound and the result was extracted. The organic layers were combined, treated with magnesium sulfate, filtered, and then the solvent was removed. The residue was dried under reduced pressure to obtain 3,6-dimercapto-1,4-diallylpiperazine-2,5-dione (4). The compound was used for the next reaction without further purification.

$^1$H NMR (400 MHz, CDCl$_3$): δ ppm 5.80-5.70 (m, 2H), 5.39-5.31 (m, 4H), 5.07 (s, 2H), 4.68 (d, 2H), 3.70-3.64 (m, 2H), 3.09 (br s, 2H).

D. 5,7-diallyl-2,3-dithia-5,7-diazabicyclo[2.2.2]octane-6,8-dione (5; A5)

After the dithiol compound (4; 430 mg) obtained above was dissolved in 30 ml of chloroform, 60 ml of a solution in which iodine (419 mg, 1.0 eq.) was dissolved in chloroform was added thereto. After the mixture was reacted for 30 minutes at room temperature, the solvent was removed, and the residue was purified using silica gel column chromatography (EA:Hex=1:9 to 1:4) to obtain 5,7-diallyl-2,3-dithia-5,7-diazabicyclo[2.2.2]octane-6,8-dione (5) (110 mg, 2 step yield-26%). The NMR data of the obtained final product was shown in FIG. 41.

$^1$H NMR (400 MHz, CDCl$_3$): δ ppm 5.86-5.81 (m, 2H), 5.38-5.34 (m, 4H), 5.30 (s, 2H), 4.32-4.27 (m, 2H), 4.00-3.95 (m, 2H).

ESI-MS (M+K): 295 calculated for C$_{10}$H$_{12}$N$_2$O$_2$S$_2$ 256.

Preparation Example 6: Preparation of 5-(4-methoxybenzyl)-2,3-dithia-5,7-diazabicyclo[2.2.2]octane-6,8-dione (A6, Chemical Formula 11)

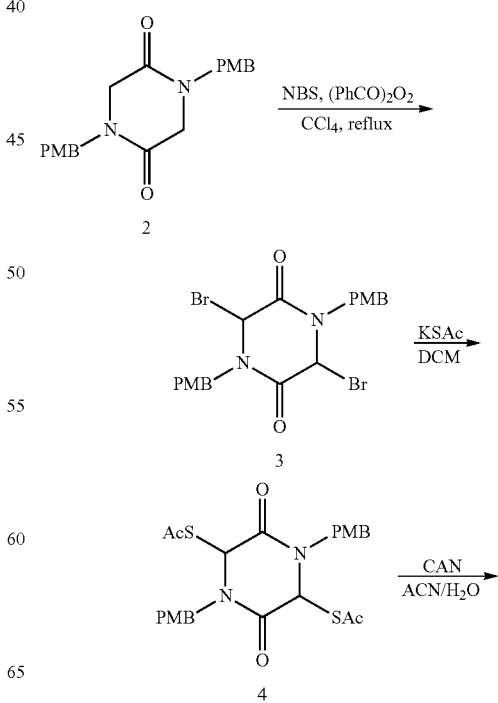

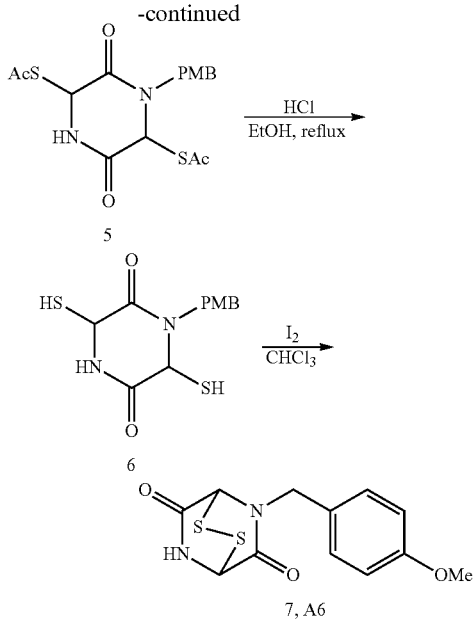

A. 1,4-bis(4-methoxybenzyl)piperazine-2,5-dione (2)

1,4-Bis(4-methoxybenzyl)piperazine-2,5-dione (2) was obtained in the same manner as in Step A of Preparation Example 3.

B. 3,6-dibromo-1,4-bis(4-methoxybenzyl)piperazine-2,5-dione (3)

After 1,4-bis(4-methoxybenzyl)piperazine-2,5-dione (2; 1 g, 2.82 mmol), N-bromosuccimide (1.05 g, 2.1 eq.) and benzoyl peroxide (6.8 mg, 0.01 eq.) were dispersed in carbon tetrachloride (250 ml), the mixture was reacted for 2 hours while being refluxed. After the reaction was complete and the reaction material was cooled to room temperature, the produced solids were filtered. The solvent was removed, and the result was dried under reduced pressure to obtain 3,6-dibromo-1,4-bis(4-methoxybenzyl)piperazine-2,5-dione (3). The obtained compound was used as it is for the next reaction without further purification.
$^1$H NMR (400 MHz, CDCl$_3$): δ ppm 7.22 (d, 4H), 6.89 (d, 4H), 5.89 (s, 2H), 5.30 (d, 2H), 3.93 (d, 2H), 3.82 (s, 6H).

C. 1,4-bis(4-methoxybenzyl)-3,6-dioxopiperazine-2,5-diyl-diethanethioate (4)

After 3,6-dibromo-1,4-bis(4-methoxybenzyl)piperazine-2,5-dione (3; 1.44 g, 2.82 mmol) was dissolved in dichloromethane (DCM; 100 ml), sodium thioacetate (966 mg, 3.0 eq.) was added thereto in an ice water bath. The mixture was stirred overnight at room temperature, and the obtained precipitates were filtered, and the solvent was removed. The result was purified using silica gel column chromatography (Hex:EA=2:1 to 1.5:1) to obtain 1,4-bis(4-methoxybenzyl)-3,6-dioxopiperazine-2,5-diyl-diethanethioate (4) (600 mg, 2 step yield-43%).
$^1$H NMR (400 MHz, CDCl$_3$): δ ppm 7.22 (d, 4H), 6.86 (d, 4H), 5.83 (s, 2H), 4.98 (d, 2H), 3.89 (d, 2H), 3.81 (s, 6H), 2.45 (s, 6H).

D. 1-(4-methoxybenzyl)-3,6-dioxopiperazine-2,5-diyl-diethanethioate (5)

After 1,4-bis(4-methoxybenzyl)-3,6-dioxopiperazine-2,5-diyl-diethanethioate (4; 1.37 g, 2.73 mmol) was dissolved in an ACN/H$_2$O (90 ml/20 ml) mixed solvent, ceric ammonium nitrate ((NH$_4$)$_2$Ce(NO$_3$)$_6$; CAN, 4.5 g, 3.0 eq) was added thereto, and the mixture was stirred for 2 hours. After the organic solvent was removed, the result was extracted by adding DCM (×2) and water. The organic solvent was treated with magnesium sulfate, filtered, and then the solvent was removed. The residue was purified using silica gel column chromatography (Hex:EA=2:1 to 1.5:1) to obtain 1-(4-methoxybenzyl)-3,6-dioxopiperazine-2,5-diyl-diethanethioate (5; 380 mg, 36%).
$^1$H NMR (400 MHz, CDCl$_3$): δ ppm 7.27 (d, 2H), 6.88 (d, 2H), 6.73 (br s, 1H), 5.78-5.74 (m, 2H), 5.12 (d, 1H), 3.81 (s, 3H), 3.78 (d, 1H), 2.46 (s, 6H)

E. 3,6-dimercapto-1-(4-methoxybenzyl)piperazine-2,5-dione (6)

After the dithioacetate (5; 150 mg, 0.392 mmol) was dispersed in ethanol (20 ml), an ethanolic hydrochloric acid solution (prepared by adding 1.5 ml of acetyl chloride to 7 ml of ethanol) was added thereto. The mixture solution was reacted for 2 hours while being refluxed. After the reaction was complete, the solvent was removed, and the residue was dried under reduced pressure to obtain 3,6-dimercapto-1-(4-methoxybenzyl)piperazine-2,5-dione (6). The obtained compound was used for the next reaction without further purification.

F. 5-(4-methoxybenzyl)-2,3-dithia-5,7-diazabicyclo[2.2.2]octane-6,8-dione (7; A6)

A solution in which iodine (99.5 mg, 1.0 eq.) was dissolved in 15 ml of DCM was added to a solution in which 3,6-dimercapto-1-(4-methoxybenzyl)piperazine-2,5-dione (6; 117 mg, 0.392 mmol) was dissolved in 20 ml of DCM. The mixture was reacted for 30 minutes at room temperature. After the reaction was complete, the solvent was removed, and the residue was purified twice using silica gel column chromatography (Hex:EA=1:1) to obtain 5-(4-methoxybenzyl)-2,3-dithia-5,7-diazabicyclo[2.2.2]octane-6,8-dione (7) (4 mg). The NMR data of the obtained final product was shown in FIG. 43.
$^1$H NMR (400 MHz, CDCl$_3$): δ ppm 7.23 (d, 2H), 7.15 (br s, 1H), 6.89 (d, 2H), 5.39 (d, 1H), 5.14 (s, 1H), 4.84 (d, 1H), 4.45 (d, 1H), 3.81 (s, 3H).
ESI-MS (M+Na): 319 calculated for C$_{12}$H$_{12}$N$_2$O$_3$S$_2$ 296.

Preparation Example 7: Preparation of 5,7-dibenzhydryl-2,3-dithia-5,7-diazabicyclo[2.2.2]octane-6,8-dione (A7, Chemical Formula 12)

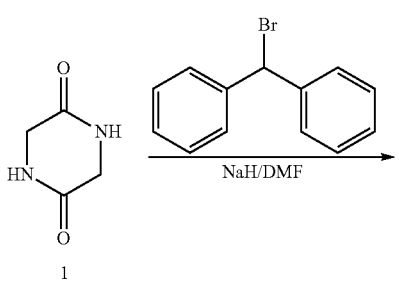

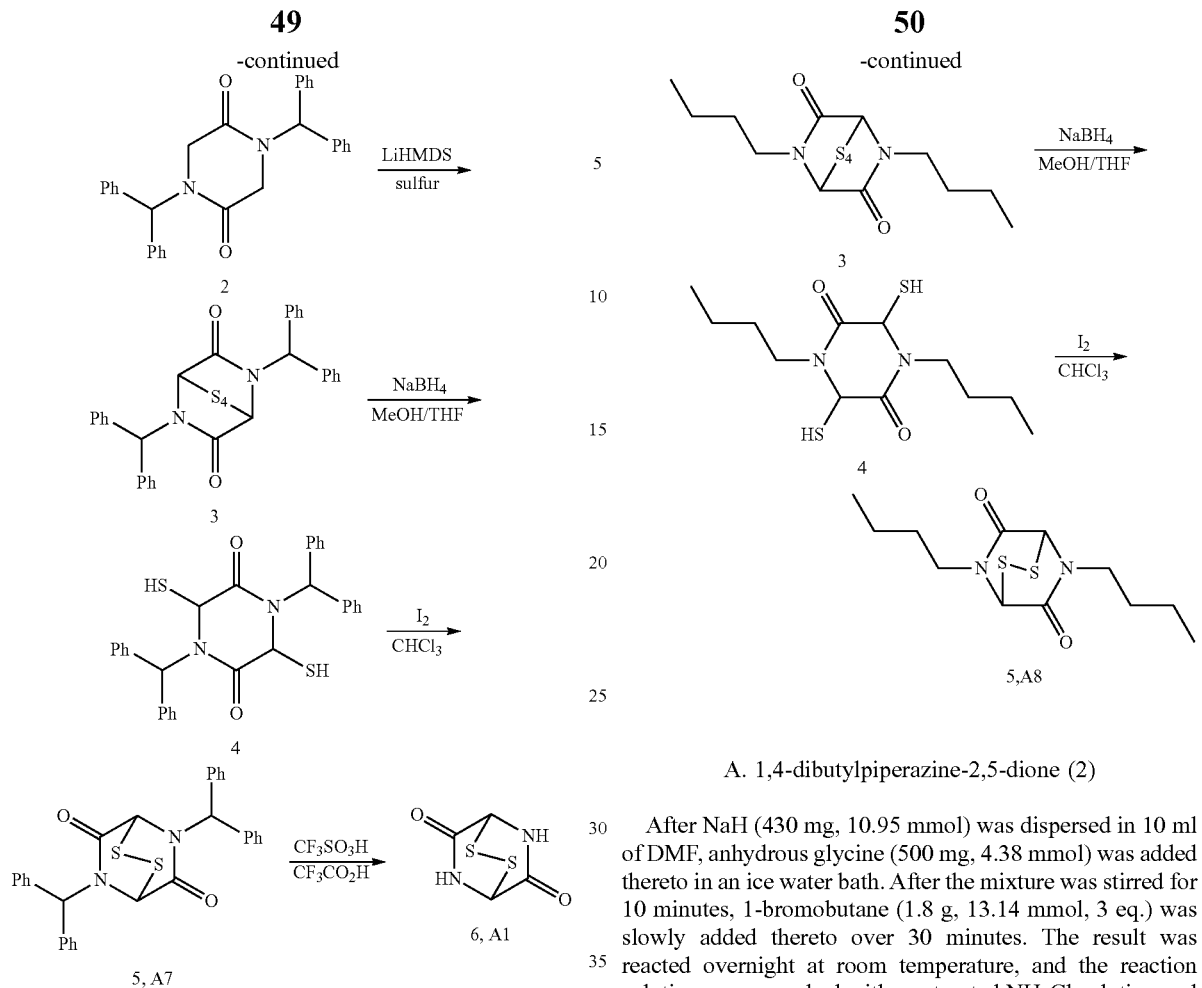

5,7-Dibenzhydryl-2,3-dithia-5,7-diazabicyclo[2.2.2]octane-6,8-dione was obtained in the same manner as in Steps A to D of Preparation Example 1. The NMR data of the obtained final product was shown in FIG. 44.

$^1$H NMR (400 MHz, CDCl$_3$): δ ppm 7.37-7.28 (m, 12H), 7.27 (m, 4H), 7.14 (m, 4H), 6.77 (s, 2H), 5.31 (s, 2H).

ESI-MS (M+Na): 531 calculated for C$_{30}$H$_{24}$N$_2$O$_2$S$_2$ 508.

Preparation Example 8: Preparation of 5,7-dibutyl-2,3-dithia-5,7-diazabicyclo[2.2.2]octane-6,8-dione (A8, Chemical Formula 13)

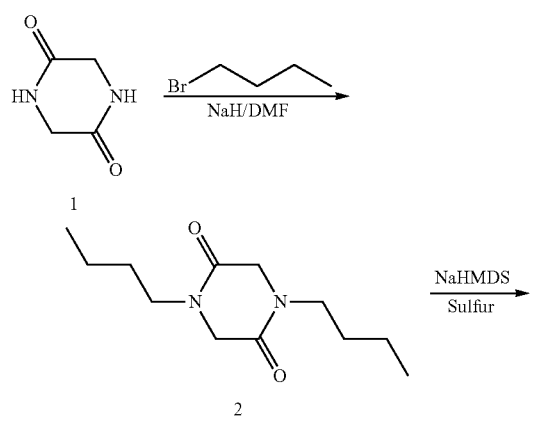

A. 1,4-dibutylpiperazine-2,5-dione (2)

After NaH (430 mg, 10.95 mmol) was dispersed in 10 ml of DMF, anhydrous glycine (500 mg, 4.38 mmol) was added thereto in an ice water bath. After the mixture was stirred for 10 minutes, 1-bromobutane (1.8 g, 13.14 mmol, 3 eq.) was slowly added thereto over 30 minutes. The result was reacted overnight at room temperature, and the reaction solution was quenched with a saturated NH$_4$Cl solution and then extracted with EA (×2). The organic layers were combined, washed with water, dried with magnesium sulfate, and then filtered. The filtrate was concentrated under reduced pressure and the residue was purified using silica gel column chromatography (DCM:EA=1:1) to obtain 1,4-dibutylpiperazine-2,5-dione (2) (410 mg, yield 41%, yellow oil).

$^1$H NMR (400 MHz, CDCl$_3$): δ ppm 3.95 (s, 4H), 3.39 (t, 4H), 1.54 (m, 4H), 1.34 (m, 4H), 0.94 (t, 6H).

B. 7,9-dibutyl-2,3,4,5-tetrathia-7,9-diazabicyclo[4.2.2]decane-8,10-dione (3)

After sulfur (450 mg, 14.16 mmol) was dispersed in 5 ml of dry THF, LiHMDS (1.0 M in THF, 5.31 ml, 3.0 eq.) was added thereto drop by drop over 2 minutes under argon atmosphere. After the mixture was stirred for approximately 1 minute, a solution in which the compound (2; 400 mg, 1.567 mmol) obtained in Step A was dissolved in 20 ml of THF was added thereto drop by drop. After the result was stirred for approximately 1 minute, LiHMDS (1.0 M in THF, 3.54 ml, 2.0 eq.) was added thereto drop by drop, and the result was stirred for 30 minutes. After the reaction was complete, the result was extracted by adding a saturated NH$_4$Cl solution and EA (×3). The organic layers were combined, treated with magnesium sulfate, filtered, and then concentrated under reduced pressure. The result was purified using silica gel column chromatography (Hex:EA=3:1) to obtain 7,9-dibutyl-2,3,4,5-tetrathia-7,9-diazabicyclo[4.2.2]decane-8,10-dione (3; 100 mg, yield: 16%).

$^1$H NMR (400 MHz, CDCl$_3$): δ ppm 5.15 (s, 2H), 3.90 (m, 2H), 3.05 (m, 2H), 1.61 (m, 4H), 1.35 (m, 4H), 0.95 (t, 6H).

C. 3,6-dimercapto-1,4-dibutylpiperazine-2,5-dione (4)

After 7,9-dibutyl-2,3,4,5-tetrathia-7,9-diazabicyclo[4.2.2]decane-8,10-dione (3; 100 mg, 0.28 mmol) was dissolved in a methanol/THF mixed solvent (1:1), NaBH$_4$ (32 mg, 0.84 mmol, 3.0 eq.) was slowly added thereto in an ice water bath. After the mixture was stirred for 30 minutes and the reaction was complete, the solvent was removed. A saturated NH$_4$Cl solution and EA (×3) were added to the crude compound and the result was extracted. The organic layers were combined, dried with magnesium sulfate, filtered, and then concentrated under reduced pressure to obtain 3,6-dimercapto-1,4-dibutylpiperazine-2,5-dione (4). The compound was used for the next reaction without further purification.

$^1$H NMR (400 MHz, CDCl$_3$): δ ppm 5.03 (d, 2H), 3.80 (m, 2H), 3.21 (m, 2H), 1.63 (m, 4H), 1.37 (m, 4H), 0.96 (t, 6H).

D. 5,7-dibutyl-2,3-dithia-5,7-diazabicyclo[2.2.2]octane-6,8-dione (5; A8)

After the dithiol crude compound (4) obtained above was dissolved in 30 ml of chloroform, 20 ml of a solution in which iodine (86 mg, 0.34 mmol) was dissolved in chloroform was added thereto. The mixture was reacted for 30 minutes at room temperature, and the solvent was removed by being concentrated under reduced pressure, and the residue was purified using silica gel column chromatography (EA:Hex=1:3) to obtain 5,7-dibutyl-2,3-dithia-5,7-diazabicyclo[2.2.2]octane-6,8-dione (5) (26 mg, 2 step yield-32%). The NMR data of the obtained final product was shown in FIG. 45.

$^1$H NMR (400 MHz, CDCl$_3$): δ ppm 5.27 (s, 2H), 3.50 (m, 4H), 1.66 (m, 4H), 1.35 (m, 4H), 0.95 (t, 6H).

ESI-MS (M+Na): 311 calculated for C$_{12}$H$_{20}$N$_2$O$_2$S$_2$ 288.

Preparation Example 9: Preparation of 5,7-bis(3-methoxypropyl)-2,3-dithia-5,7-diazabicyclo[2.2.2]octane-6,8-dione (A9, Chemical Formula 14)

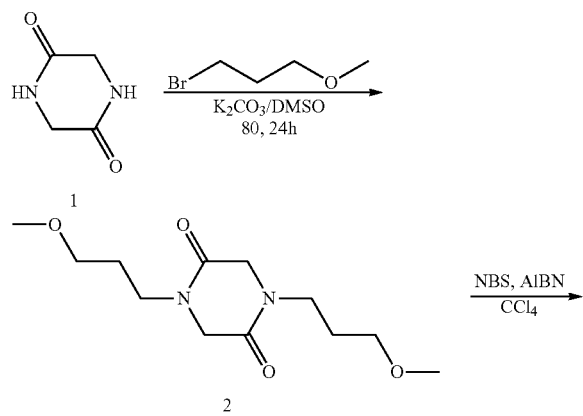

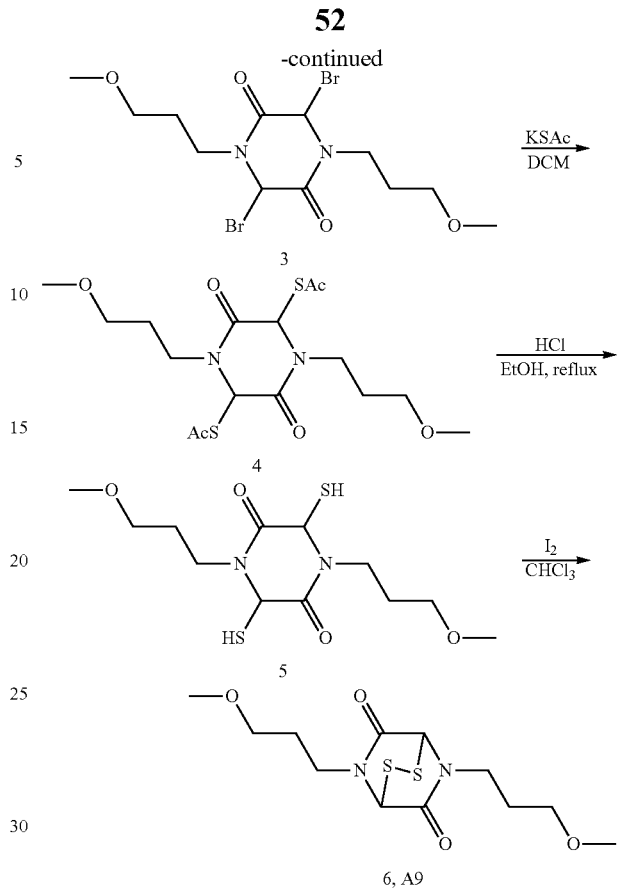

A. 1,4-bis(3-methoxypropyl)piperazine-2,5-dione (2)

After anhydrous glycine (0.5 g, 4.38 mmol) and K$_2$CO$_3$ (2.12 g, 15.33 mmol) were dispersed in 10 ml of DMSO, the temperature was raised to 80° C., and the mixture was stirred for 15 minutes at the temperature. 1-Chloro-3-methoxypropane (1.43 ml, 13.14 mmol) was slowly added thereto drop by drop. After the result was reacted for 24 hours at 80° C., the reaction was terminated, and the solids were filtered. The filtered solids were purified using silica gel column chromatography (DCM:MeOH=9:1) to obtain 1,4-bis(3-methoxypropyl)piperazine-2,5-dione (2) (350 mg, yield 31%). The residual DMSO was further washed with water.

$^1$H NMR (400 MHz, CDCl$_3$): δ ppm 3.98 (s, 4H), 3.48 (t, 4H), 3.41 (t, 4H), 3.32 (s, 6H), 1.84 (m, 4H).

B. 3,6-dibromo-1,4-bis(3-methoxypropyl)piperazine-2,5-dione (3)

After 1,4-bis(4-methoxypropyl)piperazine-2,5-dione (2; 200 mg, 0.77 mmol), N-bromosuccimide (276 mg, 1.55 mmol, 2.01 eq.) and azo-bis-isobutyronitrile (AIBN; 6.3 mg, 0.04 mmol, 0.05 eq.) were dispersed in carbon tetrachloride (50 ml), the mixture was reacted for 2 hours while being refluxed. After the reaction was complete and the reaction material was cooled to room temperature, the produced solids were filtered. The solvent was removed, and the result was dried under reduced pressure to obtain 3,6-dibromo-1,4-bis(3-methoxypropyl)piperazine-2,5-dione (3). The obtained compound was used as it is for the next reaction without further purification.

$^1$H NMR (400 MHz, CDCl$_3$): δ ppm 6.21 (s, 2H), 3.92 (m, 2H), 3.41 (m, 4H), 3.32 (s, 6H), 3.25 (m, 2H), 1.87 (m, 4H).

C. 1,4-bis(3-methoxypropyl)-3,6-dioxopiperazine-2,5-diyl-diethanethioate (4)

After 3,6-dibromo-1,4-bis(4-methoxypropyl)piperazine-2,5-dione (3; 400 mg, 0.96 mmol) was dissolved in 30 ml of DCM, sodium thioacetate (329 mg, 2.888 mmol, 3.0 eq.) was added thereto in an ice water bath. After the mixture was stirred overnight at room temperature, the produced solids were filtered and then the solvent was removed from the solution. The result were purified using silica gel column chromatography (EA:Hex=1:1 to 3:1) to obtain 1,4-bis(4-methoxypropyl)-3,6-dioxopiperazine-2,5-diyl-diethanethioate (4) (65 mg, 2 step yield-6.4%).

$^1$H NMR (400 MHz, CDCl$_3$): δ ppm 5.88 (s, 2H), 3.95 (m, 2H), 3.43 (m, 4H), 3.37 (s, 6H), 2.98 (m, 2H), 2.43 (s, 6H), 1.90 (m, 4H).

D. 3,6-dimercapto-1,4-bis(3-methoxypropyl)piperazine-2,5-dione (5)

After the dithioacetate (4; 40 mg, 0.1 mmol) was dispersed in ethanol, an ethanolic hydrochloric acid solution (prepared by adding 0.75 ml of acetyl chloride to 3.5 ml of ethanol) was added thereto drop by drop, and the mixture solution was reacted for 2 hours while being refluxed. After the reaction was complete and the reaction material was cooled to room temperature, the organic solvent was removed and the residue was dried to obtain 3,6-dimercapto-1,4-bis(methoxypropyl)piperazine-2,5-dione (5). The obtained compound was used for the next reaction without further purification.

$^1$H NMR (400 MHz, CDCl$_3$): δ ppm 5.08 (d, 2H), 3.89 (m, 2H), 3.41 (m, 4H), 3.35 (s, 6H), 3.23 (m, 2H), 3.18 (d, 2H), 1.93 (m, 4H).

E. 5,7-bis(3-methoxypropyl)-2,3-dithia-5,7-diazabicyclo[2.2.2]octane-6,8-dione (6; A9)

A solution in which iodine (20.3 mg, 0.08 mmol, 1.0 eq.) was dissolved in 15 ml of DCM was added to a solution in which 3,6-dimercapto-1,4-bis(methoxypropyl)piperazine-2,5-dione (5; 25 mg, 0.08 mmol) was dissolved in 10 ml of chloroform, and the mixture was reacted for 1 hour at room temperature. After the reaction was complete, the solvent was removed and the residue was purified using silica gel column chromatography (Hex:EA=1:1 to 1:2) to obtain 5,7-bis(methoxypropyl)-2,3-dithia-5,7-diazabicyclo[2.2.2]octane-6,8-dione (6) (9 mg, yield 36%). The NMR data of the obtained final product was shown in FIG. 46.

$^1$H NMR (400 MHz, CDCl$_3$): δ ppm 5.35 (s, 2H), 3.69 (m, 2H), 3.57-39 (m, 6H), 3.36 (s, 6H), 1.93 (m, 4H).

ESI-MS (M+Na): 343 calculated for C$_{12}$H$_{20}$N$_2$O$_4$S$_2$ 320.

Synthesis of Piperazinedione Derivative Including Reduced Dithiol Group

Preparation Example 10:
3,6-dimercapto-1,4-dimethylpiperazine-2,5-dione (A2R)

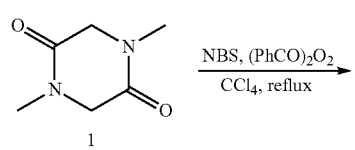

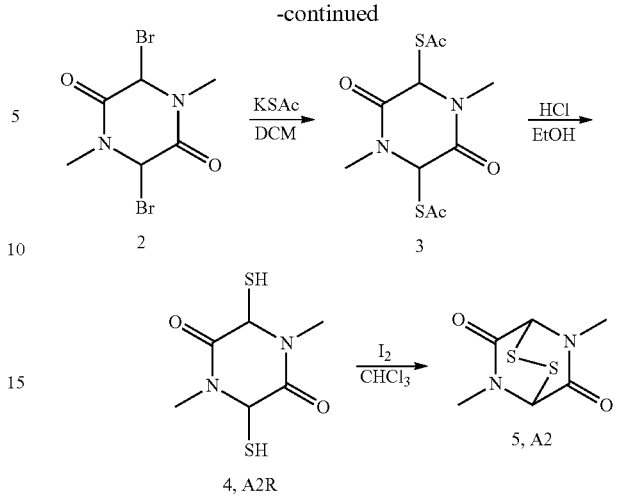

3,6-Dimercapto-1,4-dimethylpiperazine-2,5-dione was obtained in the same manner as in Steps A to C of Preparation Example 2. The NMR data of the obtained final product was shown in FIG. 37.

$^1$H NMR (400 MHz, CDCl$_3$): δ ppm 5.00 (s, 2H), 3.09 (s, 6H).

ESI-MS (M-1): 205 calculated for C$_6$H$_{10}$N$_2$O$_2$S$_2$ 206.

Preparation Example 11:
3,6-dimercapto-1,4-bis(4-methoxybenzyl)piperazine-2,5-dione (A4R)

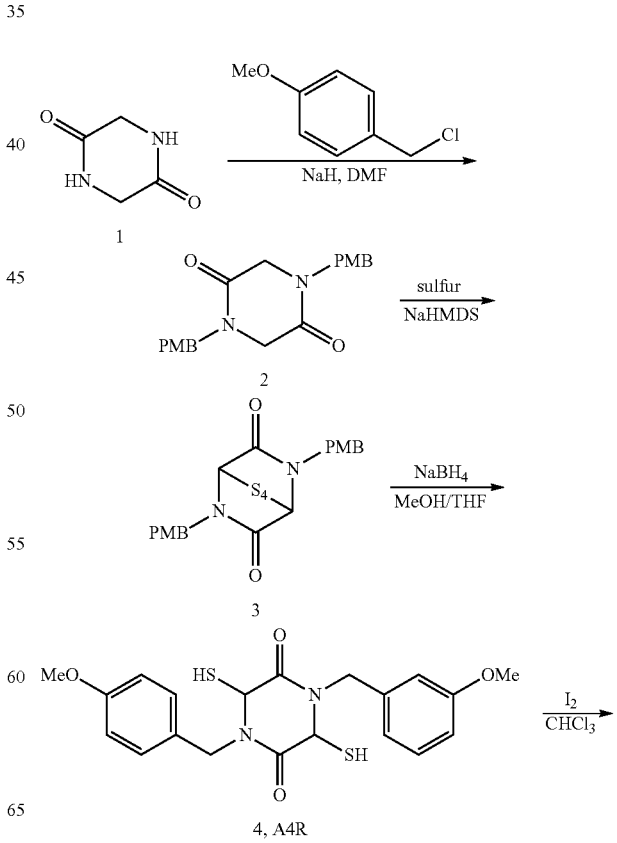

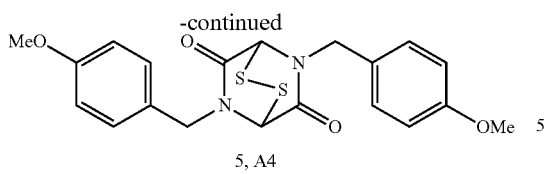

5, A4

3,6-Dimercapto-1,4-bis(4-methoxybenzyl)piperazine-2,5-dione was obtained in the same manner as in Steps A to C of Preparation Example 4. The NMR data of the obtained final product was shown in FIG. 40.

$^1$H NMR (400 MHz, CDCl$_3$): δ ppm 7.20 (d, 4H), 6.89 (d, 4H), 5.21 (d, 2H), 4.93 (s, 2H), 4.12 (d, 2H), 3.85 (s, 6H), 3.05 (br s, 2H).

ESI-MS (M+Na): 441 calculated for $C_{20}H_{22}N_2O_4S_2$ 418.

Preparation Example 12:
3,6-dimercapto-1,4-diallylpiperazine-2,5-dione (A5R)

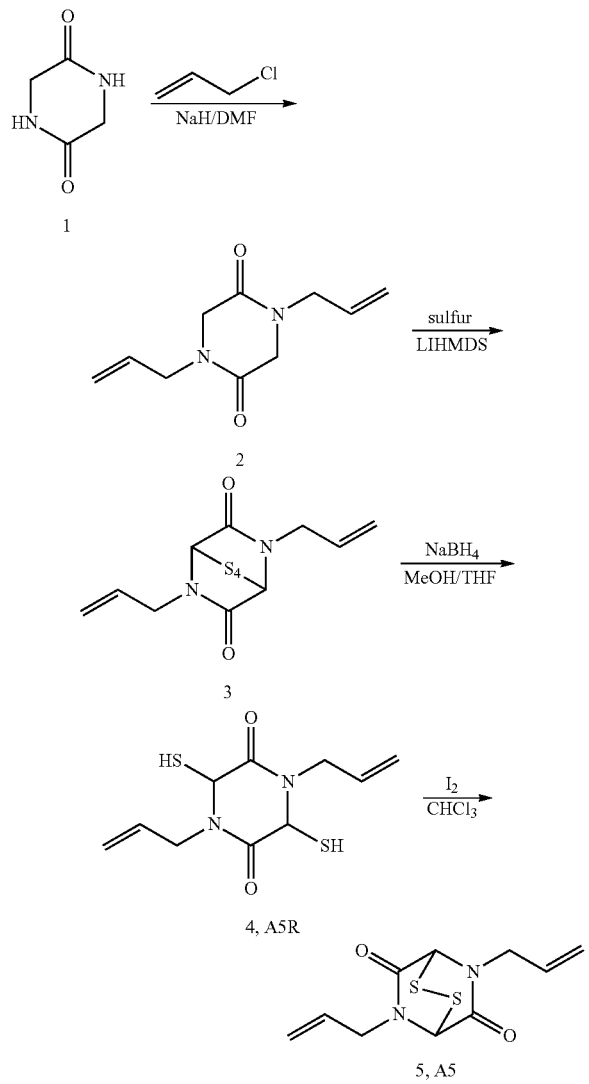

5, A5

3,6-Dimercapto-1,4-diallylpiperazine-2,5-dione was obtained in the same manner as in Steps A to C of Preparation Example 5. The NMR data of the obtained final product was shown in FIG. 42.

$^1$H NMR (400 MHz, CDCl$_3$): δ ppm 5.80-5.70 (m, 2H), 5.39-5.31 (m, 4H), 5.07 (s, 2H), 4.68 (d, 2H), 3.70-3.64 (m, 2H), 3.09 (br s, 2H).

Example 1: Materials

Anti-PrxI and PrxII antibodies were purchased from AbFrontier (Seoul, Korea). The sequence of the PrxII-specific siRNA used in the present invention was as follows: 5'-CGCUUGUCUGAGGAUUACGUU-3' (human PrxII siRNA-1, Prx2-1; sequence number 1), 5'-AGGAAUAUUUCUCCAAACAUU-3' (human PrxII siRNA-2, Prx2-2; sequence number 2), 5'-ACTCAACTGC-CAAGTGATTUU-3' (human PrxI siRNA, Prx1; sequence number 3) and 5'-AAAUCAAGCUUUCGGACUAUU-3' (mouse PrxII siRNA-1, mPrx2-1; sequence number 4). The siRNA oligonucleotide duplex was synthesized from Dharmacon. The firefly luciferase siRNA was synthesized and used as control siRNA. The siRNA duplex was transfected according to the protocol of the manufacturer using Lipofectamine RNAi MAX' (Invitrogen).

A SMART pool of four siRNA duplexes for rat PrxII (5'-GCAACGCGCACAUCGGAAAUU (sequence number 5), 5'-GAUCACAGUCAACGACCUAUU (sequence number 6), 5'-AGAAUUACGGCGUGUUGAAUU (sequence number 7) and 5'-ACGCUGAGGACUUCCGAAAUU (sequence number 8); Dharmacon Cat. no. D-089973) was used for rat carotid balloon injury experiments. The firefly luciferase siRNA was synthesized and used as control siRNA.

Gliotoxin, cheatocin and chetomin were purchased from Sigma-Aldrich. Bis(methylthio)gliotoxin was purchased from Santa Cruz Biotechnology. SU-5416 was purchased from Calbiochem. Phospho-PLCγ1 (pY783), PLCγ1, and phospho-VEGFR2 (pY1175) antibodies were purchased from Cell Signaling Technology. Anti-PDGFR-β (M-20) and KDR/Flk-1 (VEGFR2) antibodies were purchased from Santa Cruz Biotechnology. Anti-phosphotyrosine (4G10) and PDGF-BB were purchased from Upstate. VEGF-A (human VEGF$_{165}$) were purchased from R&D systems. Mouse anti-rat CD31 antibody was purchased from BD Bioscience. Alexa Fluor 488-conjugated donkey anti-rabbit and Alexa Fluor 568-conjugated donkey anti-mouse secondary antibodies were purchased from Invitrogen. Biotinylated goat anti-rabbit IgG, Avidin-HRP and DAB substrates were purchased from Vector Laboratories. PrxI, PrxII, Prx-SO$_{2/3}$, and phospho-PDGFRβ (pY857) rabbit polyclonal antibodies were prepared as described previously [M. H. Choi et al., 2005, Nature, 435: 347].

Example 2: Cell Culture

Human aortic endothelial cells (HAEC) and human aortic smooth muscle cells (HASMC) were purchased from Clonetics-Bio Whittaker (Venders, Belgium). The cells were seeded on a 0.1% gelatin-coated plate and grown at 37° C. in a humidified incubator including 5% carbon dioxide in Endothelial Basal Medium (EBM™-2) and Smooth Muscle Cell Basal Medium (SmBM™) SingleQuotes® including 10% fetal bovine serum (FBS) and full supplements (Cat no. cc-4176 for HAEC and Cat no. cc-4149 for HASMCs; Clonetics-BioWhittaker), respectively. Cells of passages 5 to 7 were used in the present invention.

Melanoma cell lines SK-MEL-5, A375 and B16F10 cells were grown at 37° C. in a CO$_2$ incubator using Dulbecco's Modified Eagle's Medium (DMEM) including 10% fetal bovine serum (FBS). SK-MEL-28 and G361 cells were grown in a RPMI 1640 medium including 10% FBS.

Human epidermal melanocyte was grown in Medium 254 (Cascade Biologics™) including human melanocyte growth supplements. The melanoma cell lines and the melanocyte used in the present invention were purchased from American Type Culture Collection.

Example 3: Peroxidase Activity Assay

The peroxidase activity assay for the epidithiodioxopiperazine derivatives according to the present invention (hereinafter, referred to as ETP compounds) was performed according to known methods [Korean Patent No. 10-0953326]. A standard peroxidase reaction for spectrophotometric assay was carried out using a 200 µl reaction mixture of 1 mM EDTA-containing 50 mM Hepes-NaOH buffer solution (pH 7.0) including 250 µM NADPH, 3 µM yeast thioredoxin (Trx), 1.5 µM yeast thioredoxin reductase (TR), 25 µM ETP compound and 1.2 ml of hydrogen peroxide. For the comparison with a glutathione (GSH)-dependent peroxidase reaction, GSH (1 mM) and yeast glutathione reductase (GSH reductase; GR) (1 Unit) were added instead of yeast Trx and TR. Each reaction was initiated by adding hydrogen peroxide, and the NADPH oxidation was monitored for 12 minutes at 30° C. according to absorbance decrease at 340 nm using an Agilent UV8453 spectrophotometer (Hewlett Packard, USA). The initial reaction rate was calculated using the linear portion of the curve and expressed as the amount of NADPH oxidized per minute.

Example 4: In Vitro Vascular Cell Function Assay

For cell proliferation assay, HAECs were divided at a concentration of 4000 cells/well in a final volume of 100 µl onto a 96-well plate including a siRNA-transfection reagent mixture. After siRNA-transfected for 24 hours, the cells were serum-starved for 18 hours, and then placed in an EBM-2 basal medium supplemented with VEGF-A165 (25 ng/ml, Cat no. 293-VE, R&D systems) for additional 24 hours. The extent of cell proliferation was measured using a WST-1 cell proliferation assay kit (Roche Diagnostics, USA), and the number of cells was expressed as absorbance at 450 nm, which was averaged from 3 wells after subtracting the turbidity at 600 nm.

The cell migration assay was performed in a 24-well Transwell culture chamber (Costar; 8-µm pore size). The bottom of the filter was coated with gelatin B (1 mg/ml) and air-dried for 1 hour. HAECs ($6 \times 10^3$) were added to upper chambers including siRNA-transfection complexes. After 24 hours, the siRNA-transfected HAECs were serum-starved overnight. A solution of VEGF-A (25 ng/ml) was prepared in a basal medium including 0.5% bovine serum albumin (BSA), and added to bottom chambers. The upper chamber wells were each filled with a basal medium including 0.5% BSA. The Transwell chamber was incubated for 8 hours under the condition of 37° C./5% carbon dioxide. After the incubation, the non-migrated cells at the top of the filter were removed, and the cells that migrated onto the bottom of filter were fixed and stained with 0.6% hematoxylin and 0.5% eosin. The stained cells were photographed and counted. The number of migrating cells was averaged from 3 wells.

Example 5: Immunoblot Analysis

The cells were rinsed with an ice-cold phosphate buffered saline (PBS) solution and then lysed in an extraction buffer solution containing 20 mM Hepes (pH 7.0), 1% Triton X-100, 150 mM NaCl, 10% glycerol, 1 mM EDTA, 2 mM EGTA, 1 mM DTT, 5 mM $Na_3VO_4$, 5 mM NaF, 1 mM AEBSF, aprotinin (5 µg/ml), and leupeptin (5 µg/ml). After being centrifuged at 12,000×g, the purified cell extracts were used for immunoblotting. In order to adjust the loading, the membranes were stripped by shaking them for 30 minutes at 60° C. in 67 mM Tris (pH 6.7), 2% SDS, and 100 mM 2-mercaptoethanol solution, and reprobed with an appropriate pan antibody.

Example 6: Immunocytochemistry

The cells were grown on a glass cover slide, and fixed with a prewarmed 4% paraformaldehyde solution for 15 minutes. The fixed cells were rinsed twice with PBS, and treated with 0.2% Triton X-100 for 30 minutes at room temperature so as to have cell permeability. After that, the cells were blocked for 1 hour using a PBS solution including 2% BSA, and incubated overnight at 4° C. with primary antibodies diluted in a blocking buffer solution: anti-phosphotyrosine (clone 4G10, 1:100), anti-Prx1 (1:300), anti-Prx2 (1:300), anti-β-catenin (1:200) and anti-E cadherin (1:200). The cells were rinsed 3 times with a blocking buffer solution, and incubated for 30 minutes with secondary antibodies conjugated with Alexa Fluor 568 or Alexa Fluor 488. The stained cover slip was washed three times with a blocking buffer solution, and mounted. The fluorescence images were recorded using an LSM510 META confocal laser scanning microscope (Zeiss).

Example 7: Measurement of Intracellular Hydrogen Peroxide

The intracellular $H_2O_2$ level was measured using 5,6-chloromethyl-2',7'-dichlorodihydrofluorescein diacetate (CM-DCFH-DA, Invitrogen), an oxidation-sensitive fluorescent dye. Human epidermal melanocyte, SK-MEL-5, SK-MEL-28, A375 and G361 cells ($3 \times 10^5$) were grown in a 35 mm culure dish and infected with retroviruses for 24 hours. After that, the cells were serum-starved for 18 hours, and stimulated with 20% FBS for 10 minutes in a phenol red-free medium. After stimulated as described above, the cells were quickly rinsed with a Krebs-Ringer solution, and incubated with 5 µM CM-DCFH-DA for 5 minutes. 2',7'-dichlorodihydrofluorescein (DCF) fluorescence was collected for 10 seconds using an inverted Axiovert 200 fluorescence microscope (Zeiss). The relative DCF fluorescence was calculated by averaging the fluorescence intensities of 60 to 80 cells after subtracting the background fluorescence from each image using an ImageQuant™ software (GE Healthcare). The desorbed sphenoid cells were excluded from quantification.

Example 8: Retrovirus Production

Retroviruses encoding human PrxII were produced using a bicitronic pLXIN vector and a Retro-X Q vector system (Clontech). First, human PrxII wild-type (WT) coding sequences were inserted to pLXIN by PCR cloning. Viruses were produced by stably trasfecting the resultant vector to a stable NIH3T3-based dualtropic packaging cell line RetroPack™ PT67. The viruses were mostly used for PrxII overexpression in the SK-MEL cells. The contentration of the viruses (viral titers) was determined ($1 \times 10^6$ virus particle/ml), and the viruses were divided and stored at −70° C.

For retrovirus infection, the divided viruses were thawed in a warm water bath, and mixed with 10 μg/ml polybrene.

Example 9: Proliferation and Migration Assay

The extent of cell proliferation was measured using a WST-1 cell proliferation assay kit (Roche Diagnostics, USA) according to the protocol of the manufacturer. The number of cells was expressed as an absorbance value at 450 nm averaged from 3 wells after subtracting the turbidity at 600 nm. The chemotactic transmigration assay was performed in a 24-well Transwell culture chamber (Costar; polycarbonate membrane insert with 8-μm pore size). The bottom of the insert was coated with gelatin B (1 mg/ml) and air-dried for 1 hour. Retroviruses or transfection complexes were treated to melanoma cells ($6 \times 10^3$). After 24 hours, the infected or transfected melanoma cells were serum-starved for 18 hours. A 20% FBS solution was added to bottom chambers including a basal medium containing 0.5% BSA. The upper chamber wells were each filled with a basal medium including 0.5% BSA. The Transwell chamber was incubated for 12 hours in a 37° C./5% $CO_2$ incubator. After the incubation, the non-migrating cells at the top of the filter were removed. The cells that migrated onto the bottom of filter were fixed and stained with 0.6% hematoxylin and 0.5% eosin. The stained cells were photographed and counted. The number of migrating cells was averaged from 3 wells.

Example 10: Wound Healing Assay

A wound was created on a cell monolayer by scratching with a pipet tip. The wound was washed with PBS to remove cell fragments, and a fresh medium was supplied thereto. For 12 hours after that, the cells were made to be proliferated and migrated to the wound. The migration of the cells to the wounded area was observed under a microscope. The width of the wound was measured using an Image J software.

Example 11: Metastasis of B16F10 Melanoma Cells to Lung in Mouse

After B16F10 cells were temporarily transfected with PrxII siRNA for 24 hours and trypsinized, the cells were resuspended in a Hank's balanced salt solution (HBSS). The cell suspension was injected by intravenous injection to a C57/BL6 mouse ($1 \times 10^6$ cells per mouse). The mouse was sacrified after 10 days, and the lung was removed after transcardia perfusion-fixation with a heparinized saline solution including 3.7% formaldehyde. The removed lung was paraffin embedded and sectioned using a rotary microtome (Leica RM2255). Two serial tissue sections (4 μm in thickness) were stained with haematoxylin and eosin. The melanoma tumor nodules metastasized from the surface of the lung and the HE-stained tissue sections were counted. In order to verify the effects of gliotoxin (GT), chaetocin and chetomin, the melanoma cells were intravenously injected to the C57/BL6 mouse, and then gliotoxin (300 mg/kg) was intraperitoneally injected for 5 times over 10 days.

Example 12: NADPH Oxidase Activity Assay

Whole cell superoxide production was measured using an enhanced luminescence system (Diogenes, National Diagnostics). For the assay, the serum-starved cells were pre-incubated with a 100 μl Diogene reagent at 37° C. for 5 minutes. After being stimulated by the indicated growth factor, chemiluminescence was detected every second for 10 minutes with a TD-20/20 Luminometer (Turner Biosystems).

Example 13: Balloon-injury Model of Rat Carotid Artery

Animal experiments were performed in compliance with the guidelines of Institutional Animal Care and Use Committee (IACUC) of the Ewha Womans University. Balloon injury was created using an infiltrated 2 F Fogarty balloon catheter in the left common carotid artery as follows: after the ten-week-old male Sprague-Dawley rats were anaesthetized by isoflurane gas ($N_2O:O_2/70\%:30\%$) inhalation, the left external carotid artery was exposed, and its branches were electrocoagulated. A catheter was pushed 1 cm in through the transverse arteriotomy of the external carotid artery, and the endothelial denudation was achieved by three passes along the common carotid artery. After the catheter was removed, the punched area was sealed and the clapped common carotid artery was opened for resuming the blood flow. Unless otherwise stated, the rats were recovered in a cage for 10 days, and subjected to histological and immunological analyses.

Example 14: Histological Analysis

Rats were anesthetized, and the common carotid artery was excised after transcardiac perfusion-fixation with a heparinized saline solution containing 3.7% formaldehyde. The vessels were paraffin embedded and sectioned using a rotary microtome (Leica RM2255). Two serial tissue sections (4 μm in thickness) were obtained from the middle area of common carotid arteries, and stained with haematoxylin and eosin (HE). The luminal, internal elastic laminal, and external elastic laminal areas were measured using NIH Image v1.62. The intimal and medial areas were determined by subtracting the luminal area from the internal elastic area and subtracting the internal elastic area from the external elastic area. The values from the two serial sections for each rat were averaged for analysis.

Example 15: Local Delivery of siRNA or ETP Compound or Derivative in Carotid Artery For the in vivo injection of siRNA, a siRNA mixture specific to rat PrxII (200 nM) was premixed with a siPORT™ NeoFX™ reagent according to the instructions of the manufacturer (Ambion). Immediately after the balloon injury, the siRNA-injected mixture (200 μL) was injected through a catheter after briefly washed with Opti-MEM. After the incubation for 15 minutes, the blood flow was resumed. A siGLO-Red (Dharmacon), which is fluorescent dye-conjugated control siRNA, was used for optimizing in vivo injection efficiency. Similarly, the ETP compound (200 nM in DMSO) was injected through a catheter and incubated for 30 minutes.

Example 16: Immunohistochemistry and Immunofluorescence Staining

Immunohistochemistry for the overoxidized 2-Cys Prxs was performed on the paraffin sections using an anti-Prx-$SO_{2/3}$ antibody (1:1000 dilution). Briefly, the sections were de-waxed in xylene and rehydrated in ethanol, and subsequently the antigen retrieval was performed by boiling in a citric buffer solution (pH 6.0). After that, the sections were incubated with a primary antibody for 48 hours at 4° C. After washing three times with a phosphatebuffered saline solution, the sections were incubated with a peroxidase-conjugated secondary antibody and stained with a 3',3'-diaminobenzidine (DAB) substrate solution. For negative staining, the Prx-50$_{2/3}$ antibody was blocked with the corresponding antigenic peptide (DFTFVC(SO$_{2/3}$)PTEI). For indirect immunofluorescence staining, the paraffin sections were blocked with 5% normal rabbit serum (Vector Laboratories) in PBST (a PBS solution of 0.3% Triton X-100) for 1 hour at room temperature. The sections were then incubated overnight at 4° C. with the antigens against rat smooth muscle α-actin (1:300 dilution) and rat CD31 (PECAM-1, 1:200 dilution). The nuclei were labeled with DAPI. After several PBST washes, the samples were incubated for 2 hours at room temperature with Alexa Fluor 568-conjugated donkey anti-mouse and Alexa Fluor 488-conjugated donkey anti-rabbit IgG antibodies. The fluorescence images were recorded on three random fields per tissue section at a screen magnification of 100× using a LSM 510 Meta confocal microscope equipped with argon and helium-neon lasers.

Example 17: TUNEL Assay

The paraffin sections were incubated for 10 minutes in PBS containing 0.1% Triton X-100. After that, TUNEL reactions were performed for 60 minutes at 37° C. using an In Situ Cell Death Detection Kit and Fluorescein (Roche Diagnostics Corp.) according to the instructions of the manufacturer. The cell nuclei were counterstained with DAPI.

Example 18: Vascular Permeability Test

Mice were injected intravenously with 100 μl of 5% Evans blue for 30 minutes and then perfused with PBS for 5 minutes. The common carotid arteries were removed from both uninjured collateral and injured ipsilateral ones. The result was dissected, opened longitudinally, and examined on a phase contrast microscope with a magnification of 20×. For quantification, the Evans blue inflowed into the blood vessel was extracted by being placed in formamide at 55° C. overnight and centrifuged for 10 minutes at 12,000 rpm. The supernatants were collected and the absorbance was measured at 620 nm. The background value of the Evans blue dye was measured at 740 nm and substracted from the values in carotid arteries. For VEGFR2 inhibition, SU5416 (20 mg/kg) was injected intraperitoneally for 3 times (Days −1, 1, and 3) before and after the balloon injury. Control injection was made of 200 μl PBS including a vehicle (5% DMSO).

Example 19: Scanning Electron Microscopy (SEM)

The carotid vessels were taken from animals, opened longitudinally, and fixed with 2.5% glutaraldehyde for 24 hours. The tissues were rinsed with PBS, incubated with 1% osmium tetroxide, and then dehydrated through a series of ethanol dilutions. The tissues were dried to the critical point and mounted on scanning electron microscopy stubs with colloidal silver paste. After sputter-coated with gold/palladium, the specimens were examined with a scanning electron microscope (Hitachi, Japan).

Experimental Example 1: Catalytic Activity for Hydrogen Peroxide Reduction

The chemical feature of the epidithiodioxopiperazine compound of the present invention or its derivatives is the intramolecular disulfide bridge present in the epidithiodioxopiperazine ring moiety. Cellular peroxidase reduces hydrogen peroxide utilizing the electrons derived from NADPH via two electron-transfer routes, that is, Trx/TR or GSH/GR, therefore, spectrophotometric assay was performed for the hydrogen peroxide-reducing activity in the presence of each system, and the results are shown in FIGS. 1 to 5.

Figure 1:
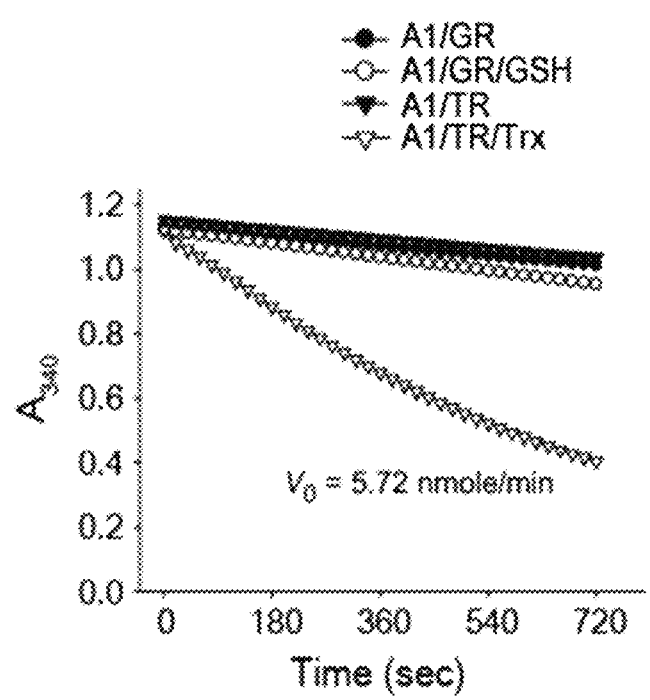
FIG. 1 is a diagram showing catalytic activities of Compound A1 according to the present invention for hydrogen peroxide reduction. Vo in the graphs of FIGS. 1-4 indicates reduction reaction rate, which is represented by an amount of reduced hydrogen peroxides per minute (nmole/min).
Figure 2:
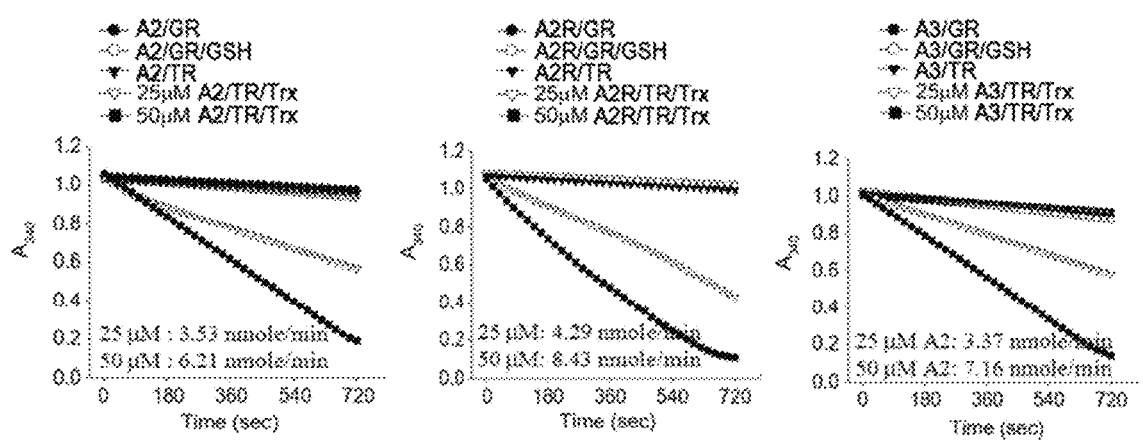
FIG. 2 is a diagram showing a catalytic activity of Compound A2, Compound A2R having a dithiol group by reducing the intramolecular disulfide bridged bond of A2 as a comparative example, and Compound A3 according to the present invention for hydrogen peroxide reduction.
Figure 3:
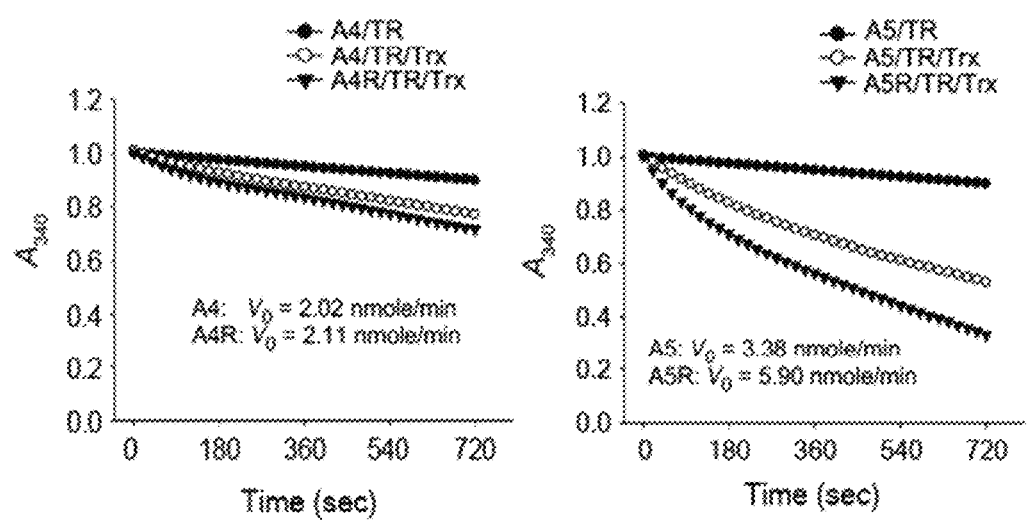
FIG. 3 is a diagram showing a catalytic activity of Compound A4, Compound A4R having a dithiol group by reducing the intramolecular disulfide bridged bond of A4 as a comparative example, Compound A5, Compound A5R having a dithiol group by reducing the intramolecular disulfide bridged bond of A5 according to the present invention for hydrogen peroxide reduction.
Figure 4:
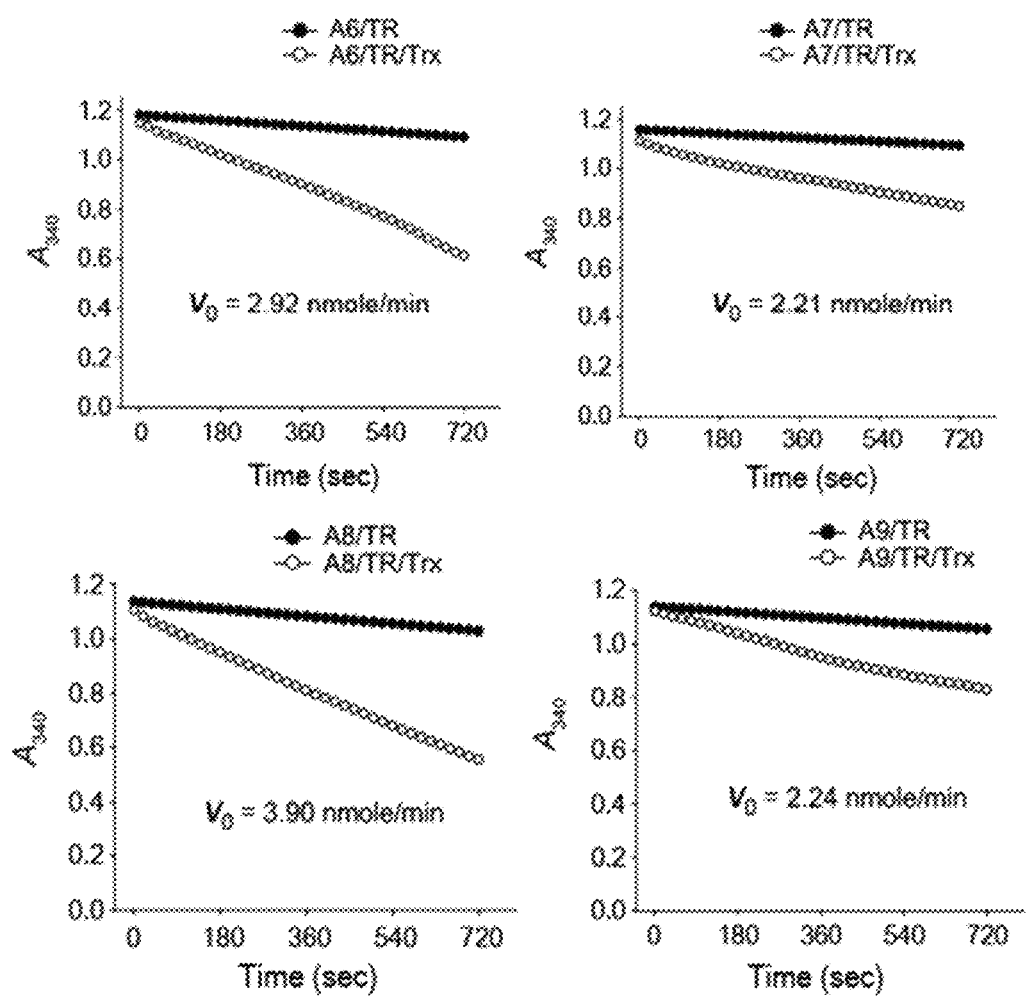
FIG. 4 is a diagram showing catalytic activities of Compounds A6, A7, A8 and A9 according to the present invention for hydrogen peroxide reduction.
Figure 5:
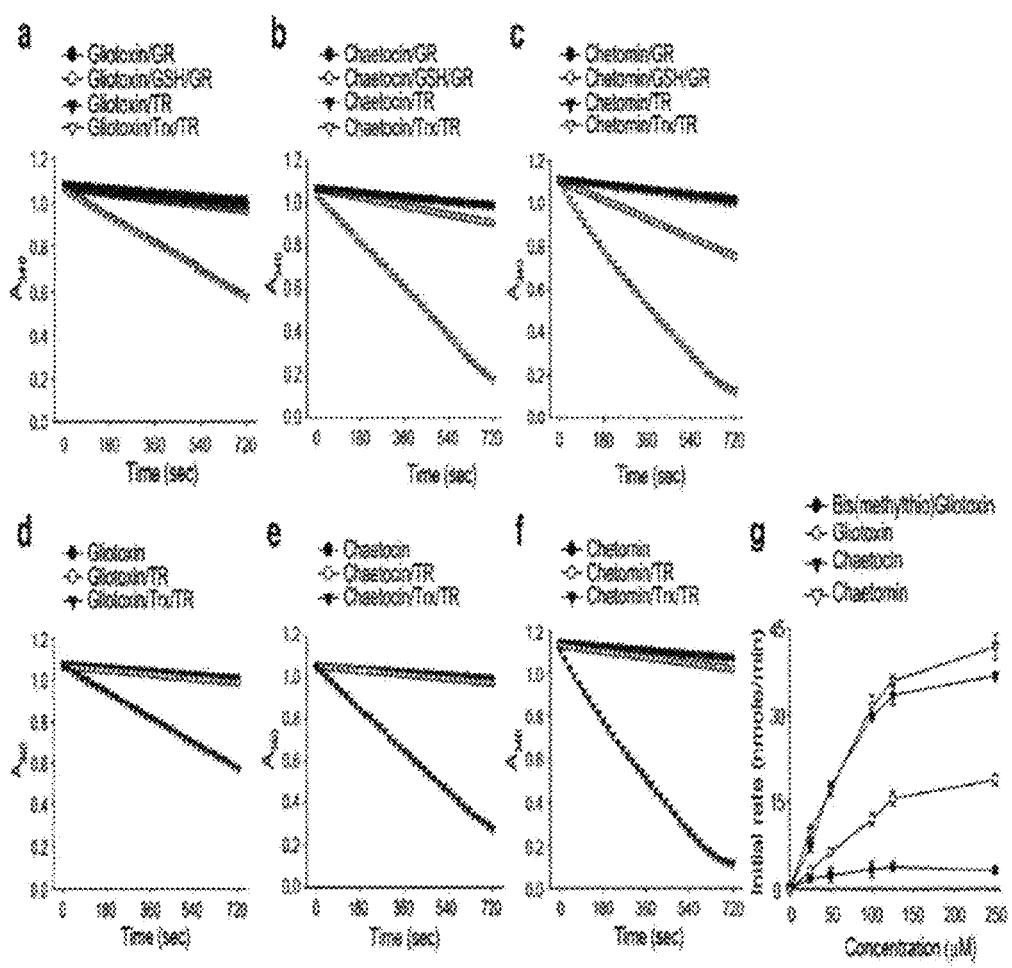
FIG. 5 is a diagram showing catalytic activities of ETP compounds for hydrogen peroxide reduction. (a) to (c) show the hydrogen peroxide reducing power of gliotoxin, chaetocin and chetomin, respectively. An in vitro peroxidase reaction is carried out by adding a 25 µM ETP compound each under the coupling oxidation-reduction system specified in the graph. (d) to (f) are diagrams showing typical Trx-dependent peroxidase activities of ETP compounds. The reaction is carried out while adding the factors of the Trx/TR coupling system specified in the graph. The representative reaction curves from three experiments are shown. (g) is a diagram showing concentration-dependent peroxidase activities of ETP compounds. The initial rate is presented as mean±standard error from 3 independent experiments. Bis (methylthio)gliotoxin in which the disulfide bridged bond is reduced and methylated is used as a negative control group.
Figure 6:
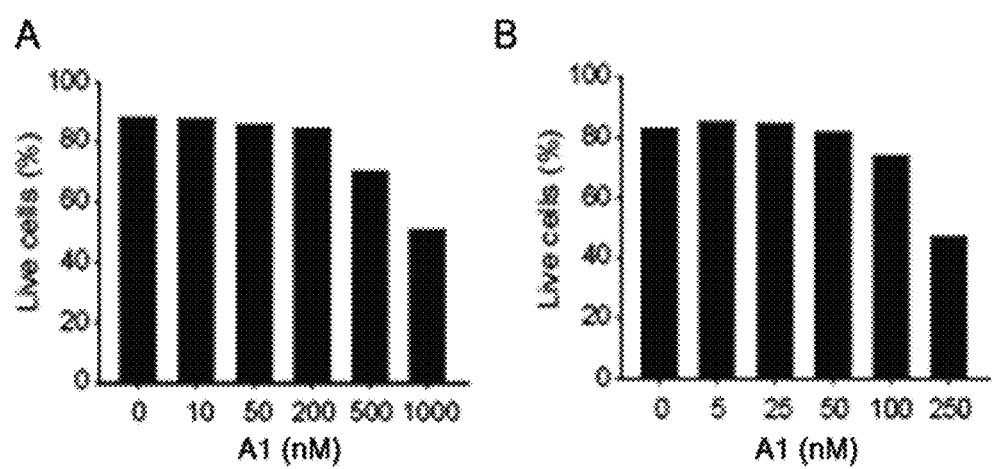
FIG. 6 is a diagram showing experimental results of cytotoxicity for (A) human aortic smooth muscle cells (HASMC) and (B) human aortic endothelial cells (HAEC) of Compound A1 according to the present invention as the percentage of live cells.
Figure 7:
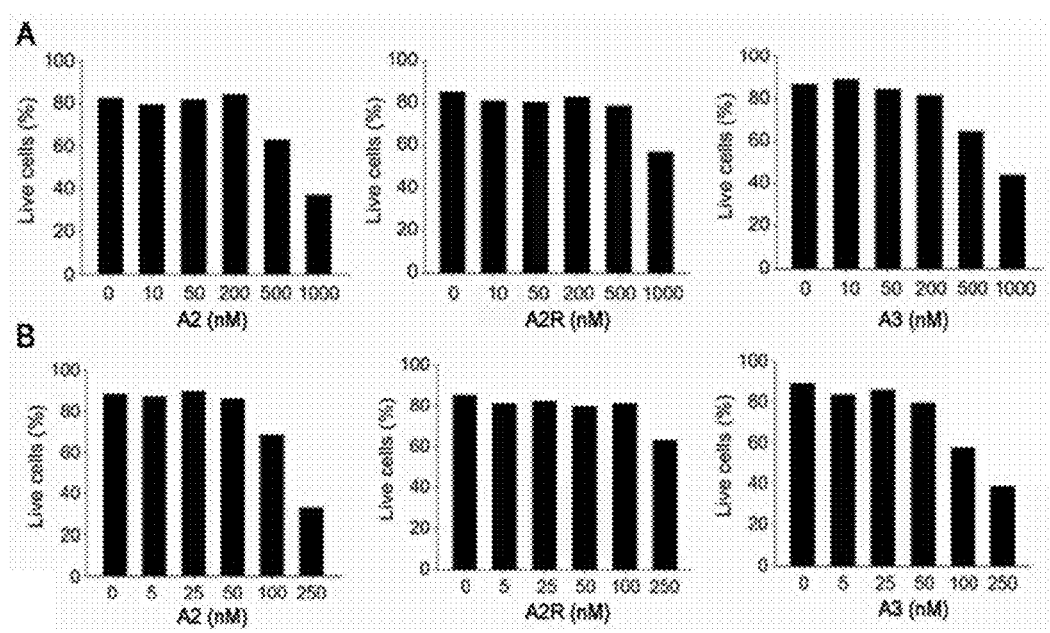
FIG. 7 is a diagram showing experimental results of cytotoxicity for (A) human aortic smooth muscle cells (HASMC) and (B) human aortic endothelial cells (HAEC) of Compound A2, Compound A2R as a comparative example, and Compound A3 according to the present invention as the percentage of live cells.
Figure 8:
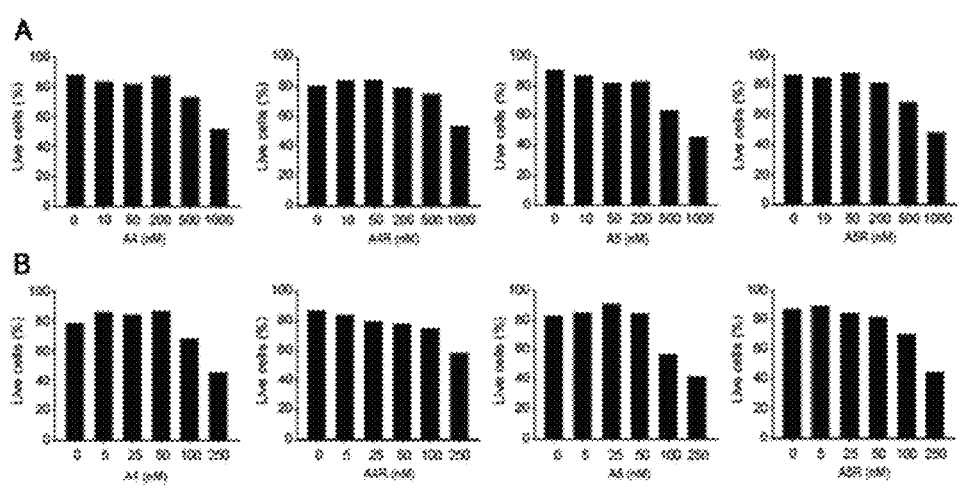
FIG. 8 is a diagram showing experimental results of cytotoxicity for (A) human aortic smooth muscle cells (HASMC) and (B) human aortic endothelial cells (HAEC) of compound A4, Compound A4R as a comparative example, Compound A5 and its comparative example A5R according to the present invention as the percentage of live cells.
Figure 9:
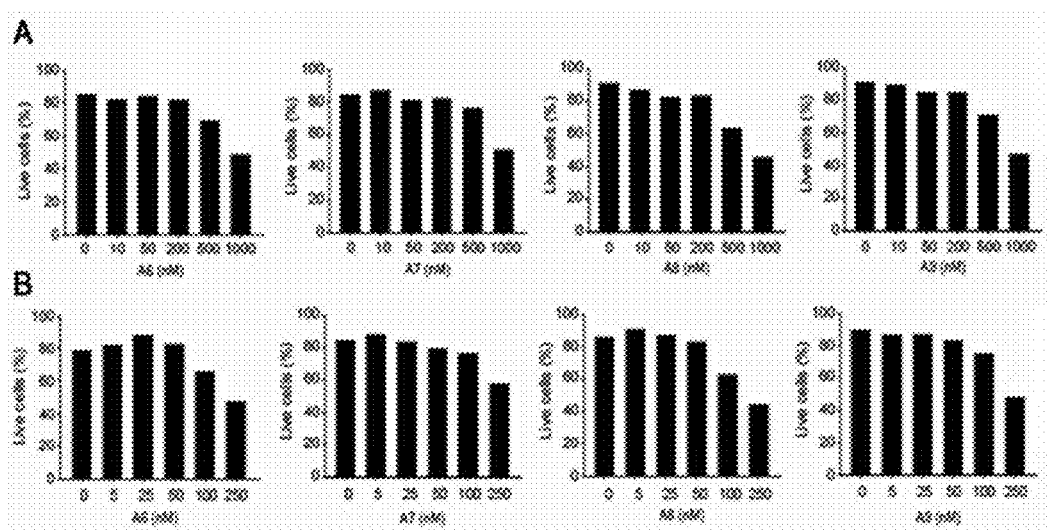
FIG. 9 is a diagram showing experimental results of cytotoxicity for (A) human aortic smooth muscle cells (HASMC) and (B) human aortic endothelial cells (HAEC) of Compounds A6 to A9 according to the present invention as the percentage of live cells.
Figure 10:
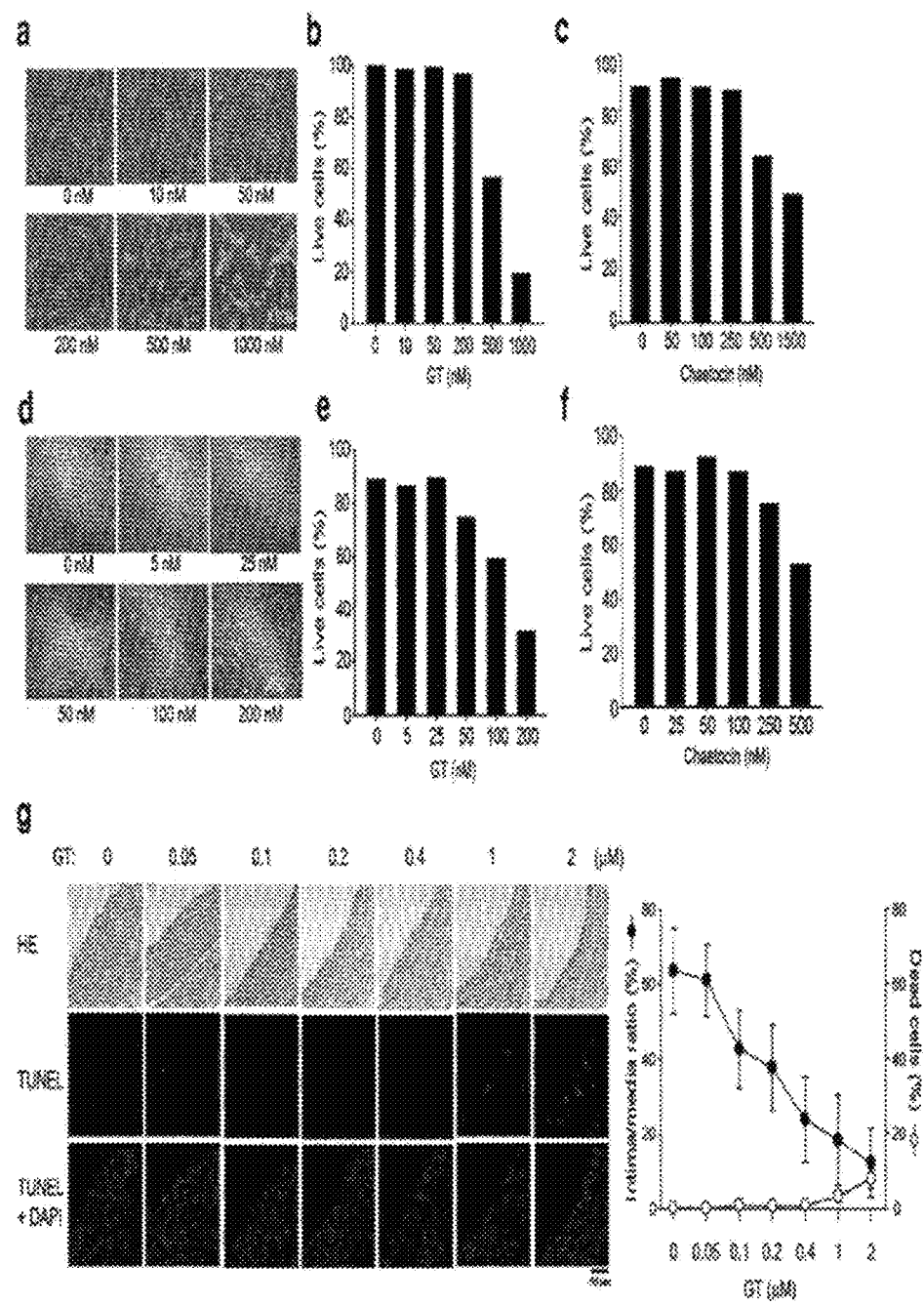
FIG. 10 is a diagram showing experimental results of in vitro and in vivo cytotoxicity of GT and chaetocin. (a) and (d) are photomicrographs of human aortic smooth muscle cells (HASMCs) and human aortic epithelial cells (HAECs) treated with GT at the concentrations indicated in the graphs. (b) and (c) are diagrams showing the concentration-dependent viability of HASMCs when treated with GT or chaetocin, respectively, and (e) and (f) are diagrams showing the viability of HAECs when treated with GT or chaetocin, respectively. Herein, after each ETP compound is pretreated with the serum-starved cells in a basal medium containing 0.5% FBS for 2 hours at the indicated concentrations, the cells are collected and stained by trypan blue for checking viability. The viability is presented as the percentage of unstained live cells with respect to the total number of cells. (g) is a diagram showing the in vivo cytotoxicity of GT in rat carotid arteries. GT is injected into the lumen of balloon-injured carotid arterial vessels at the indicated concentrations and incubated for 30 minutes. DMSO is used as a control group. Representative HE-stained images are shown, and the ratio of intima versus media measured from HE-stained carotid artery samples is presented as mean±standard error (n=7 per group). The cell death is assessed by TUNEL staining of paraffin sections of balloon-injured carotid arterial vessels (left), calculated as the percentage of TUNEL-positive cells per DAPI-positive cells (right).

As a result, as shown in FIGS. 1 to 5, A1 to A9, gliotoxin, chaetocin and chetomin, which shared the epidithiodioxopiperazine structure, all exhibited excellent hydrogen peroxide-reducing activities in the presence of a Trx/TR system. Particularly interestingly, the activities of chaetocin and chetomin in the presence of a Trx/TR system were 8.18±0.24 and 8.62±0.51 nmol/min, respectively, thereby was approximately two-fold higher than the activity of GT (3.72±0.53 nmol/min) (FIG. 5). Although chaetocin and chetomin exhibited the activities of 1.51±0.39 and 2.53±0.79 nmol/min, respectively, in the presence of a GSH/GR system, the extent was marginal compared to the activities in the presence of the Trx/TR system. Accordingly, as shown in FIGS. 5d to 5f, the hydrogen peroxide-reducing activities of the ETP compounds required all three components of a Trx/TR/NADPH system, and the activities were proportional to the concentration. In addition, bis(methylthio)gliotoxin with methylated thiol groups was used as a control group. As a result, the peroxidase activity was not observed for bis(methylthio)gliotoxin with methylated thiol groups (FIG. 5g). In addition, it was seen that bis(methylthio)gliotoxin with methylated thiol groups had no peroxidase activities since disulfide bridge can not be formed by an oxidation-reduction reaction in bis(methylthio)glyotoxin. This indicated that the oxidation-reduction cycle of dithiols in the ring within the compound is essential for the peroxidase activity. Furthermore, the result demonstrated that the 2-Cys-Prx-analogous peroxidase activity of the epidithiodioxopiperazine compound or its derivatives according to the present invention was Trx/TR system-dependent.

In addition, the results were compared using the reduced types (A2R, A4R and A5R) of A2, A4 and A5 (FIGS. 3 and 4). These reduced compounds exhibited similar hydrogen peroxide-reducing activities to the corresponding oxidized types (A2, A4 and A5, respectively). Furthermore, the comparative group includes compounds including two thiol groups by reducing the intramolecular disulfide bridged bond, and these compounds may be directly used for hydrogen peroxide reduction without a conversion process to reduced types by a Trx/TR system since these compounds have similar forms with the active types of intracellular 2-Cys-Prx, and therefore, it was demonstrated that the reduced types had higher intial reaction rates for hydrogen peroxide reduction compared to the corresponding oxidized types.

Meanwhile, A2R, A4R and A5R did not actually show PDGF- and VEGF-dependent cell proliferation and migration regulatory activities as shown in the experiments to be described later, and this may be inferred that these compounds had no PDGF- and VEGF-dependent cell proliferation and migration regulatory activities since the reduced form of the derivatives which have the dithiol in the piperazine ring cannot be introduced into the cells. This indicated that the oxidation-reduction cycle between the intramolecular disulfide bridged bond and the dithiol in the piperazine ring within the ETP derivative was essential for the peroxidase activity. In addition, from the results described above, it was demonstrated that the 2-Cys-Prx-analogous peroxidase activity of the epidithiodioxopiperazine compound or its derivatives according to the present invention was Trx/TR system-dependent.

Experimental Example 2: In Vitro and In Vivo Cytotoxicity Experiment

Most ETP compounds have been known to be cytotoxic to animal cells. Accordingly, the inventors of the present invention determined a safe concentration range of the epidithiodioxopiperazine compound or its derivatives in vascular cells. For this, human aortic smooth muscle cells (HASMCs) and human aortic endothelial cells (HAECs) were pretreated for 2 hours with various concentrations of gliotoxin or chaetocin, and A1 to A9 that are ETP derivatives according to the present invention, and cultured in a fresh medium for 24 hours followed by cell viability assay (FIGS. 6 to 10).

As a result, the viability of HASMCs and HAECs with respect to gliotoxin and A1 to A9 under a serum-deficient condition were guaranteed at concentrations of 200 nM and 50 nM or less, respectively. Chaetocin was found to be relatively less toxic. The low viability of the two cells at high concentrations was considered to be due to various side effects including NF-κB inhibition. Accordingly, for the experiments described below, the inventors of the present invention used the ETP compounds at a concentration range of 100 nM and 50 nM, a safe dosage for in vitro experiments for HASMCs and HAECs, and for compounds having low tendency, the concentration was increased up to a range of 200 nM and 100 nM.

Figure 11:
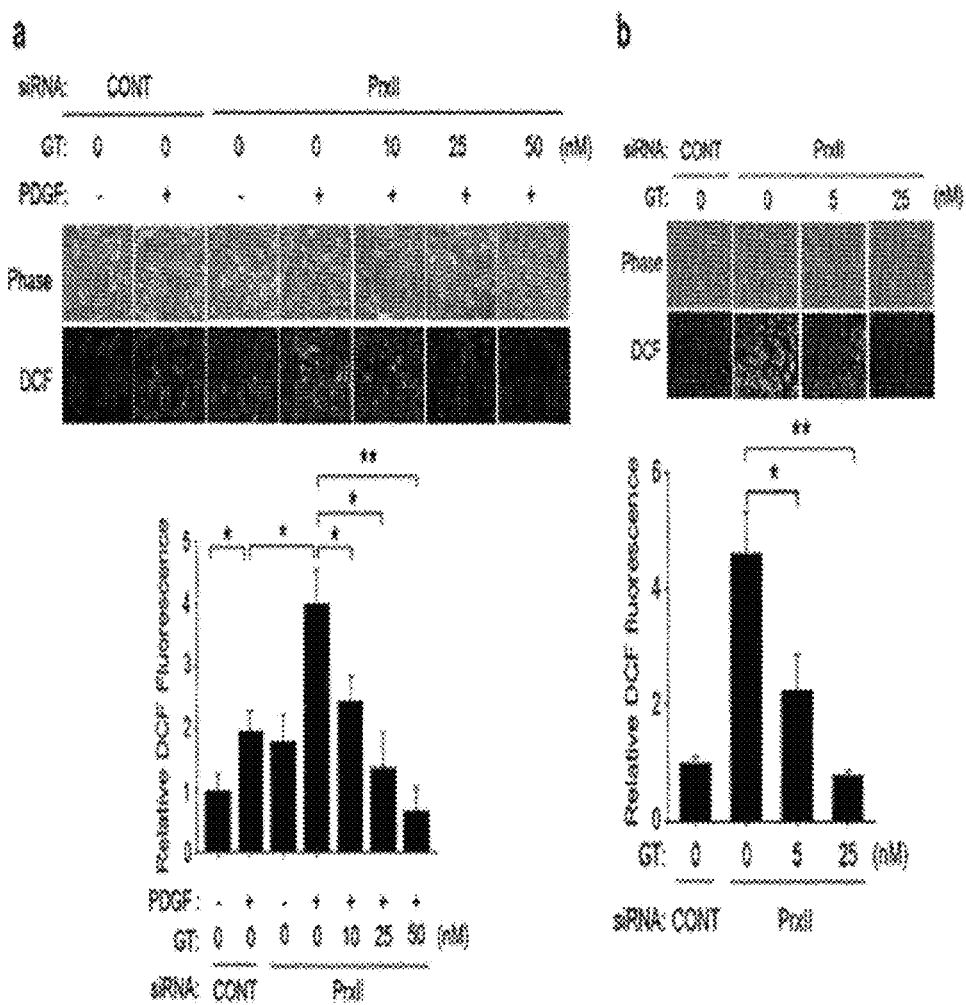
FIG. 11 shows the reciprocal regulatory ability of PDGF- and VEGF-dependent hydrogen peroxide by gliotoxin in HASMCs and HAECs injected with PrxII siRNA and pretreated for 2 hours with DMSO (control group) or GT. (a) and (b) each show the level of intracellular hydrogen peroxide in HASMCs and HAECs as DCF fluorescence images and relative intensities. The graph shows the relative DCF fluorescence intensity averaging the fluorescence from 50 to 80 cells as mean±standard error (n=3, *p<0.01, **p<0.001).

Experimental Example 3: Effects of PrxII Function Replacement by Gliotoxin and Epidithiodiketopiperazine Derivative in Growth Factor-Induced Signaling and Cell Proliferation/Migration (1) Effects of PrxII Function Replacement by Gliotoxin First, the ability of GT to eliminate intracellular hydrogen peroxide in PrxII knocked down HASMCs and HAECs was tested. The cellular hydrogen peroxide production was monitored using an oxidant-sensitive fluorescence dye (2', 7'-dihydro-chlorofluorescein diacetate, $H_2DCF$-DA). The level of intracellular hydrogen peroxide increased by approximately two fold by PDGF treatment in serum-deficient control HASMCs, and then markedly increased by combining with the PrxII knockdown (FIG. 11a). However, the GT treatment completely canceled out the increased level of intracellular hydrogen peroxide in a concentration-dependent manner (FIG. 11a). In addition, the basal level of intracellular hydrogen peroxide in HAECs, which was markedly enhanced by the PrxII knockdown, was also completely eliminated by the GT treatment (FIG. 11b).

Figure 12:
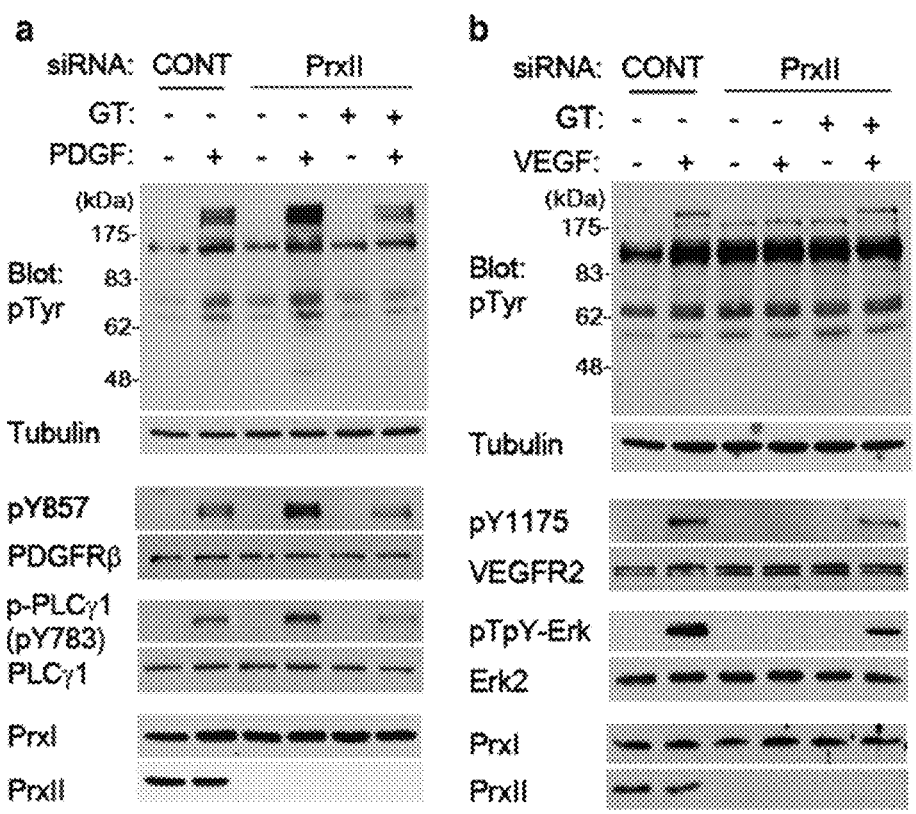
FIG. 12 (a) is a diagram showing the effects of GT on PDGF-induced tyrosine phosphorylation in PrxII knocked down HASMCs as immunoblot analysis, and FIG. 12 (b) is a diagram showing the effects of GT on VEGF-induced tyrosine phosphorylation in PrxII knocked down HAECs as immunoblot analysis. Representative blots of total tyrosine phosphorylation (pTyr) are shown from 3 repeated experiments by an anti-phosphotyrosine antibody (4G10). In addition, activation of PDGFR-β and PLCγ1 in HASMCs, and activation of VEGFR and Erk in HAECs are shown as representative blots.
Figure 13:
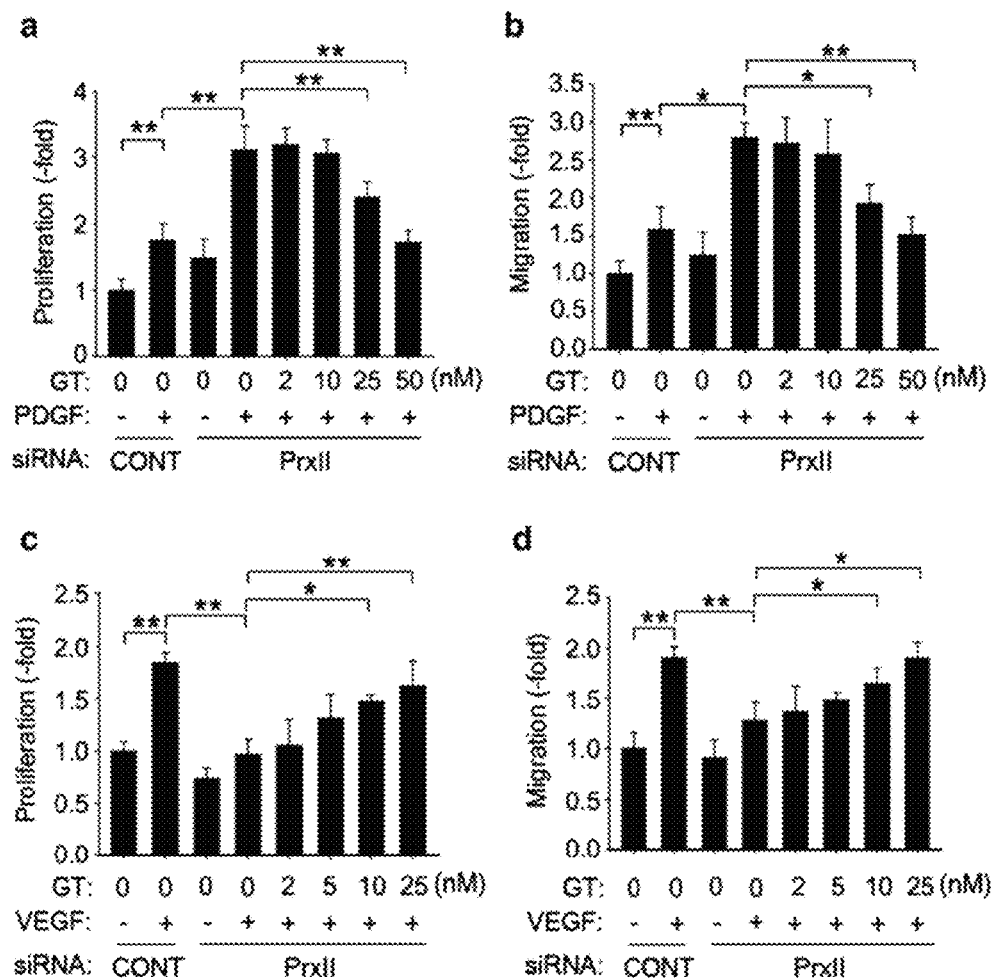
FIG. 13 is a diagram showing the effects of GT on the growth factor-induced proliferation and migration of PrxII knocked down vascular cells. (a) and (b) are diagrams showing the effects of GT on the proliferation and the migration of HASMCs, respectively, in response to PDGF, and (c) and (d) are diagrams showing the effects of GT on the proliferation and the migration of HAECs, respectively, in response to VEGF. The fold-increase of each cell is presented as mean±standard error (n=3, *p<0.05, **p<0.001).
Figure 14:
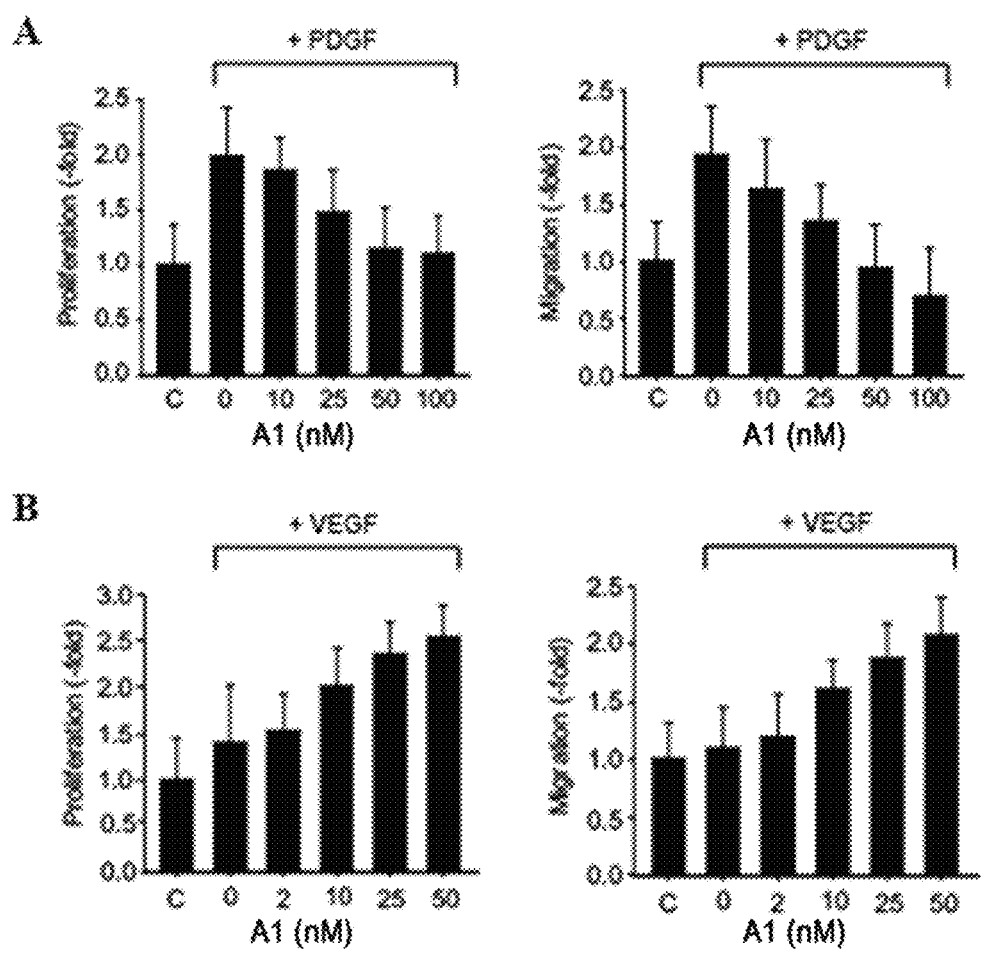
FIG. 14 is a diagram showing the effects of Compound A1 according to the present invention on the growth factor-induced proliferation and migration of PrxII knocked down vascular cells. A represents the effects on the proliferation and the migration of HASMC in response to PDGF, and B represents the effects on the proliferation and the migration of HAEC in response to VEGF.
Figure 15:
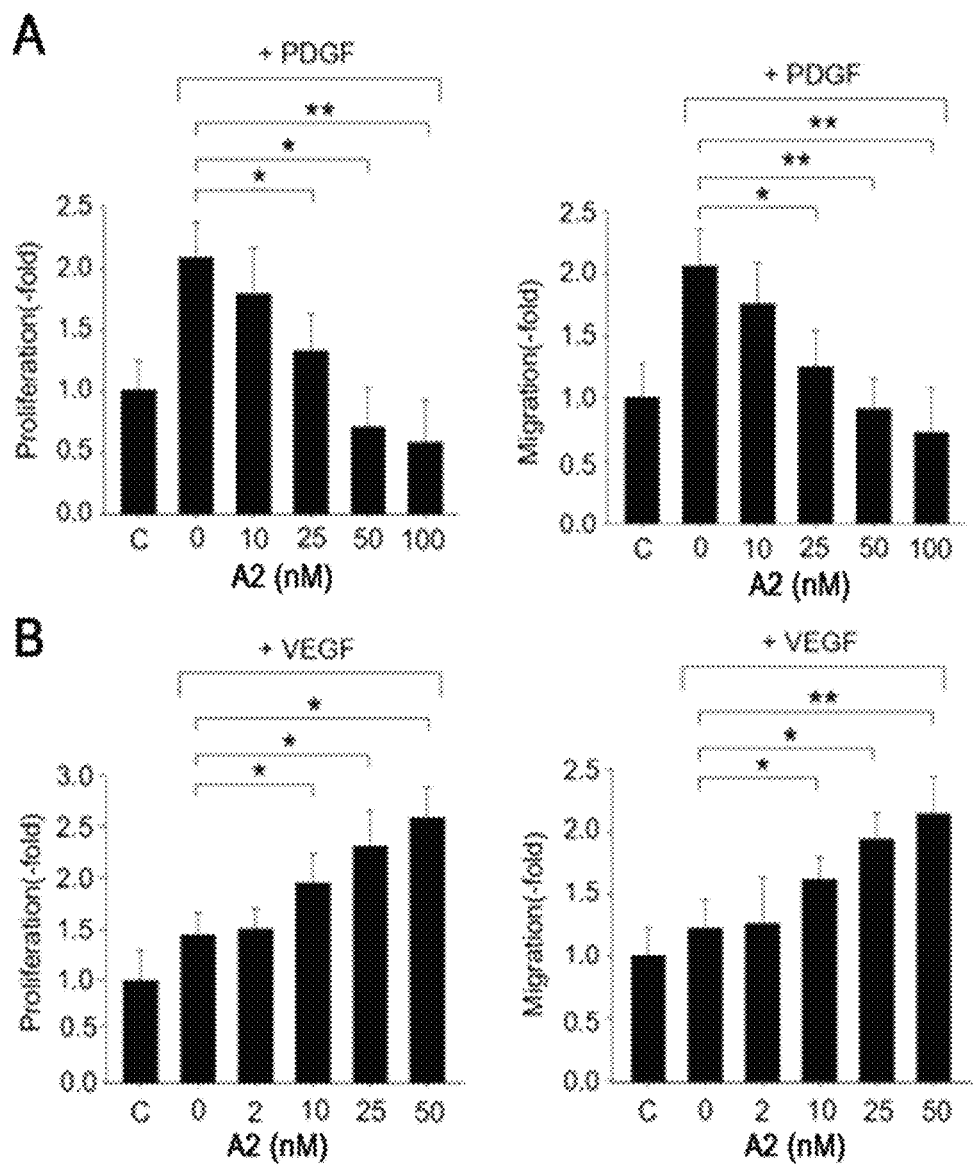
FIG. 15 is a diagram showing the effects of Compound A2 according to the present invention on the growth factor-induced proliferation and migration of PrxII knocked down vascular cells. A represents the effects on the proliferation and the migration of HASMC in response to PDGF, and B represents the effects on the proliferation and the migration of HAEC in response to VEGF.

In addition, the regulatory effects of GT on the PDGFRβ- and VEGFR2-mediated signaling pathway were examined. The GT treatment in HASMCs was quite different from PDGF-induced tyrosine phosphorylation that was enhanced by the PrxII knockdown (FIG. 12a). Particularly, the level of PDGFRβ and PLCγ1 activation was diminished to the level of stimulated control group cells. Conversely, the GT treatment in HAECs restored the VEGF-dependent activation of VEGFR2 and ERK that had been diminished by the PrxII knockdown (FIG. 12b). The effects of GT in vascular cell fuction were further validated. The GT treatment with increasing concentrations gradually reduced the proliferation and the chemotactic transmigration of HASMCs in response to PDGF, which had been enhanced by the PrxII knockdown (FIGS. 13a and 13b). Conversely, the same treatment for HAECs resulted in the enhancement of VEGF-induced proliferation and chemotactic transmigration that had been impaired by the PrxII knockdown (FIGS. 13c and 13d).

(2) Effects of PrxII Function Replacement by A1 to A9

The regulatory effects of the ETP derivatives A1 to A9 on the PDGFRβ- and VEGFR2-mediated signaling pathway were examined. The effects of ETP derivatives on the function of vascular cells, that is, human aortic smooth muscle cells (HASMCs) and human aortic endothelial cells (HAECs) were demonstrated. As described above, each EPT derivative was used in a concentration range of 100 nM and 50 nM or less, a concentration range exhibiting no cytotoxicity for HASMCs and HAECs, respectively, and for several compounds (A4, A7 and A9) having insignificant activities, the concentration was increased up to a maximum of 200 nM and 100 nM.

As a result, the ETP derivative treatments with increasing concentrations gradually reduced the proliferation and the chemotactic transmigration of HASMCs in response to PDGF, which had been enhanced by the PrxII knockdown (FIGS. 14A to 21A). Conversely, the same treatment for HAECs resulted in the enhancement of VEGF-induced proliferation and chemotactic transmigration that had been impaired by the PrxII knockdown (FIGS. 14B to 21B).

Figure 16:
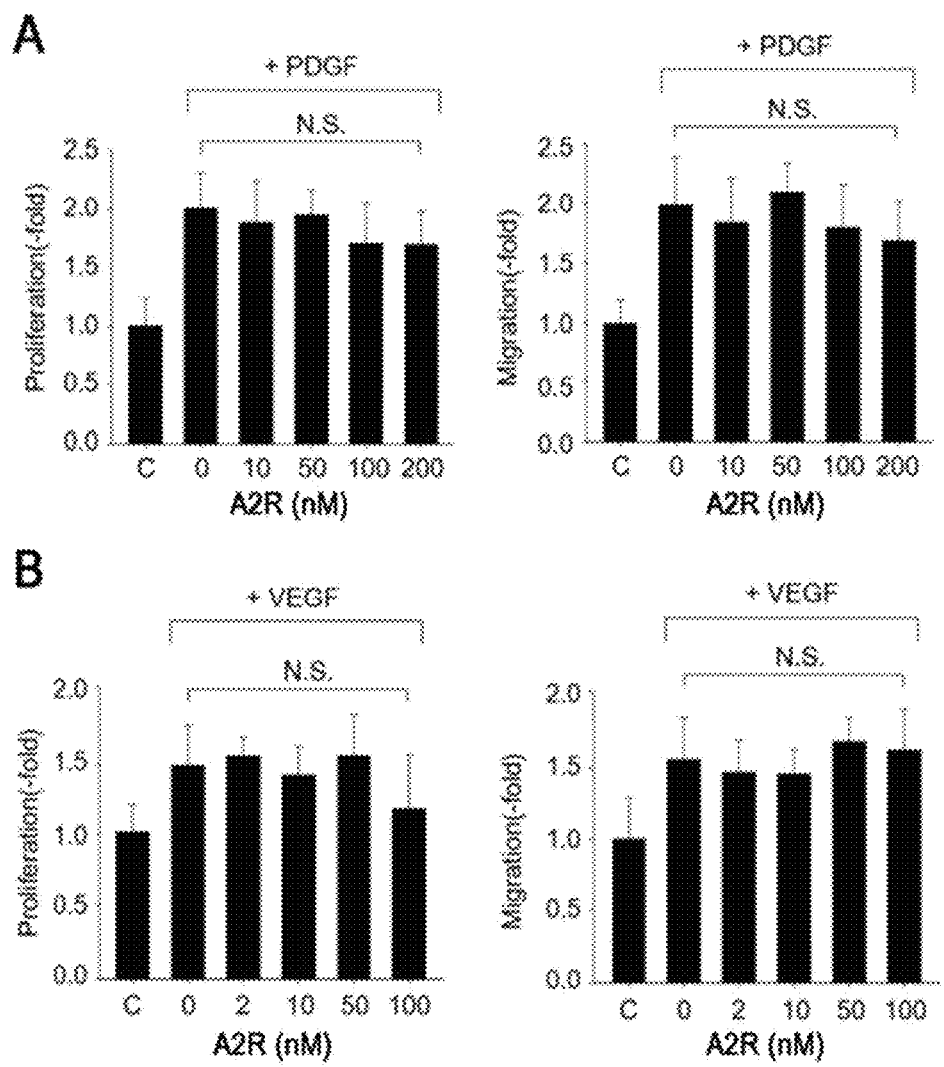
FIG. 16 is a diagram showing the effects of Compound A2R, a comparative example of Compound A2 according to the present invention, on the growth factor-induced proliferation and migration of PrxII knock-down vascular cells. A represents the effects on the proliferation and the migration of HASMC in response to PDGF, and B represents the effects on the proliferation and the migration of HAEC in response to VEGF. These results show the reduced form of the derivatives of the present invention in which disulfide bridged bond has been reduced cannot be introduced into a cell.
Figure 17:
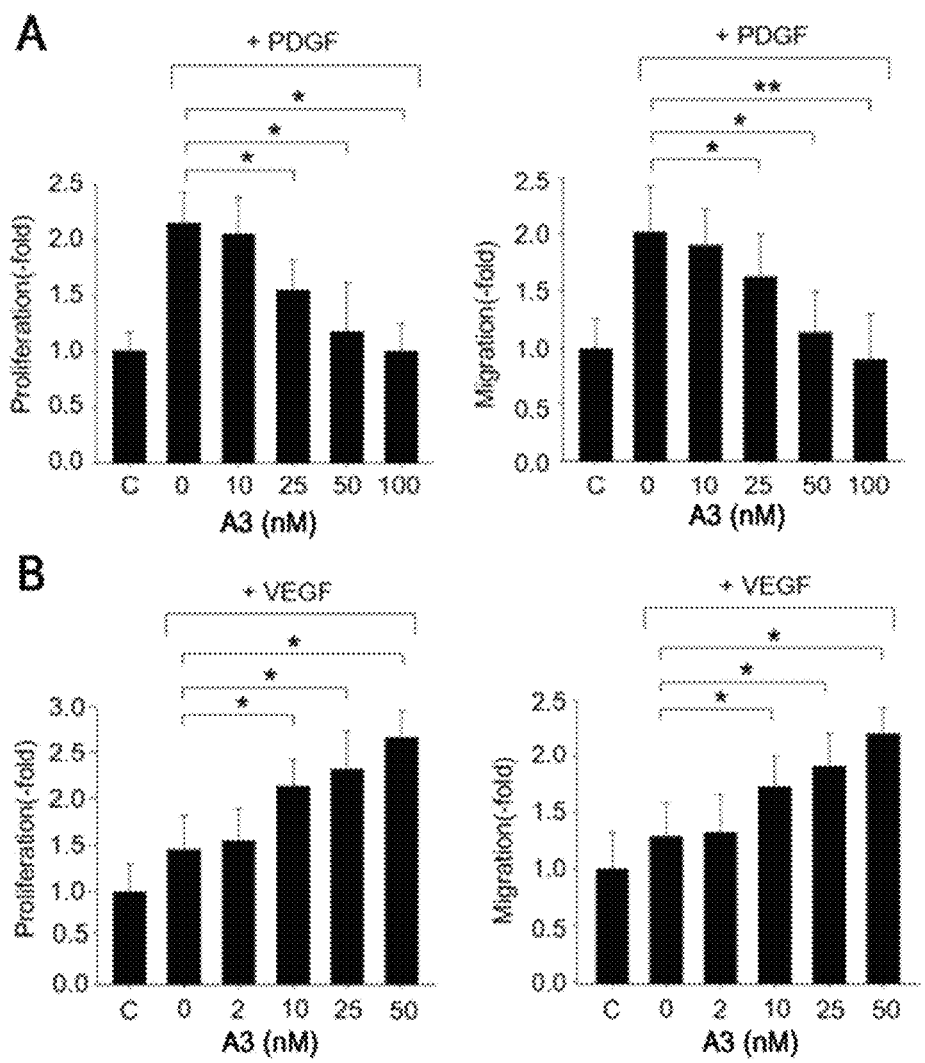
FIG. 17 is a diagram showing the effects of Compound A3 according to the present invention on the growth factor-induced proliferation and migration of PrxII knocked down vascular cells. A represents the effects on the proliferation and the migration of HASMC in response to PDGF, and B represents the effects on the proliferation and the migration of HAEC in response to VEGF.
Figure 18:
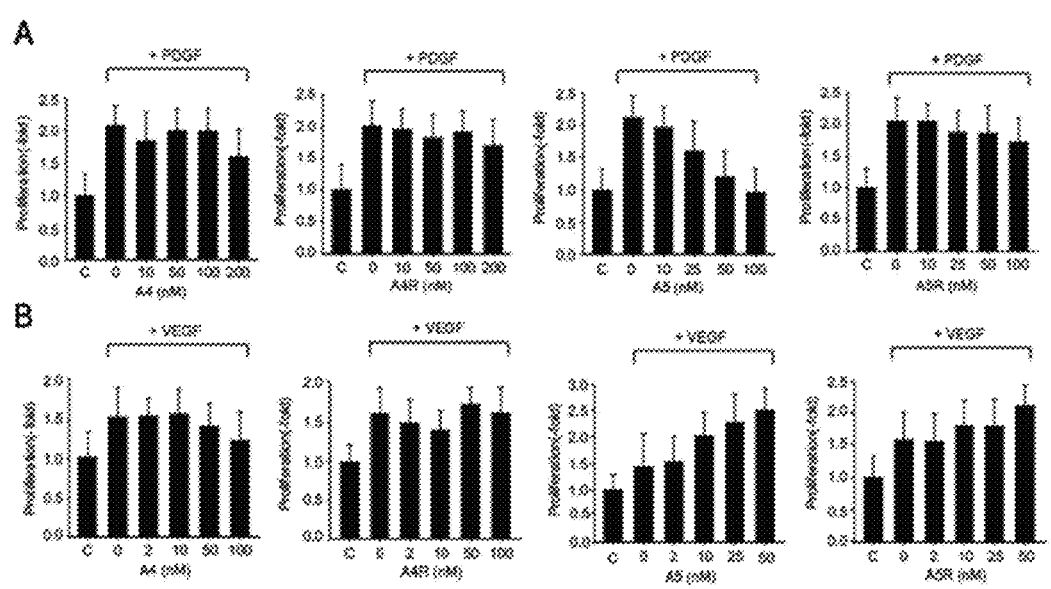
FIG. 18 is a diagram showing the effects of Compounds A4 and A5 according to the present invention and Compounds A4R and A5R that are comparative examples thereof on the growth factor-induced proliferation of PrxII knocked down vascular cells. A represents the effects on the proliferation of HASMC in response to PDGF, and B represents the effects on the proliferation of HAEC in response to VEGF.
Figure 19:
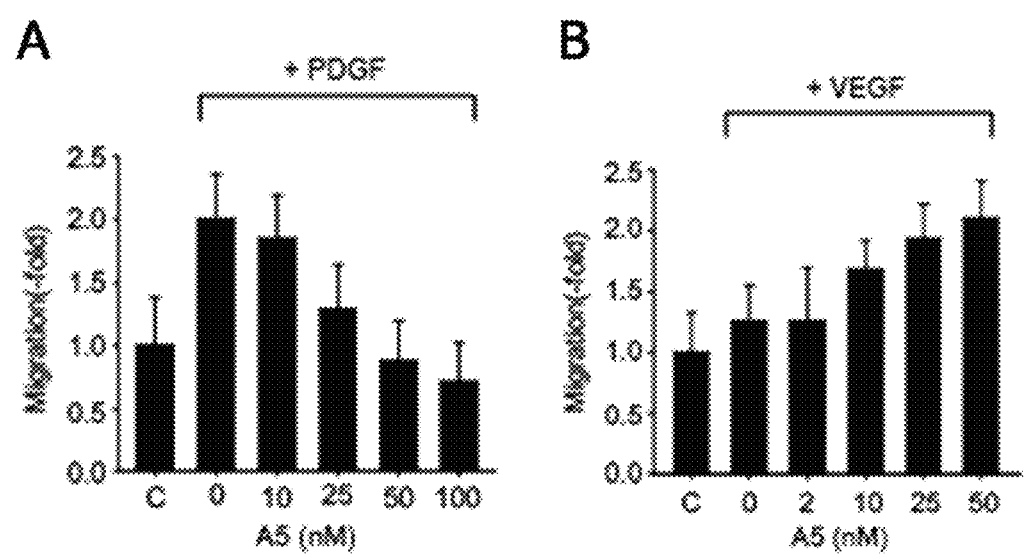
FIG. 19 is a diagram showing the effects of Compound A5 according to the present invention on the growth factor-induced migration of PrxII knocked down vascular cells. A represents the effects on the migration of HASMC in response to PDGF, and B represents the effects on the migration of HAEC in response to VEGF.
Figure 20:
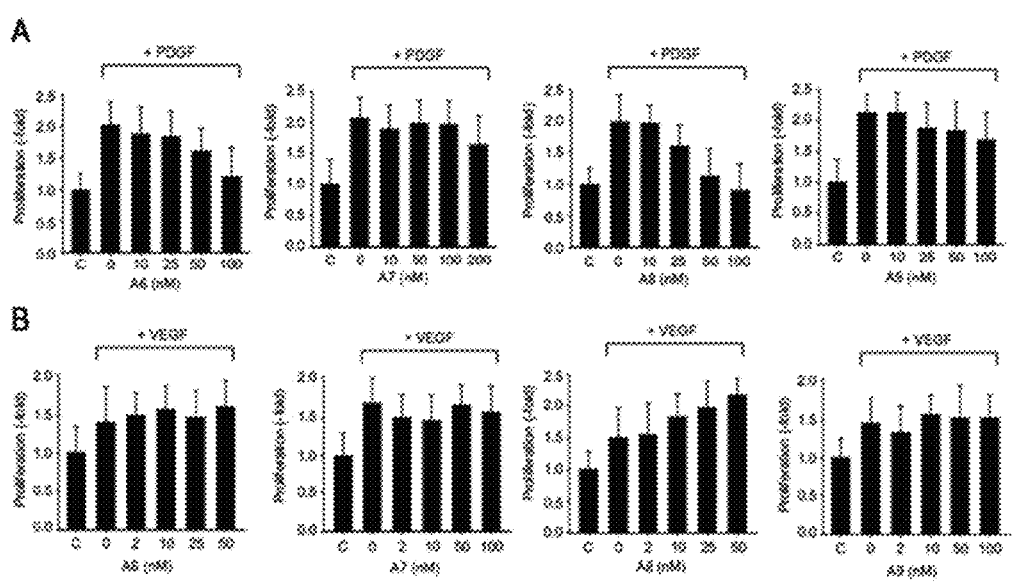
FIG. 20 is a diagram showing the effects of Compounds A6 to A9 according to the present invention on the growth factor-induced proliferation of PrxII knocked down vascular cells. A represents the effects on the proliferation of HASMC in response to PDGF, and B represents the effects on the proliferation of HAEC in response to VEGF.
Figure 21:
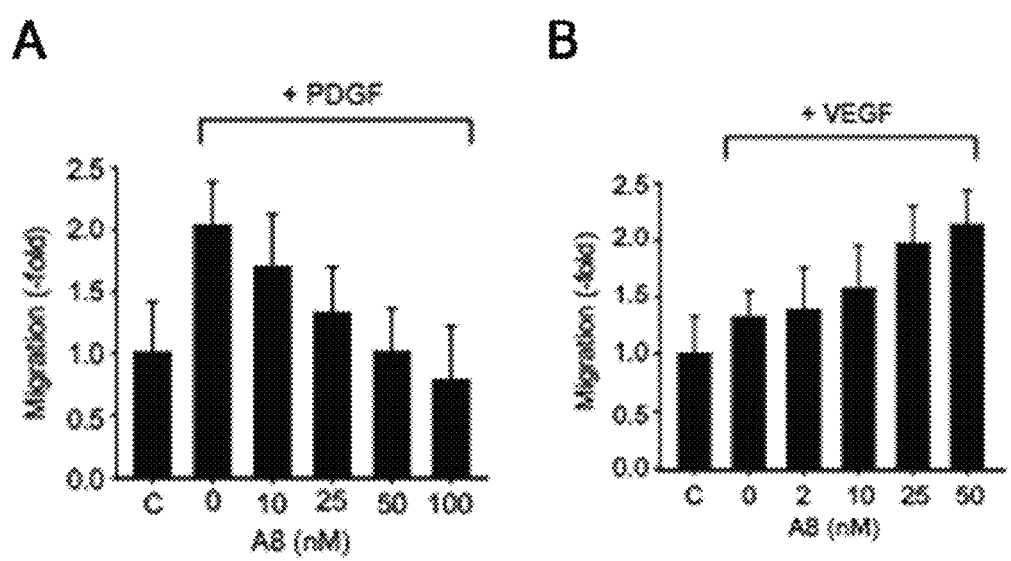
FIG. 21 is a diagram showing the effects of Compound A8 according to the present invention on the growth factor-induced migration of PrxII knocked down vascular cells. A represents the effects on the migration of HASMC in response to PDGF, and B represents the effects on the migration of HAEC in response to VEGF.

Furthermore, A2R, A4R and A5R with exposed thiol groups were used to compare the results. As a result, no significant changes were observed in both HASMCs and HAECs (FIGS. 16 and 18).

It is noteworthy that nanomolar concentrations of ETP derivatives A1 to A9, which does not exhibit cytotoxicity, are sufficient to regulate RTK signaling and cell function in HASMCs and HAECs. Particularly, it was demonstrated that A1 to A3, A5 and A8 having relatively small substituents or a small number of substitutents exhibited excellent activities, and A6 and A9 exhibited moderate activities. Collectively, the experimental results described above indicate that low concentrations of the ETP derivatives may restore the injured PDGF- and VEGF-induced signaling due to PrxII deficiency.

Experimental Example 4: Effects of ETP Compound on NADPH Oxidase (NOX) Activity

Figure 22:
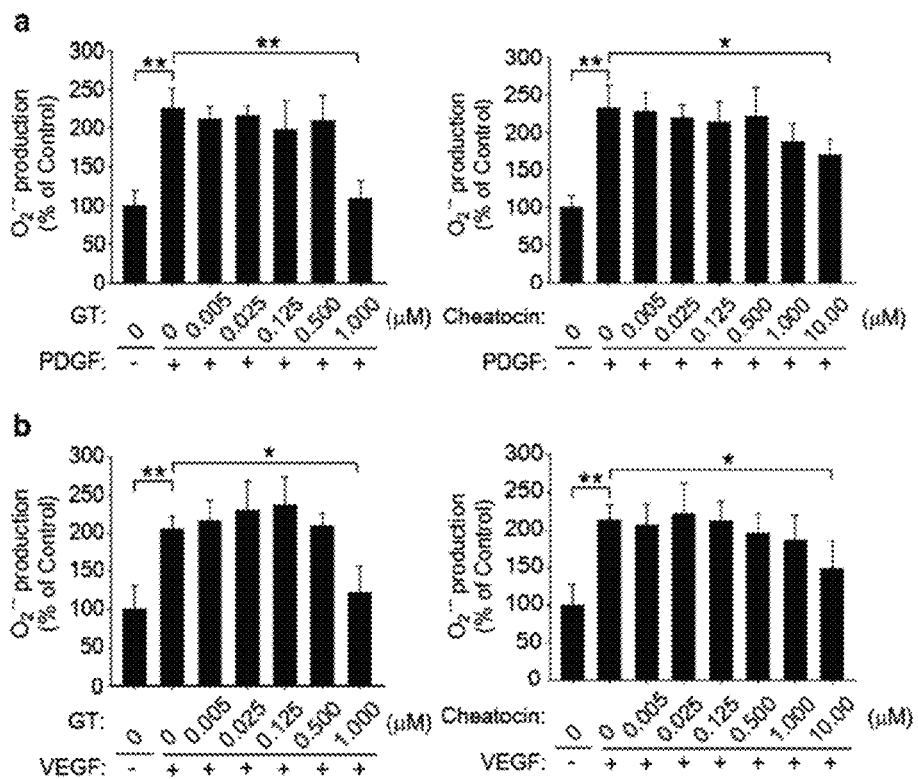
FIG. 22 is a diagram showing the effects of GT and chaetocin on the NOX activity in HASMCs and HAECs.

When HASMCs and HAECs were stimulated with PDGF-B and VEGF-A, respectively, the NOX activity increased approximately twofold. However, the treatments with GT and cheatocin did not inhibit the NOX activity until the concentrations of the compounds increased up to 500 nM, which exceeds the toxic limit (FIG. 22). Thus, it was seen that these ETP compounds function as hydrogen peroxide reductase capable of replacing PrxII in both vascular cells, but the mechanism was not the inhibition of hydrogen peroxide producer NOX.

Experimental Example 5: Identification of 2-Cys-Prx, Particularly, PrxII Overoxidation for Balloon-Injured Carotid Arteries Through In Vivo Experiments The effects of the ETP compounds were identified in vivo using an experimental animal model of vascular injury (balloon-induced injury of rat carotid artery) capable of monitoring the hyperplasia of VSMCs and vascular reendothelialization. When the arteries are injured by the insertion of a balloon catheter, the endothelium is denuded.

Therefore, the platelets and macrophages are accumulated in the injured lesion to repair the injured vessel. These cells produce active oxygen radicals including hydrogen peroxide, therefore, the 2-Cys Prx enzymes in neighboring vascular cells are presumed to be inactivated by overoxidation of the active site cysteine residue to sulfinic/sulfonic acids ($Cys-SO_{2/3}$). To address this possibility, the overoxidation of 2-Cys Prxs in the balloon-injured rat carotid arteries was examined using an anti-$Prx-SO_{2/3}$ antibody. The balloon injury induced the intimal hyperplasia of carotid arteries along with time (FIG. 23a), and the immunohistochemical analysis showed that the overoxidation of 2-Cys Prxs was profound in both inner and vascular intimal layers at the $5^{th}$ and $7^{th}$ days after the injury (FIG. 23b). The immune-reactive signaling specificity was demonstrated by blocking with the corresponding antigenic peptide in hydrogen peroxide-treated normal vessels. The immunoblot analysis affirmed that the overoxidation of major 2-Cys Prxs was induced by balloon injury. When PrxI and PrxII were separated by immunoprecipitation with an anti-PrxI antibody, the overoxidation of PrxII was found to be dominantly enhanced along with intimal hyperplasia compared to those of PrxI and PrxIII (FIG. 23c). This is in contrast to the hydrogen peroxide-treated control vessel where the PrxI overoxidation is obvious. The negative regulatory role of PrxII in the PDGF-dependent growth of VSMCs demonstrates that the inactivation of PrxII by overoxidation contributes to the SMC hyperplasia in injured vessel walls. Indeed, the siRNA-mediated knockdown of the PrxII expression in carotid arterial walls exacerbated the intimal hyperplasia induced by balloon injury (FIG. 24).

Next, the inventors of the present invention assessed whether GT orchestrated the proper repair of the injured vessel where the PrxII overoxidation occured. When the GT solution was locally administered at various concentrations to the lumen of the carotid arterial vessels through the catheter after balloon injury, the intimal hyperplasia was notably suppressed in a concentration dependent manner within a nanomolar range that did not induce cell death, as identified by TUNEL staining (FIG. 25a). This result indicates that GT suppresses SMC hyperplasia.

In addition, as a control experiment, bis(methylthio)gliotoxin having methylated dithiol groups and TR inhibitor (DNCB 5 µM, or Auronafin 0.5 µM) were treated either alone or as a combination with GT, and the HE-stained images for tissues were observed.

The result showed that bis(methylthio)gliotoxin did not suppress the thickened vascular intimal layer, and TR inhibitors all canceled out the intimal hyperplasia suppression effects of GT (FIG. 26). Therefore, it was seen that bis (methylthio)gliotoxin with methylated thiol groups was not effective in repairing vascular injury, and GT was effective in repairing vascular injury through TR regulation.

Subsequently, experiments to identify whether GT actually promoted the endothelial repair in the injured vessel walls were carried out. The immunofluorescence staining of endothelial marker CD31 clearly revealed that, as in normal carotid vessels, an endothelium monolayer in contact with lumen was formed in GT-treated injured vessels, while the monolayer was not formed in control injured carotid arteries (FIG. 25b). In addition, co-immunostaining with α-smooth muscle actin (SMA) further demonstrated that the endothelial layer was covered on top of the vascular intimal SMC layer.

In addition, immunohistochemistry staining was carried out using an overoxidized 2-Cys-Prx ($Prx-SO_{2/3}$) antibody in order to identify the effects of GT on the overoxidation of 2-Cys-peroxiredoxin (2-Cys-Prx), and as the DAB-stained images, representative images among 5 different carotid artery samples were shown. As a result, as shown in FIG. 27, there were no significant differences in the sample data between the control group and the GT-treated group. This result affirms that GT does not inhibit the oxidation of 2-Cys-Prx, but replaces the function of 2-Cys-Prx in the cells after overoxidation instead.

In addition, it was identified whether A1 to A3, A5, A6 and A8, the ETP derivatives according to the present invention, may inhibit the proliferation of aortic smooth muscle cells.

Specifically, whether the derivative orchestrates the proper repair of the injured vessel where the PrxII overoxidation occurs was identified. The solution including the derivative was locally administered at a concentration of 200 nM to the lumen of the carotid arterial vessels through a catheter after the balloon injury, and the HE-stained images for tissues were observed.

The result, as shown in FIG. 28, showed that the ETP derivatives according to the present invention all effectively inhibited the smooth muscle cell proliferation.

Subsequently, the experiments to identify whether the derivatives A1 to A3, A5, A6 and A8 actually promoted the endothelial repair in the injured vessel walls were carried out. The immunofluorescence staining of the endothelial marker CD31 verified that, while an endothelium monolayer in contact with the lumen was formed in the injured vessels treated with A1 to A3, A5, A6 or A8, the monolayer was not formed in control injured carotid arteries (FIG. 29). In addition, co-immunostaining with α-smooth muscle actin (SMA) further demonstrated that the endothelial layer was covered on top of the vascular intimal SMC layer.

Experimental Example 6: Vascular Permeability Test

The permeability of the repaired endothelium was examined by Evans blue inflow. The endothelial denudation by balloon injury resulted in the complete loss of permeability controlling activity, whereas the uninjured collateral carotid arteries showed the intact barrier function of normal endothelium (FIG. 30a). The GT treatment for balloon injured carotid arteries resulted in approximately two-third reduction in Evans blue inflow compared to control group (DMSO)-treated injured carotid arteries. More evidently, the recovery of endothelial function induced by GT was blocked by a VEGFR2 kinase-specific inhibitor, suggesting that the effects of GT protected the VEGFR2 function from oxidative inactivation induced by the overoxidation of PrxII.

The interendothelial junction on the luminal surfaces of the injured carotid arterial vessels was examined by a scanning electron microscopy. Endothelial cells in the carotid artery of a GT-treated rat were spread and formed a uniform layer with tight junction, whereas those in carotid artery of a control-treated rat were shrunken and patched (FIG. 30b). The results collectively indicate that the endothelium repaired by the GT treatment is functionally and structurally intact, thereby is sufficient for controlling vascular permeability.

Experimental Example 7: Effects of Chaetocin, Chetomin and Other Anti-oxidant Compounds The inventors of the present invention tested whether other ETP compounds such as chaetocin and chetomin also induce the proper repair of injured vessels. The efficacy of chaetocin in vascular cell function was first evaluated. The chaetocin treatment with increasing concentrations markedly reduced the proliferation and the chemotactic transmigration of HASMCs in response to PDGF, which had been enhanced by the PrxII knockdown (FIGS. 31a and 31b). Conversely, the same treatment resulted in a remarkable enhancement in VEGF-induced proliferation and chemotactic transmigration of HAECs, which had been impaired by the PrxII knockdown (FIGS. 31c and 31d). As mentioned in Experimental Example 2, chaetocin was less cytotoxic than GT, therefore, the efficacy of chaetocin regulating the function of VSMCs and VECs was important even at high nanomolar concentrations. In parallel with such in vitro activities, the chaetocin treatment markedly blocked the intimal hyperplasia and concomitantly promoted re-endothelialization in an injured arterial wall (FIGS. 32a and 32c), indicating that, in addition to GT, chaetocin also functions as reciprocal regulator of VSMCs and VECs. Chetomin also exhibited similar effects in the repair of injured arterial walls (FIGS. 32b and 32d). Collectively, it was demonstrated that the ETP series compounds act as ideal therapeutic agents for repairing vascular injuries.

Lastly, the effects of GT, a representative ETP compound, on vascular cells were compared with the effects of other compounds known as anti-oxidant compounds such as N-acetylcysteine or butylated hydroxyanisole, and the results are shown in FIG. 33. Immunoblotting was performed by pretreating HAECs in which PrxII was knocked down by injecting siRNA with each compound at the concentrations indicated in the graphs for two hours, and then treating with VEGF for 10 minutes. The result showed that N-acetylcysteine or butylated hydroxyanisole did not induce the activation of VEGFR2 and downstream ERK even when used with $10^3$ to $10^4$-fold higher concentrations than the concentration of GT. These comparative experiments led the inventors of the present invention to conclude that the distinguished cytotoxic function of the ETP compounds is clearly due to the PrxII-analogous activity, and additionally to the special chemical property of the dithioketopiperazine ring.

Experimental Example 8: Identification of Effects of GT on PrxII-deficient Vascular Cells and Mouse Aortic vascular smooth muscle (A) and endothelial cells (B) were separated from a normal mouse and a PrxII−/− mouse, and cultured, and then treated with PDGF-BB and VEGF-A for 10 minutes each after either treating with GT or no treating. The activation of PDGFRβ, PLCγ1, VEGFR2 and ERK was analyzed using a phosphorylation-specific binding antibody for each protein. The result verified that, as shown in A and B of FIG. 34, the opposed regulatory effects of GT on PDGF signaling and VEGF signaling in the vascular smooth muscle cells (VSMC) and the vascular endothelial cells (VEC), respectively, which were separated from the Prx−/− mouse.

In addition, in order to identify the effects of GT on vascular thickening in a PrxII−/− mouse, left carotid artery of a PrxII−/− mouse was damaged using a flexible wire. After the injury, a Whatman No. 1 filter paper strip was soaked in a control vehicle or a GT solution, and the paper was attached to the surface of vascular epithelia for 30 minutes for the solution to permeate into the tissue. The mouse was recovered at the $10^{th}$ day after the injury. As a result, the ratio of intima versus media measured from the HE-stained carotid artery sample was presented as mean+− standard error (n=8 per group, *p<0.01). The result indicated that, as shown in FIG. 34C, GT markedly reduced the vascular thickening.

Experimental Example 9: Inhibition Effects of PrxII on Proliferation and Migration of Melanoma Cells, and Identification of Inhibiting Melanoma Cells from In Vitro Migration and In Vivo Metastasis to Lung by Treating Melanoma Cells with ETP Compound or its Derivatives (1) Identification of Relation Between Proliferation and Migration of Melanoma Cells and PrxII Suppression Melanoma cells were immunoscreened for the PrxII protein level using a PrxII-specific antibody. While SK-MEL-5 (SK5) and SK-MEL-28 (SK28) melanoma cells scarcely expressed PrxII, two other cell lines, A375 and G361, expressed PrxII protein (FIG. 47A). The PrxII expression level in A375 was similar to the level of human melanocyte. Conversely, the protein levels of the most similar isoform PrxI were identical in the 4 cell lines. In addition, the promotor region of Prdx2 genes in the SK-MEL cell line was methylated, but not in A375 and G361 cells. This provides the molecular mechanism involving in the silencing of PrxII expression. The level of cellular hydrogen peroxide level was measured using DCFH-DA, an oxidation-sensitive dye, considering that PrxII is a cytoplasmic antioxidant enzyme.

Consequently, the basic hydrogen peroxide level appeared to be high in the PrxII-deficient SK-MEL cells while the level was low not only in primary melanocyte in which PrxII was present but also in A375 and G361 (FIG. 47B). This suggests that PrxII is an important antioxidant enzyme regulating the intracellular hydrogen peroxide level in melanoma cells.

Furthermore, in vitro cell activities such as proliferation and migration of 4 melanoma cell types were compared. The serum condition is physiologically related to tumor metastasis involving complex factors, therefore, the cells were in a serum-starved condition and then stimulated with 20% fetal serum in order to maximize the inducement of serum-dependent cell activities. As a result, the PrxII-deficient SK-MEL cells exhibited a higher proliferation activity compared to 2 other PrxII-expressed melanoma cells (FIG. 47C). The migratory activity exhibited in the chemotactic transmigration for serum and the wound closure was higher in the SK-MEL cells than in other PrxII-expressed melanoma cells (FIGS. 47D and E). This suggests an inverse relationship between the cell function and the PrxII level in melanoma cell types.

In addition, the direct regulatory effects of PrxII on melanoma cells regarding the exogenous expression and the specific knockdown of PrxII were identified. The exogenous expression of PrxII in the SK-MEL cells was achieved by the retroviral transduction of human Prdx2 genes (FIG. 48A). When the proliferative activity of the SK-MEL cells was identified, the retroviral expression of PrxII reduced the proliferation of cells induced by serum stimulation (FIG. 48B). The migratory activity of the SK-MEL cells exhibited in the chemotactic transmigration and the wound closure was far more reduced by the PrxII expression (FIGS. 48C and D). Subsequently, the PrxII expression was specifically knocked down in G361 and A375 cells using 2 different siRNA (FIG. 49A). PrxII knockdown significantly increased the cell proliferation and migration responding to serum stimulation in both cells (FIGS. 49B and C). Conversely, the knockdown of PrxI, another cytoplasmic Prx isoform, did not affect melanoma cell activities (FIG. 49D). Collectively, this indicates that the PrxII enzyme acts as a selective antioxidant inhibitor for the proliferation and the migration of melanoma cells.

(2) Metastasis Increase of Melanoma Cells to Lung Due to PrxII Absence

In the proliferation and the migration of melanoma cells, in vivo experiments were performed using a metastasis to lung model with B16F10, a mouse melanoma cell, based on the regulatory activity of PrxII. B16F10 cells are known to express wild-type BRAF, therefore, it was identified that PrxII still regulated B16F10 cell activities and Src/ERK pathway. In the B16F10 cells, the PrxII knockdown using mouse PrxII-specific siRNA reduced the level of E-cadherin while increasing the Src/ERK activation and the β-catenin phosphorylation (FIG. 52A). Consistent with this, the PrxII knockdown increased the proliferation and the migration of B16F10 responding to serum stimulation (FIG. 52B). This indicates that the fuction of PrxII in melanoma cells may be independent from oncogenic BRAF mutation.

For in vivo experiments, the stable deficiency of PrxII expression was guaranteed during the metastasis to lung assay using siRNA-mediated knockdown of PrxII expression (FIG. 52C). After that, mPrxII siRNA-transfected B16F10 cells were injected to a mouse via a tail vein. After 10 days, the lung of the mouse was removed and the metastasized tumor nodules were identified. A microscopic examination on both the lung surface and the HE-stained issue section revealed that PrxII-knocked down B16F10 cells more aggressively infiltrated into the lung, and invaded and colonized the lung than control group cells (FIGS. 52D and E).

(3) In Vitro Migration Inhibition and In Vivo Metastasis to Lung Inhibition of Melanoma Cells by ETP Derivative and Gliotoxin Treatment The fungal secondary metabolite known as gliotoxin (GT) is a first natural product known to exhibit a thioredoxin-dependent peroxidase activity represented as a typical Prx activity, therefore, the treatability of GT for melanoma metastasis inhibition was identified. GT treatment at the nontoxic level actually reduced the level of intracellular hydrogen peroxide in the PrxII-deficient SK28 cells (FIG. 53A). This proves the peroxidase activity of GT. Again, while GT treatment in the SK28 cells reduced Src/ERK activation and β-catenin phosphorylation, it increased the expression of E-cadherin (FIG. 53B). Furthermore, GT reduced the proliferation and the migration responding to serum stimulation in both SK5 and SK28 cells (FIGS. 53C and D). This indicates that GT acts as a small molecule substitute for PrxII in melanoma cells. In order to demonstrate the in vivo treatment efficiently, GT was injected to a mouse intraperitoneally after B16F10 cells were injected. The GT treatment significantly reduced the metastasis to lung in the melanoma cells (FIG. 53E). In addition, GT more significantly reduced the metastasis of the PrxII-knocked down B16F10 to lung (FIG. 53F). This indicates that GT has potential as a therapeutic agent for inhibiting metastasis to lung since it may act as a small molecule substituent for PrxII as a melanoma metastasis inhibitor.

In addition, whether chaetocin and chetomin inhibited the activities of melanoma cells were identified.

Specifically, after chaetocin and chetomin was treated with SK-MEL28 melanoma cells at different concentrations (0, 100, 200, 500 and 1000 nM), the cell viability was checked, and the result is shown in FIG. 54A. As shown in FIG. 54A, toxicity was not shown at a concentration of 100 nM, and consequently, 100 nM was used in the following proliferation and migration experiments.

Accordingly, chaetocin and chetomin were treated with SK-MEL28 melanoma cells at 100 nM for 1 hours, and the proliferative and migratory activities were checked, and the proliferation and the migration were promoted with serum (FBS).

As shown in FIGS. 54 B and C, the result indicated that the treatment with chaetocin and chetomin effectively impeded both the proliferation and the migration of melanoma cells.

In addition, in order to demonstrate the in vivo treatment efficiently, chaetocin and chetomin were injected to a mouse intraperitoneally after B16F10 cells were injected. The treatment with chaetocin and chetomin significantly reduced the metastasis to lung in melanoma cells (FIG. 55).

Accordingly, it may be inferred that the ETP derivatives according to the present invention mimicking in vivo PrxII activity may also exhibit similar activities for melanoma metastasis inhibition through the PrxII activation.

Metastatic malignancy is the most crucial issue in vertical growth phase melanoma. Despite that major genes or signaling networks relating to melanoma metastasis have been established, there are no evidences regarding which antioxidant enzymes are involved. The inventors of the present invention first established that the level of PrxII is inversely correlated to the metastasis activities of melanoma cells. It was demonstrated that the SK-MEL melanoma cells having silenced PrxII expression had more superior proliferative and migratory activities compared to A375 and G361 cells highly expressing PrxII. While exogenous reexpression of PrxII in the SK-MEL cells reduced the proliferation and the migration of cells, PrxII knockdown in A375 and G361 cells increased both cell activities. At a molecular level, PrxII was regulated in the directions to reduce Src/REK activities, and the sustenance of E-cadherin and Y654 phosphorylation-independent β-catenin were tightened one by one in plasma membrane. The PrxII-deficient mouse melanoma B16F10 cells showed improved metastasis to lung in vivo. Interestingly, gliotoxin, a natural compound exhibiting a Prx-analogous activity, inhibited not only metastasis of PrxII-deficient melanoma cells to lung but also the proliferation and the migration. Accordingly, the present invention demonstrated that PrxII and its small molecule mimetic have a possibility as potential therapeutic agents to be used as an inhibitor for melanoma metastasis.

From the descriptions above, it will be apparent to those skilled in the art that the present invention may be executed in other specific manners without changing the technological ideas and essential features. Regarding this, it is to be understood that the examples described above are for illustrative purposes in all aspects, and are not limitative. The scope of the present invention needs to be interpreted to include all modifications or modified forms deduced from the meaning, the scope, and the equivalent concepts of Claims described below rather than detailed descriptions made above.

What is claimed is:

1. A method for preparing an epidithiodioxopiperazine derivative represented by the following Chemical Formula 1 or its reduced derivative, or a pharmaceutically acceptable salt thereof, said derivative having improved intracellular permeability and mimicking the activity of 2-Cys-Prx in its reduced form in the cells, the method comprising preparing an intermediate represented by the following Chemical Formula 4 by reacting a piperazinedione derivative represented by the following Chemical Formula 3 with sulfur (S) and lithium bis(trimethylsilyl)amide (LiHMDS) or NaH-MDS;

preparing the dimercaptopiperazinedione derivative represented by Chemical Formula 2 by reducing the intermediate; and forming an intramolecular disulfide bridged bond from a dimercaptopiperazinedione derivative represented by the following Chemical Formula 2 using an oxidation reaction:

[Chemical Formula 1]

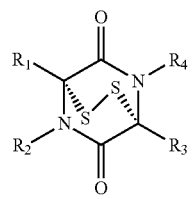

[Chemical Formula 2]

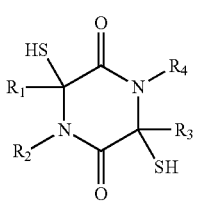

[Chemical Formula 3]

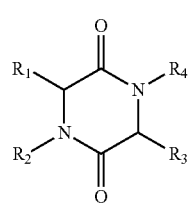

[Chemical Formula 4]

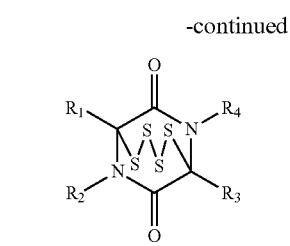

wherein, in Chemical Formulae 1 to 4, $R_1$ to $R_4$ are each independently hydrogen, a halogen atom, a hydroxyl group, linear or branched C1 to C6 alkyl, alkenyl or alkynyl, linear or branched C1 to C6 alkoxy, linear or branched C1 to C6 hydroxyalkyl, substituted or unsubstituted benzyl, linear or branched C1 to C6 alkylaryl, a linear or branched C1 to C6 perfluoroalkyl group, a substituted or unsubstituted aryl group, a substituted or unsubstituted perfluoroaryl group, a substituted or unsubstituted heteroaryl group comprising an oxygen, nitrogen or sulfur atom in a ring as a heteroatom, or a substituted or unsubstituted epidithiodioxopiperazine group, and the alkyl and the aryl group may optionally include a heteroatom of oxygen, nitrogen or sulfur in the middle of the chain, and each of the substituted epidithiodioxopiperazine groups may independently optionally include the substituents defined above and have a structure identical to or different from mother nucleus epidithiodioxopiperazine; or $R_1$ and $R_2$, and $R_3$ and $R_4$ each independently form a substituted or unsubstituted C3 to C6 cycloalkyl group with a carbon atom to which these are attached; or form a substituted or unsubstituted heterocyclic ring having 5 to 8 ring atoms with a carbon atom to which these are attached, and additional carbon or heteroatoms, and herein, 1 or 2 ring atoms of the heterocyclic ring are selected from nitrogen (N), oxygen (O) or sulfur (S); however, compounds represented by the following Chemical Formulae 15 to 46 are not included Chemical Formula 15

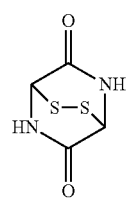

Chemical Formula 16
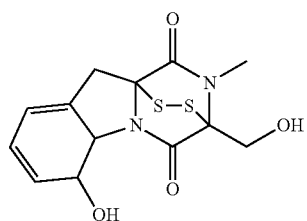
Chemical Formula 17
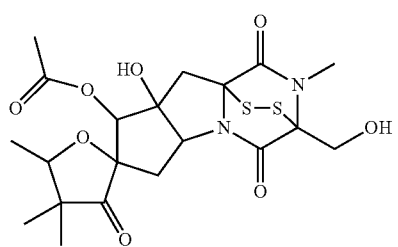
Chemical Formula 18
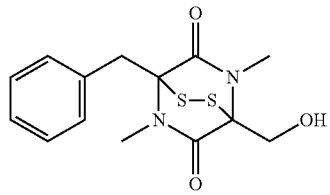
Chemical Formula 19
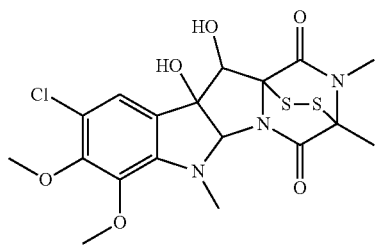
Chemical Formula 20
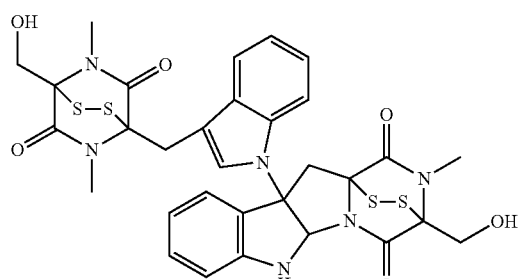
Chemical Formula 21
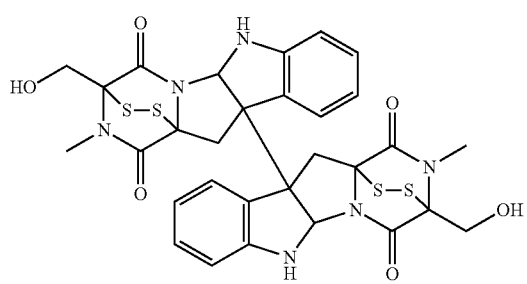
Chemical Formula 22
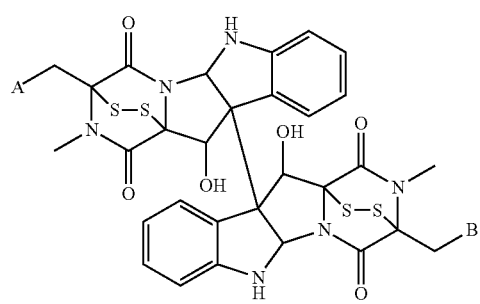
A and B are each independently hydrogen; methoxy; or a hydroxyl group.
Chemical Formula 23
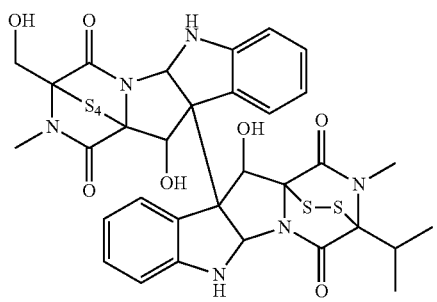
Chemical Formula 24
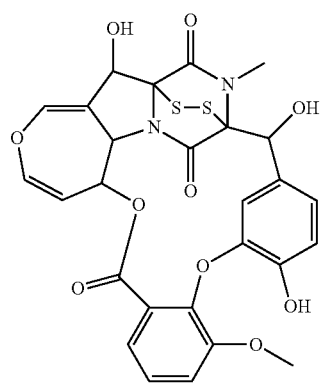
Chemical Formula 25
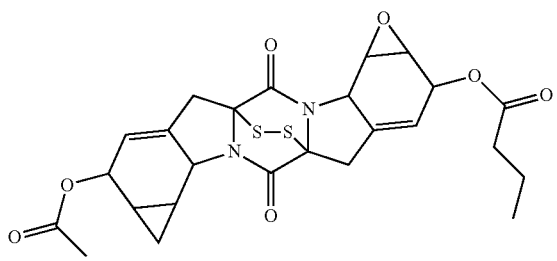
Chemical Formula 26
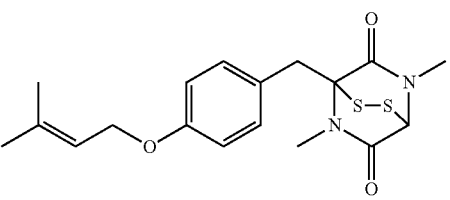

77
-continued
Chemical Formula 27
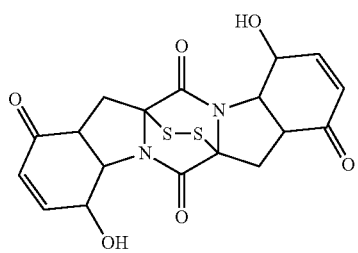
Chemical Formula 28
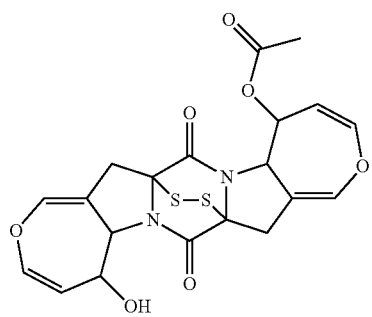
Chemical Formula 29
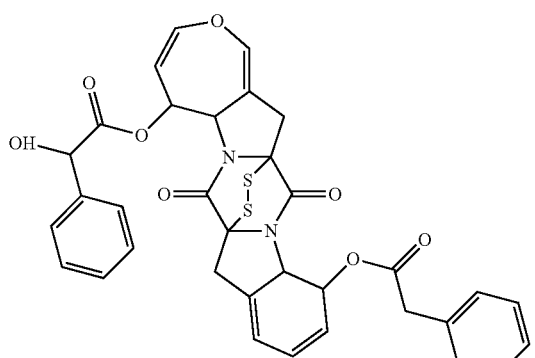
Chemical Formula 30
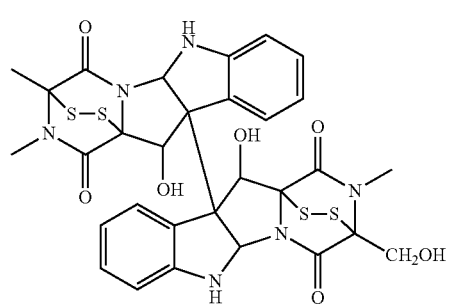
Chemical Formula 31
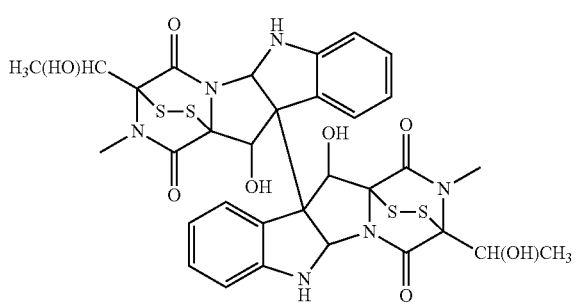
78
-continued
Chemical Formula 32
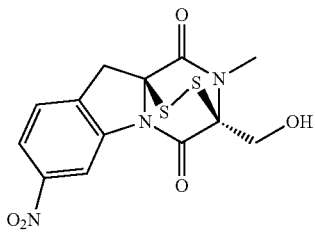
Chemical Formula 33
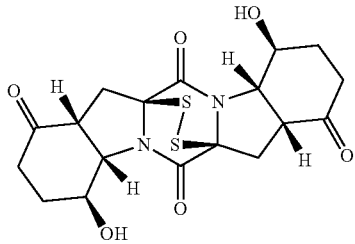
Chemical Formula 34
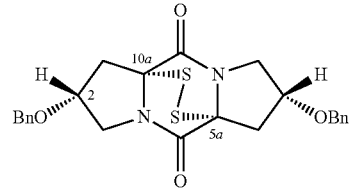
Chemical Formula 35
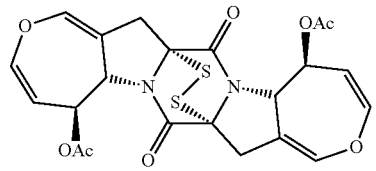
Chemical Formula 36
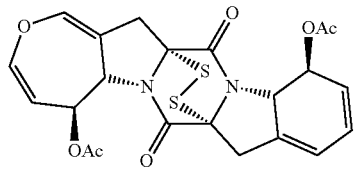
Chemical Formula 37
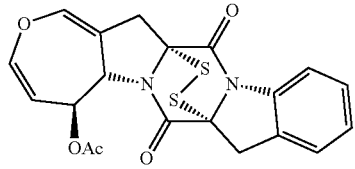
Chemical Formula 38
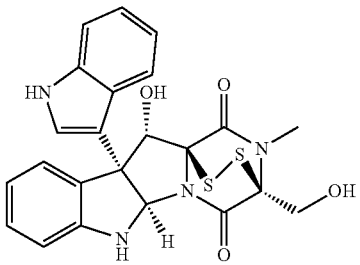

-continued

Chemical Formula 39
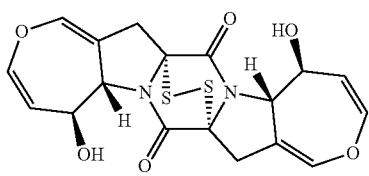

Chemical Formula 40
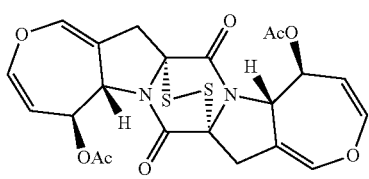

Chemical Formula 41
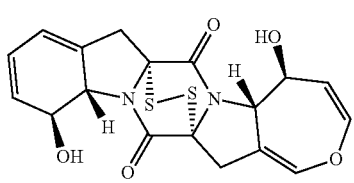

Chemical Formula 42
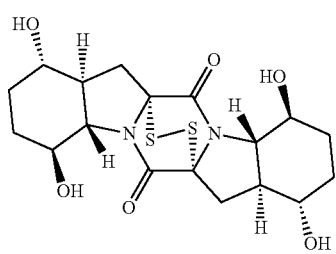

Chemical Formula 43
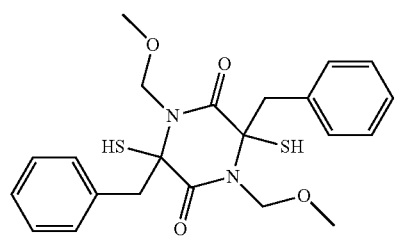

Chemical Formula 44
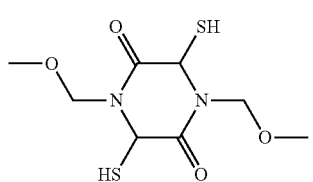

Chemical Formula 45
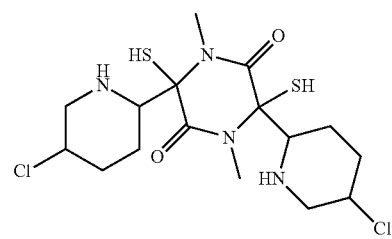

-continued

Chemical Formula 46
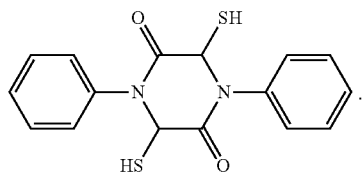

2. A method for preparing an epidithiodioxopiperazine derivative represented by the following Chemical Formula 1 or its reduced derivative, or a pharmaceutically acceptable salt thereof, said derivative having improved intracellular permeability and mimicking the activity of 2-Cys-Prx in its reduced form in the cells, the method comprising preparing an intermediate represented by the following Chemical Formula 6 including a thioacetate group by reacting a halogen atom-substituted piperazinedione derivative represented by the following Chemical Formula 5 with an alkali metal salt of thioacetic acid (MSAc); preparing the dimercaptopiperazinedione derivative represented by Chemical Formula 2 by reacting the intermediate with an acid solution; and forming an intramolecular disulfide bridged bond from a dimercaptopiperazinedione derivative represented by the following Chemical Formula 2 using an oxidation reaction:

[Chemical Formula 1]
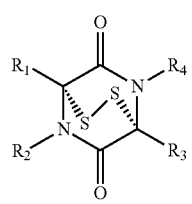

[Chemical Formula 2]
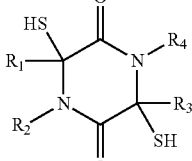

[Chemical Formula 5]
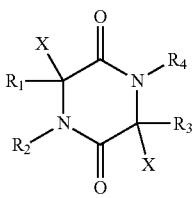

[Chemical Formula 6]
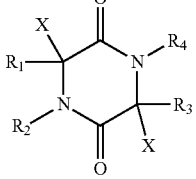

wherein, in Chemical Formulae 1, 2, 5, and 6,
$R_1$ to $R_4$ are each independently hydrogen, a halogen atom, a hydroxyl group, linear or branched C1 to C6 alkyl, alkenyl or alkynyl, linear or branched C1 to C6 alkoxy, linear or branched C1 to C6 hydroxyalkyl, substituted or unsubstituted benzyl, linear or branched C1 to C6 alkylaryl, a linear or branched C1 to C6 perfluoroalkyl group, a substituted or unsubstituted aryl group, a substituted or unsubstituted perfluoroaryl group, a substituted or unsubstituted heteroaryl group comprising an oxygen, nitrogen or sulfur atom in a ring as a heteroatom, or a substituted or unsubstituted epidithiodioxopiperazine group, and the alkyl and the aryl group may optionally include a heteroatom of oxygen, nitrogen or sulfur in the middle of the chain, and each of the substituted epidithiodioxopiperazine groups may independently optionally include the substituents defined above and have a structure identical to or different from mother nucleus epidithiodioxopiperazine; or R$_1$ and R$_2$, and R$_3$ and R$_4$ each independently form a substituted or unsubstituted C3 to C6 cycloalkyl group with a carbon atom to which these are attached; or form a substituted or unsubstituted heterocyclic ring having 5 to 8 ring atoms with a carbon atom to which these are attached, and additional carbon or heteroatoms, and herein, 1 or 2 ring atoms of the heterocyclic ring are selected from nitrogen (N), oxygen (O) or sulfur (S); however, compounds represented by the following Chemical Formulae 15 to 46 are not included Chemical Formula 15

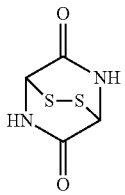

Chemical Formula 16

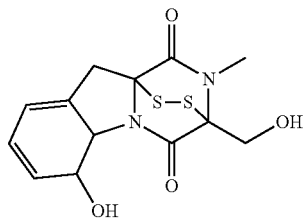

Chemical Formula 17

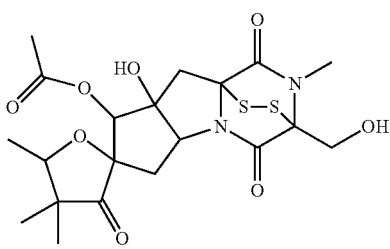

Chemical Formula 18

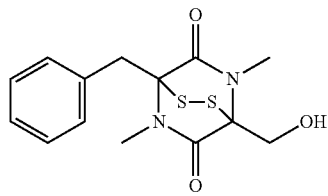

Chemical Formula 19

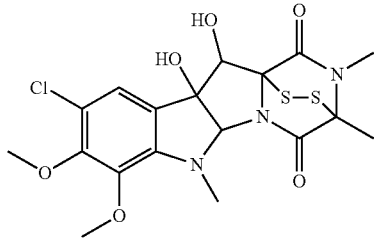

Chemical Formula 20

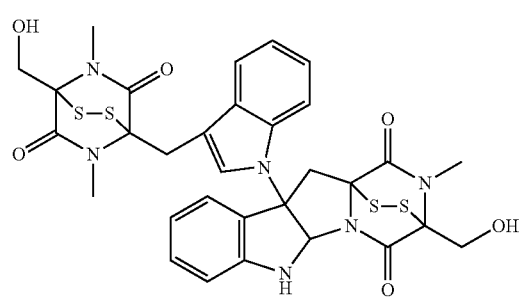

Chemical Formula 21

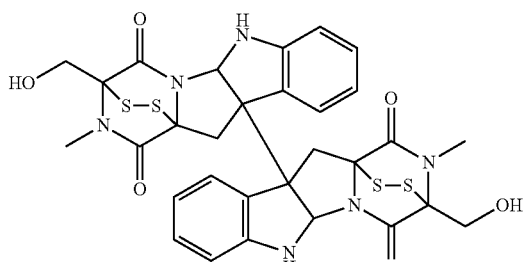

Chemical Formula 22

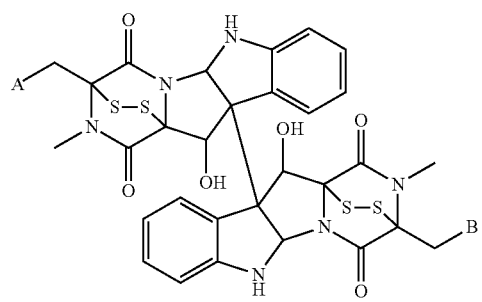

A and B are each independently hydrogen; methoxy; or a hydroxyl group.

Chemical Formula 23

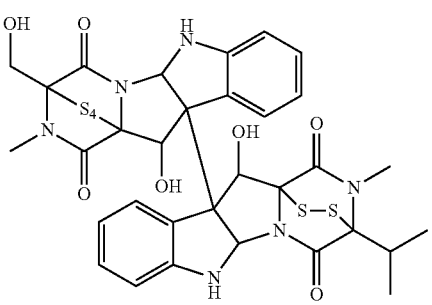

-continued
Chemical Formula 24
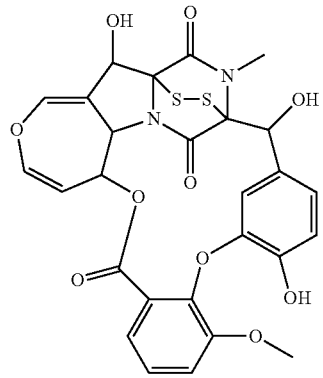
Chemical Formula 25
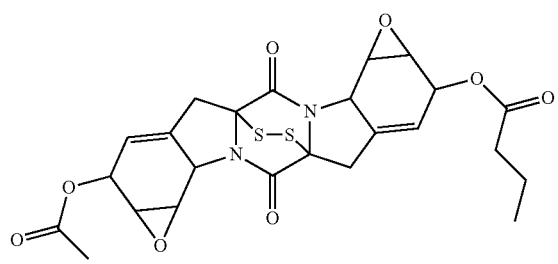
Chemical Formula 26
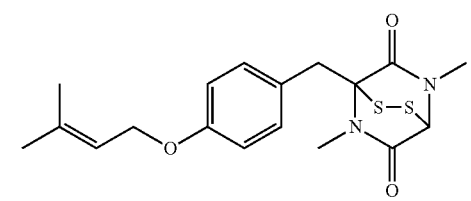
Chemical Formula 27
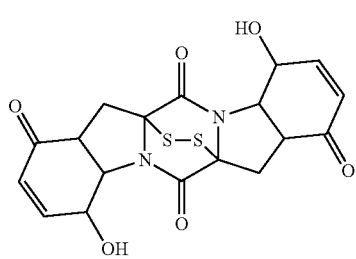
Chemical Formula 28
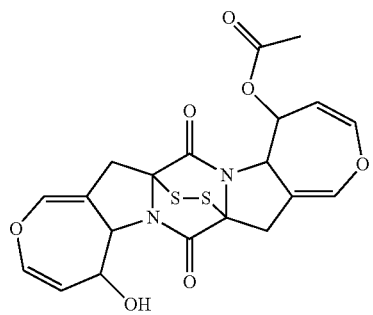
-continued
Chemical Formula 29
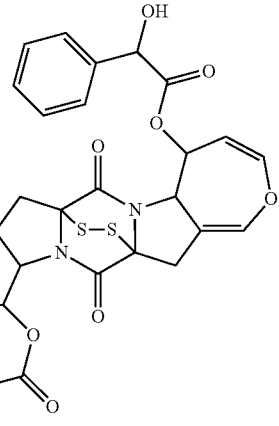
Chemical Formula 30
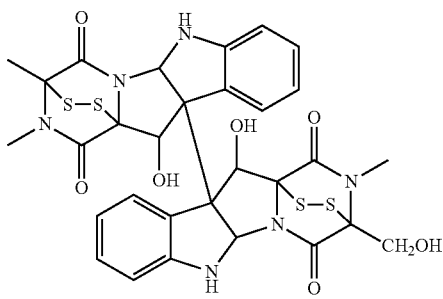
Chemical Formula 31
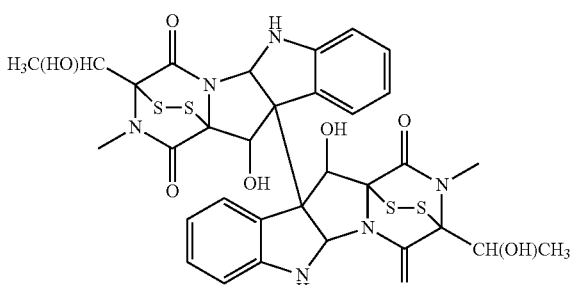
Chemical Formula 32
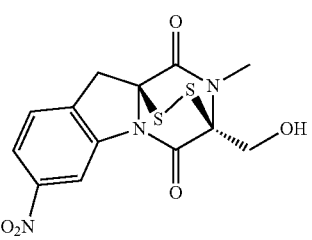
Chemical Formula 33
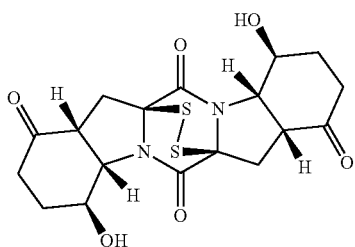

Chemical Formula 34

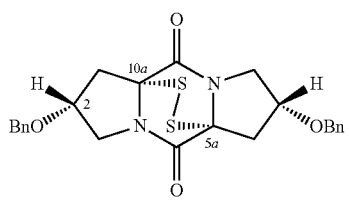

Chemical Formula 35

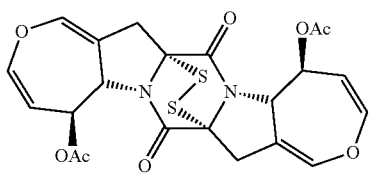

Chemical Formula 36

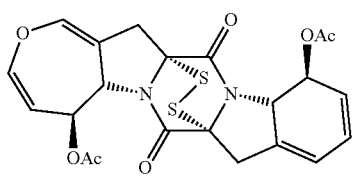

Chemical Formula 37

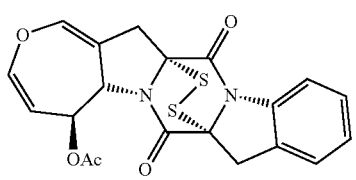

Chemical Formula 38

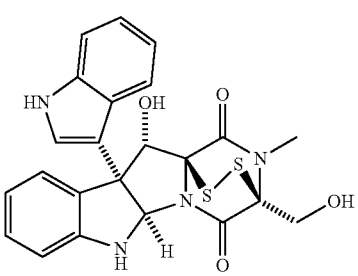

Chemical Formula 39

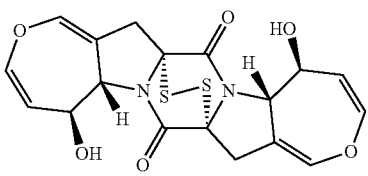

Chemical Formula 40

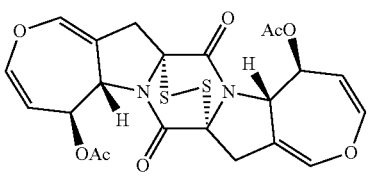

Chemical Formula 41

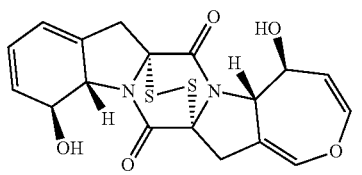

Chemical Formula 42

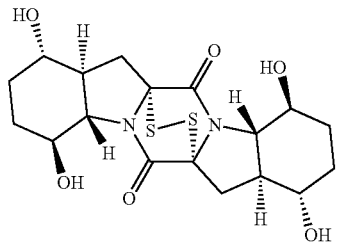

Chemical Formula 43

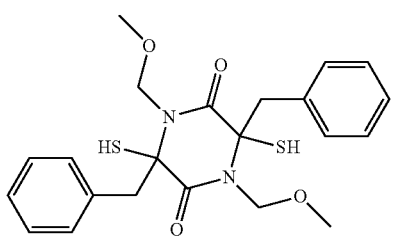

Chemical Formula 44

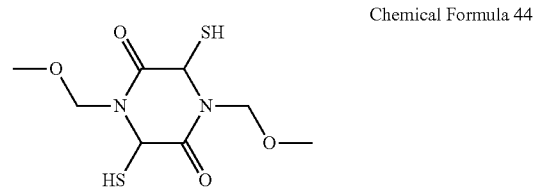

Chemical Formula 45

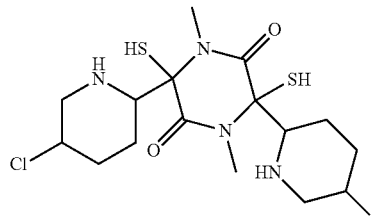

Chemical Formula 46

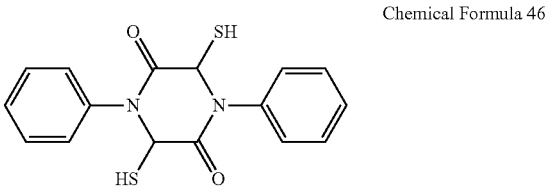

wherein, the alkali metal salt is a sodium or potassium salt, and X is a halogen atom.

3. The method of claim 1, wherein $R_1$ to $R_4$ are each independently hydrogen, linear or branched C1 to C6 alkyl or alkenyl, alkoxybenzyl, alkoxyalkyl or benzhydryl.

4. The method of claim 1, wherein $R_1$ to $R_4$ are each independently hydrogen, methyl, n-butyl, allyl, 4-methoxybenzyl, 3-methoxypropyl or benzhydryl.

5. The method of claim 1, wherein the epidithiodioxopiperazine derivative is any one of compounds represented by the following Chemical Formulae 7 to 14:

[Chemical Formula 7]
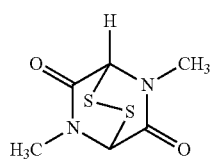

[Chemical Formula 8]
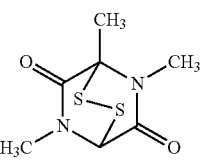

[Chemical Formula 9]
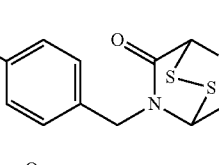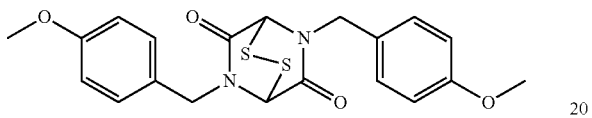

[Chemical Formula 10]
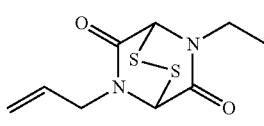

[Chemical Formula 11]
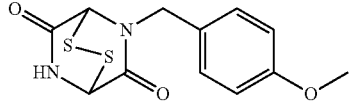

[Chemical Formula 12]
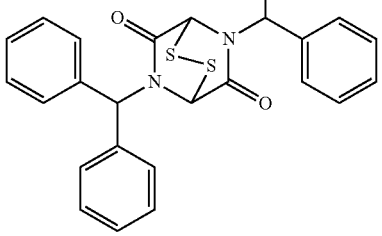

[Chemical Formula 13]
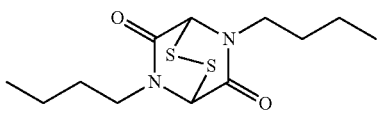

[Chemical Formula 14]
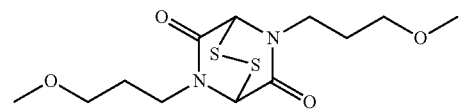

6. The method of claim 2, wherein $R_1$ to $R_4$ are each independently hydrogen, linear or branched C1 to C6 alkyl or alkenyl, alkoxybenzyl, alkoxyalkyl or benzhydryl.

7. The method of claim 2, wherein $R_1$ to $R_4$ are each independently hydrogen, methyl, n-butyl, allyl, 4-methoxybenzyl, 3-methoxypropyl or benzhydryl.

8. The method of claim 2, wherein the epidithiodioxopiperazine derivative is any one of compounds represented by the following Chemical Formulae 7 to 14:

[Chemical Formula 7]
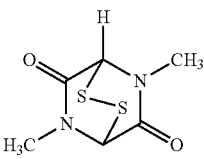

[Chemical Formula 8]
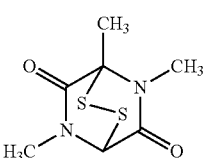

[Chemical Formula 9]
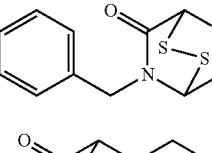

[Chemical Formula 10]
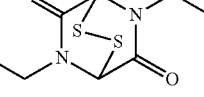

[Chemical Formula 11]
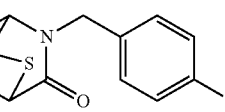

[Chemical Formula 12]

[Chemical Formula 13]
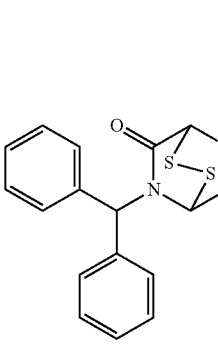

[Chemical Formula 14]
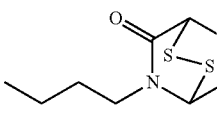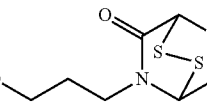

* * * * *

SEQUENCE LISTING

<160> NUMBER OF SEQ ID NOS: 8

<210> SEQ ID NO 1

```
<211> LENGTH: 21
<212> TYPE: RNA
<213> ORGANISM: Artificial Sequence
<220> FEATURE:
<223> OTHER INFORMATION: Made in Lab - human PrxII siRNA-1

<400> SEQUENCE: 1
cgcuugucug aggauuacgu u                                              21

<210> SEQ ID NO 2
<211> LENGTH: 21
<212> TYPE: RNA
<213> ORGANISM: Artificial Sequence
<220> FEATURE:
<223> OTHER INFORMATION: Made in Lab - human PrxII siRNA-2

<400> SEQUENCE: 2
aggaauauuu cuccaaacau u                                              21

<210> SEQ ID NO 3
<211> LENGTH: 21
<212> TYPE: DNA
<213> ORGANISM: Artificial Sequence
<220> FEATURE:
<223> OTHER INFORMATION: Made in Lab - human PrxI siRNA

<400> SEQUENCE: 3
actcaactgc caagtgattu u                                              21

<210> SEQ ID NO 4
<211> LENGTH: 21
<212> TYPE: RNA
<213> ORGANISM: Artificial Sequence
<220> FEATURE:
<223> OTHER INFORMATION: Made in Lab - mouse PrxII siRNA-1

<400> SEQUENCE: 4
aggaauauuu cuccaaacau u                                              21

<210> SEQ ID NO 5
<211> LENGTH: 21
<212> TYPE: RNA
<213> ORGANISM: Artificial Sequence
<220> FEATURE:
<223> OTHER INFORMATION: Made in Lab - siRNA for Rat PrxII

<400> SEQUENCE: 5
gcaacgcgca caucggaaau u                                              21

<210> SEQ ID NO 6
<211> LENGTH: 21
<212> TYPE: RNA
<213> ORGANISM: Artificial Sequence
<220> FEATURE:
<223> OTHER INFORMATION: Made in Lab - siRNA for Rat PrxII

<400> SEQUENCE: 6
gaucacaguc aacgaccuau u                                              21

<210> SEQ ID NO 7
<211> LENGTH: 21
<212> TYPE: RNA
<213> ORGANISM: Artificial Sequence
<220> FEATURE:
<223> OTHER INFORMATION: Made in Lab - siRNA for Rat PrxII

<400> SEQUENCE: 7
```

```
agaauuacgg cguguugaau u                                              21

<210> SEQ ID NO 8
<211> LENGTH: 21
<212> TYPE: RNA
<213> ORGANISM: Artificial Sequence
<220> FEATURE:
<223> OTHER INFORMATION: Made in Lab - siRNA for Rat PrxII

<400> SEQUENCE: 8
acgcugagga cuuccgaaau u                                              21
```